United States Patent
Yang et al.

(12) 
(10) Patent No.: US 6,194,438 B1
(45) Date of Patent: Feb. 27, 2001

(54) DERIVATIVES OF 2-(2-OXO-ETHYLIDENE)-IMIDAZOLIDIN-4-ONE, AND COMPOSITIONS AND METHODS FOR INHIBITING ABNORMAL CELL GROWTH COMPRISING SAID DERIVATIVES

(75) Inventors: Bingwei V. Yang, Waterford; Joseph P. Lyssikatos, Gales Ferry, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/454,058

(22) Filed: Dec. 2, 1999

Related U.S. Application Data

(60) Provisional application No. 60/110,607, filed on Dec. 2, 1998.

(51) Int. Cl.⁷ .................. A61K 31/4427; C07D 401/14
(52) U.S. Cl. .................. 514/333; 548/256; 548/272.7; 548/274.4; 514/341
(58) Field of Search .................. 514/333, 341; 546/256, 272.7, 274.4

(56) References Cited

U.S. PATENT DOCUMENTS

| | | | |
|---|---|---|---|
| 5,948,781 | 9/1999 | Lyssikatos et al. | 514/256 |
| 6,071,935 | 6/2000 | Lyssikatos . | |
| 6,080,769 | 6/2000 | Lyssikatos . | |

FOREIGN PATENT DOCUMENTS

| | | |
|---|---|---|
| 0928788 | 7/1999 | (EP) . |
| WO9749700 | 12/1997 | (WO) . |
| 9857633 | 12/1998 | (WO) . |
| WO9924440 | 5/1999 | (WO) . |

OTHER PUBLICATIONS

Coburn, et al., "Mesoionic Purinone Analogs. VIII. Synthesis and Properties of Mesoionic 5–Substituted–6–methylimidazo[1,2c]pyrimidine–2,7–diones," J. Heterocyclic Chemistry, vol. 19, pp. 567–572, May–Jun. 1982.

*Primary Examiner*—C. S. Aulakh
(74) *Attorney, Agent, or Firm*—Peter C. Richardson; Paul H. Ginsburg; Jeffrey N. Myers

(57) ABSTRACT

The present invention relates to compounds of the formula

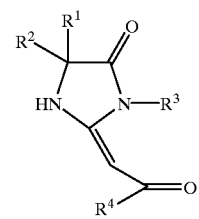

wherein $R^1$, $R^2$, $R^3$ and $R^4$ are as defined herein. The invention also relates to pharmaceutical compositions containing the compounds of Formula I and to methods of inhibiting abnormal cell growth, including cancer, in a mammal by administering the compounds of Formula I to said mammal.

10 Claims, No Drawings

DERIVATIVES OF 2-(2-OXO-ETHYLIDENE)-IMIDAZOLIDIN-4-ONE, AND COMPOSITIONS AND METHODS FOR INHIBITING ABNORMAL CELL GROWTH COMPRISING SAID DERIVATIVES

This application claims the benefit of U.S. Provisional Application No. 60/110,607, filed Dec. 2, 1998.

BACKGROUND OF THE INVENTION

This invention relates to a series of novel derivatives of 2-(2-oxo-ethylidene)-imidazolidin-4-one. The compounds exhibit activity as inhibitors of the enzyme farnesyl protein transferase and are believed to be useful as anti-cancer and anti-tumor agents. This invention also relates to methods of using such compounds in the treatment or prevention of cancer in a mammal, in particular a human, and to pharmaceutical compositions comprising such compounds.

Other compounds that inhibit farnesyl protein transferase and are believed to be useful as anti-cancer and anti-tumor agents are referred to in U.S. patent application 08/863,514, entitled "Adamantyl Substituted Oxindoles as Pharmaceutical Agents", filed Apr. 27, 1997, and PCT/IB97/00584, entitled "Derivatives of 2-(2-Oxo-Ethylidene)-Imidazolidin-4-one", designating the United States, filed May 22, 1997. United States Provisional Application 60/065,097, entitled "Thienopyrimidine and Thienopyridine Derivatives Useful as Anticancer Agents", filed Nov. 11, 1997, also refers to compounds which are believed to be useful as agents for treating cancer and other hyperproliferative diseases, for example psoriasis. The foregoing patent applications are incorporated herein by reference in their entireties.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anti-cancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993). The compounds of the present invention may be active against any tumors that proliferate by virtue of farnesyl protein transferase.

The preceding Kohl et al. publication, as well as all other references discussed below in this application, are also hereby incorporated by reference in their entireties.

SUMMARY OF THE INVENTION

The present invention relates to compounds of the Formula I

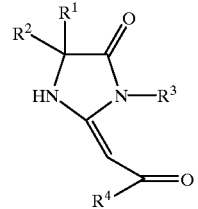

and to pharmaceutically acceptable salts thereof, wherein:

$R^1$ and $R^2$ are each independently selected from the group consisting of $C_1-C_{10}$ alkyl, $C_2-C_{10}$ alkenyl, $C_2-C_{10}$ alkynyl, $-(CH_2)_p(C_6-C_{10}$ aryl), and $-(CH_2)_p(4-10$ membered unsaturated heterocyclyl), wherein p is an integer from 0 through 3, or $R^1$ and $R^2$ form a $C_3-C_6$ cycloalkyl ring, and wherein any of said $R^1$ and $R^2$ groups are optionally substituted with 1 to 3 $R^6$ groups, provided that when $R^1$ and $R^2$ form a $C_3-C_6$ cycloalkyl ring, said $C_3-C_6$ cycloalkyl ring is substituted with at least one $R^6$ selected from $C_2-C_{10}$ alkenyl, $C_2-C_{10}$ alkynyl, and $-(CH_2)_t(C_6-C_{10}$ aryl wherein t is an integer from 1 to 3;

$R^3$ is $-(CH_2)_m(1$ - or 2-adamantyl),$C_1-C_{10}$alkyl, $C_2-C_{10}$alkenyl,$C_2-C_{10}$alkynyl, $-(CH_2)_m(C_6-C_{10}$ aryl),

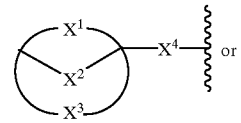

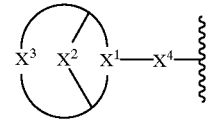

$X^1$, $X^2$, and $X^3$ are each independently $C_1-C_7$ alkylene optionally containing 1 or 2 carbon-carbon double or triple bonds, $X^4$ is a bond or $C_1-C_7$ alkylene optionally containing 1 or 2 carbon-carbon double or triple bonds, and, in Formula (Ib), the $X^4$ moiety is attached to the $X^1$ moiety at any available carbon in the $X^1$ moiety, each of the foregoing $R^3$ groups are substituted with an $R^5$ group and optionally with 1 to 4 $R^6$ groups;

or $R^3$ is $-SO_2R^9$, $-C(O)R^9$, or $-(CH_2)_m(4-10$ membered heterocyclyl) optionally substituted with 1 to 5 $R^6$ groups;

m in the aforementioned R' groups is independently an integer from 0 through 6; and $R^4$ is $C_6-C_{10}$ aryl, 4–10 membered heterocyclyl, or $C_1-C_6$ alkyl, each of said $R^4$ groups being optionally substituted by 1 to 3 $R^6$ groups;

each $R^5$ is independently selected from halo, $C_1-C_6$ alkyl substituted by 1 to 3 halo, nitro, cyano, $-OR^9$, $-C(O)R^9$, $-SR^9$, $-SO_2R^9$, $-SO_3H$, $-S(O)R^9$ $-NR^7R^8$, $-C(O)OR^9$, $-OC(O)R^9$, $-SO_2NR^9R^8$, $-C(O)NR^9R^8$, $-NR^8C(O)R^9$, $-OC(O)NR^9R^8$, $-C(O)ONR^7R^9$, $-NR^8C(O)NR^9R^8$, $-NR^8C(O)O(C_1-C_4$ alkyl), $-C(NR^8)NR^9R^8$, $-C(NCN)NR^9R^8$, $-C(NCN)S(C_1-C_4$ alkyl or $C_1-C_4$ haloalkyl), $-NR^8C(NCN)S(C_1-C_4$ alkyl or $C_1-C_4$ haloalkyl), $-NR^8C(NCN)NR^7R^8$, $-NR^8SO_2(C_1-C_4$ alkyl or $C_1-C_4$ haloalkyl), $-NR^8C(O)C(O)R^8$, $-NR^8C(O)C(O)NR^9R^8$, $-P(O)(OR^7)_2$, and $-(CH_2)_q(4-10$ membered heterocyclyl), q is an integer from 0 through 3, and the alkyl and heterocyclyl moieties of the foregoing $R^5$ groups are optionally substituted by 1 to 3 $R^{10}$ groups;

each $R^7$ is independently selected from $R^5$, $C_1$–$C_6$ alkyl, $C_2$–$C_{10}$ alkenyl, $C_2$–$C_{10}$ alkynyl and —$(CH_2)_t(C_6$–$C_{10}$ aryl), such as phenyl or naphthyl, optionally substituted with 1 to 3 $R^{10}$ groups, t being an integer from 0 through 3;

each $R^7$ is independently hydrogen or $C_1$–$C_4$ alkyl optionally substituted by 1 to 3 halo;

each $R^8$ is independently $R^7$ or —$OR^7$;

each $R^9$ is independently selected from hydrogen, $C_1$–$C_6$ alkyl, —$(CH_2)_q(C_6$–$C_{10}$ aryl), and —$(CH_2)_q$(4–10 membered heterocyclyl), said $R^9$ groups, except H, are optionally substituted with 1 to 3 $R^{10}$ groups, and each q is independently an integer from 0 through 3; and, each $R^{10}$ is independently selected from halo, nitro, cyano, $C_1$–$C_6$ alkyl, $C_1$–$C_6$ haloalkyl, $C_1$–$C_6$ alkoxy, $C_1$–$C_6$ haloalkoxy, —C(O)O($C_1$–$C_6$ alkyl), and $C_6$–$C_{10}$ aryl;

with the proviso that $R^1$ and $R^2$ are not both simultaneously $C_1$–$C_{10}$ alkyl.

Preferably in the compounds of Formula 1, each p integer in $R^1$ and $R^2$ is an integer independently selected from 0 to 3, more preferably an integer independently selected from 1 to 3, 1 being most preferred.

Preferred compounds of Formula I include those wherein one or both of $R^1$ and $R^2$ is —$(CH_2)_p$(4–10 membered unsaturated heterocyclyl) optionally substituted with 1 to 3 $R^6$ groups, more preferably —$(CH_2)_p$(5 or 6 membered unsaturated heterocyclyl). Preferably, each heterocyclyl of $R^1$ and $R^2$ is independently imidazolyl or pyridinyl. In different embodiments, one or both of $R^1$ and $R^2$ is 2-, 3- or 4-pyridinylmethyl; preferably, one or both of $R^1$ and $R^2$ is 4-pyridinylmethyl. In other embodiments, $R^1$ and $R^2$ are each independently imidazol-1-ylmethyl, imidazol-2-ylmethyl, or imidazol-4-ylmethyl, optionally subsituted with 1 to 3 $R^6$ groups; preferably, $R^1$ and $R^2$ are both imidazol-4-ylmethyl, each optionally subsituted with 1 to 3 $R^6$ groups, for example $R^1$ and $R^2$ are both 3-methyl-imidazol-4-ylmethyl or unsubstituted imidazol-4-ylmethyl.

Other preferred compounds of Formula I include those wherein one or both of $R^1$ and $R^2$ is $C_1$–$C_{10}$ alkyl, $C_2$–$C_{10}$ alkenyl, or $C_2$–$C_{10}$ alkynyl, optionally substituted with 1 to 3 $R^6$ groups, provided that $R^1$ and $R^2$ are not both simultaneously $C_1$–$C_{10}$ alkyl. For example, one or both of $R^1$ and $R^2$ can be allyl, 3-methyl-but-2-enyl, or 3-chloro-but-2-enyl.

When $R^9$ is a —$(CH_2)_q$(4–10 membered heterocyclyl) group, the heterocyclyl ring of $R^9$ preferably has 5 or 6 members in its ring. Said 5 or 6 membered heterocyclyl may, however, be substituted with 1 to 3 $R^{10}$ groups as defined above. When $R^9$ is a —$(CH_2)_q(C_6$–$C_{10}$ aryl) group, the aryl ring of $R^9$ preferably is phenyl or naphthyl, which may be substituted with 1 to 3 $R^{10}$ groups as defined above.

Other preferred compounds of Formula I include those wherein $R^3$ is —$(CH_2)_m$(4–10 membered heterocyclyl) optionally substituted with 1 to 5 $R^6$ groups, preferably wherein m is an integer 0 or 1. Preferably, such an $R_3$ group is unsubstituted or substituted with from 1 to 3 $R^6$ groups. In one preferred embodiment, $R^3$ is —$(CH_2)_m$(4–10 membered azacyclyl), preferably saturated. Even more preferably, $R^3$ is saturated —$(CH_2)_m$(4–10 membered azabicyclyl). For example, $R^3$ may be —$(CH_2)_m$(azabicylohexyl), —$(CH_2)_m$(azabicyloheptyl), or —$(CH_2)_m$(azabicylooctyl), optionally substituted with 1 to 3 $R^6$ groups. Other preferred compounds of the invention include those wherein a nitrogen ring member of an azacyclyl $R^3$ group is substituted with $R^5$, wherein $R^5$ is —$SO_2R^9$, —$SO_2NR^9R^8$, or —C(O)$OR^9$. In another embodiment of the invention, $R^3$ is $(CH_2)_m$(4–10 membered monocyclic azacyclyl), preferably saturated.

Other preferred compounds of the invention include compounds of Formula I wherein $R^3$ is —$(CH_2)_m(C_6$–$C_{10}$ aryl) substituted with an $R^5$ group and optionally with 1 to 4 $R^6$ groups.

Preferred compounds of the invention wherein $R^3$ is a 1α,5α,6α-3-aza-bicyclo[3.1.0]hex-6-yl include the following:

4-{[1-(1α,5α,6α-3-tert-Butoxylcarbonyl-3-aza-bicyclo [3.1.0]hex-6-yl)-5-oxo-4,4-bis-pyridin-4-ylmethyl-imidazolidin-2-ylidene]-acetyl}-benzonitrile;

4-{[1-(1α,5α,6α-3-Aza-bicyclo[3.1.0]hex-6-yl)-5oxo-4, 4-bis-pyridin-4-ylmethyl-imidazolidin-2-ylidene]-acetyl}-benzonitrile;

4-({5-Oxo-[1-1α,5α,6α-3-(1-phenyl-1H-tetrazol-5-yl)-3-aza-bicyclo[3.1.0]hex-6-yl]-4,4-bis-pyridin-4-ylmethyl-imidazolidin-2-ylidene}-acetyl)-benzonitrile;

1α,5α,6α-6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hexane-3-carboxylic acid benzyl ester;

4-({1-[1α,5α,6α-3-(3,3-Dimethyl-butyryl)-3-aza-bicyclo [3.1.0]hex-6-yl]-5-oxo-4,4-bis-pyridin-4-ylmethyl-imidazolidin-2-ylidene}-acetyl)-benzonitrile;

4-({5-Oxo-4,4-bis-pyridin-4-ylmethyl-1-[1α,5α,6α-3-(thiophen-2-yl-acetyl)-3-aza-bicyclo[3.1.0]hex-6-yl]-imidazolidin-2-ylidene}-acetyl)-benzonitrile;

1α,5α,6α-(6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hex-3-yl)-phosphonic acid diethyl ester;

4-{[1-(1α,5α,6α-3-Benzenesulfonyl-3-aza-bicyclo [3.1.0]hex-6-yl)-5-oxo-4,4-bis-pyridin-4-ylmethyl-imidazolidin-2-ylidene]-acetyl}-benzonitrile;

4-({1-[1α,5α,6α-3-(4-Methoxy-benzenesulfonyl)-3-aza-bicyclo[3.1.0]hex-6-yl]-5-oxo-4,4-bis-pyridin-4-ylmethyl-imidazolidin-2-ylidene}-acetyl)-benzonitrile;

4-({1-[1α,5α,6α-3-(4-Fluoro-benzenesulfonyl)-3-aza-bicyclo[3.1.0]hex-6-yl]-5-oxo-4,4-bis-pyridin-4-ylmethyl-imidazolidin-2-ylidene}-acetyl)-benzonitrile;

4-{[5-Oxo-1-(1α,5α,6α-3-phenylmethanesulfonyl-3-aza-bicyclo[3.1.0]hex-6-yl)-4,4-bis-pyridin-4-ylmethyl-imidazolidin-2-ylidene]-acetyl}-benzonitrile;

4-{[1-(1α,5α,6α-3-(4-Chlorobenzene)sulfonyl-3-aza-bicyclo[3.1.0]hex-6-yl)-5-oxo-4,4-bis-pyridin-4-ylmethyl-imidazolidin-2-ylidene]-acetyl}-benzonitrile;

4-({1-[1α,5α,6α-3-(Naphthalene-2-sulfonyl)-3-aza-bicyclo[3.1.0]hex-6-yl]-5-oxo-4,4-bis-pyridin-4-ylmethyl-imidazolidin-2-ylidene}-acetyl)-benzonitrile;

4-({5-Oxo-4,4-bis-pyridin-4-ylmethyl-1-[1α,5α,6α-3-(toluene-4-sulfonyl)-3-aza-bicyclo[3.1.0]hex-6-yl]-imidazolidin-2-ylidene}-acetyl)-benzonitrile;

4-({5-Oxo-4,4-bis-pyridin-4-ylmethyl-1-[1α,5α,6α-3-(toluene-2-sulfonyl)-3-aza-bicyclo[3.1.0]hex-6-yl]-imidazolidin-2-ylidene}-acetyl)-benzonitrile;

4-({5-Oxo-1-[1α,5α,6α-3-(piperidine-1-sulfonyl)-3-aza-bicyclo[3.1.0]hex-6-yl]-4,4-bis-pyridin-4-ylmethyl-imidazolidin-2-ylidene}-acetyl)-benzonitrile;

4-({1-[1α,5α,6α-3-(4-Methyl-piperazine-1-sulfonyl)-3-aza-bicyclo[3.1.0]hex-6-yl]-5-oxo-4,4-bis-pyridin-4-ylmethyl-imidazolidin-2-ylidene}-acetyl)-benzonitrile;

4-({5-Oxo-4,4-bis-pyridin-4-ylmethyl-1-[1α,5α,6α-3-(thiophene-2-sulfonyl)-3-aza-bicyclo[3.1.0]hex-6-yl]-imidazolidin-2-ylidene}-acetyl)-benzonitrile;

4-(1α,5α,6α-6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hexane-3-sulfonyl)-piperazine-1-carboxylic acid tert-butyl ester;

4-({1-[1α,5α,6α-3-(5-Bromo-thiophene-2-sulfonyl)-3-aza-bicyclo[3.1.0]hex-6-yl]-5-oxo-4,4-bis-pyridin-4-ylmethyl-imidazolidin-2-ylidene}-acetyl)-benzonitrile;

4-({1-[1α,5α,6α-3-(4-Ethyl-piperazine-1-sulfonyl)-3-aza-bicyclo[3.1.0]hex-6-yl]-5-oxo-4,4-bis-pyridin-4-ylmethyl-imidazolidin-2-ylidene}-acetyl)-benzonitrile;

4-({1-[1α,5α,6α-3-(3-Chloro-propane-1-sulfonyl)-3-aza-bicyclo[3.1.0]hex-6-yl]-5-oxo-4,4-bis-pyridin-4-ylmethyl-imidazolidin-2-ylidene}-acetyl)-benzonitrile;

4-({5-Oxo-1-[1α,5α,6α-3-(propane-1-sulfonyl)-3-aza-bicyclo[3.1.0]hex-6-yl]-4,4-bis-pyridin-4-ylmethyl-imidazolidin-2-ylidene}-acetyl)-benzonitrile;

1-(1α,5α,6α-6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hexane-3-sulfonyl)-piperidine-4-carboxylic acid ethyl ester;

4-({5-Oxo-1-[1α,5α,6α-3-(4-propyl-piperidine-1-sulfonyl)-3-aza-bicyclo3.1.0]hex-6-yl]-4,4-bis-pyridin-4-ylmethyl-imidazolidin-2-ylidene}-acetyl)-benzonitrile;

4-({1-[1α,5α,6α-3-(2,5-Dichloro-thiophene-3-sulfonyl)-3-aza-bicyclo[3.1.0]hex-6-yl]-5-oxo-4,4-bis-pyridin-4-ylmethyl-imidazolidin-2-ylidene}-acetyl)-benzonitrile;

4-({1-[1α,5α,6α-3-(4-Isopropyl-piperazine-1-sulfonyl)-3-aza-bicyclo[3.1.0]hex-6-yl]-5-oxo-4,4-bis-pyridin-4-ylmethyl-imidazolidin-2-ylidene}-acetyl)-benzonitrile;

1α,5α,6α-6-{2-[2-(4-Cyano-phenyl)-2-oxo-ethylidene]-5-oxo-4,4-bis-pyridin-4-ylmethyl-imidazolidin-1-yl}-3aza-bicyclo[3.1.0]hexane-3-sulfonic acid dimethylamide;

4-{[1-(1α,5α,6α-3-Chloromethanesulfonyl-3-aza-bicyclo[3.1.0]hex-6-yl)-5-oxo-4,4-bis-pyridin-4-ylmethyl-imidazolidin-2-ylidene]-acetyl}-benzonitrile;

4-{[1α,5α,6β-1-(3-Benzenesulfonyl-3aza-bicyclo[3.1.0]hex-6-ylmethyl-5-oxo-4,4-bis-pyridin-4-ylmethyl-imidazolidin-2-ylidene]-acetyl}-benzonitrile;

4-{[1α,5α,6α-1-(3-Benzenesulfonyl-3-aza-bicyclo[3.1.0]hex-6-ylmethyl)-5-oxo-4,4-bis-pyridin-4-ylmethyl-imidazolidin-2-ylidene]-acetyl}-benzonitrile; and 4-{[1α,5α,6β-1-(3-Benzenesulfonyl-3-aza-bicyclo[3.1.0]hex-6-yl)-5-oxo-4,4-bis-pyridin-4-ylmethyl-imidazolidin-2-ylidene]-acetyl}benzonitrile.

Other preferred compounds of the invention wherein $R^3$ is a —$(CH_2)_m$(1α,5α,6α-3-aza-bicyclo[3.1.0]hex-6-yl) group include:

1α,5α,6α-6-{4-Allyl-2-[2-(4-cyano-phenyl)-2-oxo-ethylidene]-5-oxo-4-pyridin-4-ylmethyl-imidazolidin-1-yl}-3-aza-bicyclo[3.1.0]hexane-3-carboxylic acid tert-butyl ester;

4-{[4-Allyl-1-(1α,5α,6α-3-benzenesulfonyl-3-aza-bicyclo[3.1.0]hex-6-yl)-5-oxo-4-pyridin-4-ylmethyl-imidazolidin-2-ylidene]-acetyl}-benzonitrile;

4-{[5-Oxo-4-allyl-4-pyridin-4-ylmethyl-1-(1α,5α,6α-3-(thiophene-2-acetyl)-3-aza-bicyclo[3.1.0]hex-6-yl)imidazolidin-2-ylidene]-acetyl}-benzonitrile;

4-({4-Allyl-5-oxo-4-pyridin-4-ylmethyl-1-[1α,5α,6α-3-(thiophen-2-yl-sulfonyl)-3-aza-bicyclo[3.1.0]hex-6-yl]-imidazolidin-2-ylidene}-acetyl)-benzonitrile;

1α,5α,6α-6-[2-[2-(4-Cyano-phenyl)-2-oxo-ethylidene]-4-(3-methyl-but-2-enyl)-5-oxo-4-pyridin-4-ylmethyl-imidazolidin-1-yl]-3-aza-bicyclo[3.1.0]hexane-3-carboxylic acid tert-butyl ester;

4-{[1-[1α,5α,6α-3-(5-Bromo-thiophene-2-sulfonyl)-3-aza-bicyclo[3.1.0]hex-6-yl]-4-(3-methyl-but-2-enyl)-5-oxo-4-pyridin-4-ylmethyl-imidazolidin-2-ylidene]-acetyl}-benzonitrile;

1α,5α,6α-6-{2-[2-(4-Cyano-phenyl)-2-oxo-ethylidene]-5-oxo-4-pyridin-4-ylmethyl-4-thiophen-3-ylmethyl-imidazolidin-1-yl}-3-aza-bicyclo[3.1.0]hexane-3-carboxylic acid tert-butyl ester;

4-{[1-(1α,5α,6α-3-Benzenesulfonyl-3-aza-bicyclo[3.1.0]hex-6-yl)-5-oxo-4-pyridin-4-ylmethyl-4-thiophen-3-ylmethyl-imidazolidin-2-ylidene]-acetyl}-benzonitrile;

1α,5α,6α-6-{4-(3-Chloro-but-2-enyl)-2-[2-(4-cyano-phenyl)-2-oxo-ethylidene]-5-oxo-4-pyridin-4-ylmethyl-imidazolidin-1-yl}-3-aza-bicyclo[3.1.0]hexane-3-carboxylic acid tert-butyl ester; and 4-{[1-[1α,5α,6α-3-(5-Bromo-thiophene-2-sulfonyl)-3-aza-bicyclo[3.1.0]hex-6-yl]-4-(3-chloro-but-2-enyl)-5-oxo-4-pyridin-4-ylmethyl-imidazolidin-2-ylidene]-acetyl}-benzonitrile.

Other compounds of the invention include compounds of Formula I wherein $R^3$ is —$(CH_2)_m$(piperidin-2-yl), —$(CH_2)_m$(piperidin-3-yl), or —$(CH_2)_m$(piperidin-4-yl). Preferred examples of such compounds include:

4-{[1-(1-Benzenesulfonyl-piperidin-4-ylmethyl)-5-oxo-4,4-bis-pyridin-4-ylmethyl-imidazolidin-2-ylidene]-acetyl}-benzonitrile;

4-{2-[2-(4-Cyano-phenyl)-2-oxo-ethylidene]-5-oxo-4,4-bis-pyridin-4-ylmethyl-imidazolidin-1-ylmethyl}-piperidine-1-sulfonic acid dimethylamide;

4-({5-Oxo-1-[1-(1-phenyl-1H-tetrazol-5-yl)-piperidin-4-ylmethyl]-4,4-bis-pyridin-4-ylmethyl-imidazolidin-2-ylidene}-acetyl)-benzonitrile;

4-({1-[1-(1-Methyl-1H-imidazole-4-sulfonyl)-piperidin-4-ylmethyl]-5-oxo-4,4-bis-pyridin-4-ylmethyl-imidazolidin-2-ylidene}-acetyl)-benzonitrile; and 4-({5-Oxo-4,4-bis-pyridin-4-ylmethyl-1-[I -(thiophene-2-sulfonyl)-piperidin-4-ylmethyl]-imidazolidin-2-ylidene}-acetyl)-benzonitrile.

Other compounds of the invention include compounds of Formula I wherein $R^3$ is —$(CH_2)_m$(pyrrolidin-2-yl) or $(CH_2)_m$(pyrrolidin-3-yl). Preferred examples of such compounds include:

4-{[1-(1-Benzenesulfonyl-pyrrolidin-3-yl)-5-oxo-4,4bis-pyridin-4-ylmethyl-imidazolidin-2-ylidene]-acetyl}-benzonitrile;

4-{[1-(1-Benzenesulfonyl-pyrrolidin-3-ylmethyl)-5-oxo-4,4-bis-pyridin-4-ylmethyl-imidazolidin-2-ylidene]-acetyl}-benzonitrile; and 4-({5-Oxo-4,4-bis-pyridin-4-ylmethyl-1-[1-(thiophene-2-sulfonyl)-pyrrolidin-3-ylmethyl]-imidazolidin-2-ylidene}-acetyl)-benzonitrile.

Other compounds of the invention include compounds of Formula I wherein $R^3$ is —$(CH_2)_m$(1α,6α,7α-3-aza-bicyclo[4.1.0]hept-7-yl), optionally substituted with 1 to 3 $R^6$ groups. Specific examples of such compounds include:

4-{[1α,6α,7α-1-(3-Benzenesulfonyl-3-aza-bicyclo[4.1.0]hept-7-ylmethyl)-5-oxo-4,4-bis-pyridin-4-ylmethyl-imidazolidin-2-ylidene]-acetyl}-benzonitrile; and 4-{[1α,6α,7α-1-(3-Benzenesulfonyl-3-aza-bicyclo[4.1.0]hept-7-yl)-5-oxo-4,4-bis-pyridin-4-ylmethyl-imidazolidin-2-ylidene]-acetyl}-benzonitrile.

Other preferred compounds of the invention are wherein $R^3$ is $(CH_2)_m$(4–10 membered heterocyclyl) and $R^1$ and $R^2$ are both an imadazolyl group optionally subsituted with 1 to 3 $R^6$ groups. Examples include:

4-{[1-(1α,5α,6α-3-Benzenesulfonyl-3-aza-bicyclo[3.1.0]hex-6-yl)-4,4-bis-(1H-imidazol-4-ylmethyl)-5-oxo-imidazolidin-2-ylidene]-acetyl}-benzonitrile;

4-({4,4-Bis-(1H-imidazol-4-ylmethyl)-1-[1α,5α,6α-3-(4-methyl-piperidine-1-sulfonyl)-3-aza-bicyclo[3.1.0]hex-6-yl]-5oxo-imidazolidin-2-ylidene}-acetyl)-benzonitrile;

4-{[1-[1α,5α,6α-3-(5-Bromo-thiophene-2-sulfonyl)-3-aza-bicyclo[3.1.0]hex-6-yl]-4,4-bis-(1H-imidazol-4-ylmethyl)-5-oxo-imidazolidin-2-ylidene]-acetyl}-benzonitrile;

4-{[1-(1α,5α,6α-3-Aza-3-(tert-butoxylcarbonyl)-bicyclo[3.1.0]hex-6-yl)-4,4-bis-(3-methyl-3H-imidazol-4-ylmethyl)-5-oxo-imidazolidin-2-ylidene]-acetyl}-benzonitrile;

4-{[1-(1α,5α,6α-3-Aza-bicyclo[3.1.0]hex-6-yl)-4,4-bis-(3-methyl-3H-imidazol-4-ylmethyl)-5-oxo-imidazolidin-2-ylidene]-acetyl}-benzonitrile;

4-{[1-(1α,5α,6α-3-Benzenesulfonyl-3-aza-bicyclo[3.1.0]hex-6-yl)-4,4-bis-(3-methyl-3H-imidazol-4-ylmethyl)-5-oxo-imidazolidin-2-ylidene]-acetyl}-benzonitrile;

4-({4,4-Bis-(3-methyl-3H-imidazol-4-ylmethyl)-1-[1α,5α,6α-3-(4-methyl-piperazine-1-sulfonyl)-3-aza-bicyclo[3.1.0]hex-6-yl]-5-oxo-imidazolidin-2-ylidene}-acetyl)-benzonitrile; and 4-{[1-[1α,5α,6α-3-(5-Bromo-thiophene-2-sulfonyl)-3-aza-bicyclo[3.1.0]hex-6-yl]-4,4-bis-(3-methyl-3H-imidazol-4-ylmethyl)-5-oxo-imidazolidin-2-ylidene]-acetyl}-benzonitrile.

Other preferred compounds of the invention include compounds of Formula I wherein $R^3$ is —$(CH_2)_m$(8α-aza-bicyclo[3.2.1]octane) or —$(CH_2)_m$(8β-aza-bicyclo[3.2.1]octane), optionally substituted with 1 to 3 $R^6$ groups. Preferred examples of such compounds include:

3-{2-[2-(4-Cyano-phenyl)-2-oxo-ethylidene]-5-oxo-4,4-bis-pyridin-4-ylmethyl-imidazolidin-1-ylmethyl}-8α-aza-bicyclo[3.2.1]octane-8-carboxylic acid tert-butyl ester;

4-{[1-(8α-Aza-bicyclo[3.2.1]oct-3-ylmethyl)-5-oxo-4,4-bis-pyridin-4-ylmethyl-imidazolidin-2-ylidene]-acetyl}-benzonitrile;

4-{[1-(8-Acetyl-8α-aza-bicyclo[3.2.1]oct-3-ylmethyl-5-oxo-4,4-bis-pyridin-4-ylmethyl-imidazolidin-2-ylidene]-acetyl}-benzonitrile;

4-{[1-(8-Methanesulfonyl-8α-aza-bicyclo[3.2.1]oct-3-ylmethyl)-5-oxo-4,4-bis-pyridin-4-ylmethyl-imidazolidin-2-ylidene]-acetyl}-benzonitrile;

3-{2-[2-(4-Cyano-phenyl)-2-oxo-ethylidene]-5-oxo-4,4-bis-pyridin-4-ylmethyl-imidazolidin-1-ylmethyl}-8α-aza-bicyclo[3.2.1]octane-8-carboxylic acid ethyl ester;

4-{[1-(8-Formyl-8α-aza-bicyclo[3.2.1]oct-3-ylmethyl)-5-oxo-4,4-bis-pyridin-4-ylmethyl-imidazolidin-2-ylidene]-acetyl}-benzonitrile;

3-{2-[2-(4-Cyano-phenyl)-2-oxo-ethylidene]-5-oxo-4,4-bis-pyridin-4-ylmethyl-imidazolidin-1-ylmethyl}-8α-aza-bicyclo[3.2.1]octane-8-carboxylic acid methyl ester;

4-{[1-(8-Benzenesulfonyl-8α-aza-bicyclo[3.2.1]oct-3-ylmethyl)-5-oxo-4,4-bis-pyridin-4-ylmethyl-imidazolidin-2-ylidene]-acetyl}-benzonitrile;

3-{2-[2-(4-Cyano-phenyl)-2-oxo-ethylidene]-5-oxo-4,4-bis-pyridin-4-ylmethyl-imidazolidin-1-ylmethyl}-8α-aza-bicyclo[3.2.1]octane-8-sulfonic acid dimethylamide;

4-{[1-(8-Ethanesulfonyl-8α-aza-bicyclo[3.2.1]oct-3-ylmethyl)-5-oxo-4,4-bis-pyridin-4-ylmethyl-imidazolidin-2-ylidene]-acetyl}-benzonitrile;

4-({5-Oxo-1-[8-(propane-1-sulfonyl)-8α-aza-bicyclo[3.2.1]oct-3-ylmethyl-4,4-bis-pyridin-4-ylmethyl-imidazolidin-2-ylidene}-acetyl)-benzonitrile;

3-{2-[2-(4-Cyano-phenyl)-2-oxo-ethylidene]-5-oxo-4,4-bis-pyridin-4-ylmethyl-imidazolidin-1-ylmethyl}-8β-aza-bicyclo[3.2.1]octane-8-carboxylic acid tert-butyl ester;

4-{[1-(8β-Aza-bicyclo[3.2.1]oct-3-ylmethyl)-5-oxo-4,4-bis-pyridin-4-ylmethyl-imidazolidin-2-ylidene]-acetyl}-benzonitrile;

4-{[1-(8-Acetyl-8β-aza-bicyclo[3.2.1]oct-3-ylmethyl)-5-oxo-4,4-bis-pyridin-4-ylmethyl-imidazolidin-2-ylidene]-acetyl}-benzonitrile;

4-{[1-(8-Methanesulfonyl-8β-aza-bicyclo[3.2.1]oct-3-ylmethyl)-5oxo-4,4-bis-pyridin-4-ylmethyl-imidazolidin-2-ylidene]-acetyl}-benzonitrile;

4-{[1-(8-Benzenesulfonyl-8β-aza-bicyclo[3.2.1]oct-3-ylmethyl)-5-oxo-4,4-bis-pyridin-4-ylmethyl-imidazolidin-2-ylidene]-acetyl}-benzonitrile;

3-{2-[2-(4-Cyano-phenyl)-2-oxo-ethylidene]5-oxo-4,4-bis-pyridin-4-ylmethyl-imidazolidin-1-ylmethyl}-8α-aza-bicyclo[3.2.1]octane-8-sulfonic acid dimethylamide; and 4-({1-[8-(1-Methyl-1H-imidazole-4-sulfonyl)-8β-aza-bicyclo[3.2.1]oct-3-ylmethyl]-5-oxo-4,4-bis-pyridin-4-ylmethyl-imidazolidin-2-ylidene}-acetyl)-benzonitrile.

Other preferred compounds of the invention include compounds of Formula I wherein $R^3$ is —$(CH_2)_m(C_6-C_{10}$ aryl) substituted with an $R^5$ group and optionally with 1 to 4 $R^6$ groups. Preferred compounds wherein $R^3$ is —$(CH_2)_m(C_6-C_{10}$ aryl) substituted with an $R^5$ group and optionally with 1 to 4 $R^6$ groups include:

4-{2-[2-(4-Cyano-phenyl)-2-oxo-ethylidene]-5-oxo-4,4-bis-pyridin-4-ylmethyl-imidazolidin-1-ylmethyl}-N,N-dimethyl-benzenesulfonamide;

4-{[1-(3-Chloro-benzyl)-5-oxo-4,4-bis-pyridin-4-ylmethyl-imidazolidin-2-ylidene]-acetyl}-benzonitrile;

4-{[1-(3-Methoxy-benzyl)-5-oxo-4,4-bis-pyridin-4-ylmethyl-imidazolidin-2-ylidene]-acetyl}-benzonitrile;

4-{[1-(3-Fluoro-benzyl)-5-oxo-4,4-bis-pyridin-4-ylmethyl-imidazolidin-2-ylidene]-acetyl}-benzonitrile;

4-{[1-(2-Chloro-benzyl)-5-oxo-4,4-bis-pyridin-4-ylmethyl-imidazolidin-2-ylidene]-acetyl}-benzonitrile;

4-{[1-(4-Methanesulfonyl-benzyl)-5-oxo-4,4-bis-pyridin-4-ylmethyl-imidazolidin-2-ylidene]-acetyl}-benzonitrile; and 4-{[1-(2-Methoxy-benzyl)-5-oxo-4,4-bis-pyridin-4-ylmethyl-imidazolidin-2-ylidene]-acetyl}-benzonitrile.

This invention also provides a compound of the formula

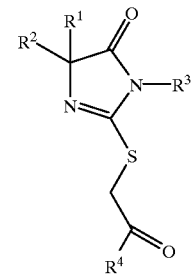

VIII wherein:

$R^1$ and $R^2$ are each independently selected from the group consisting of $C_1-C_{10}$ alkyl, $C_2-C_{10}$ alkenyl, $C_2-C_{10}$ alkynyl, —(CH$_2$)$_p$(C$_6$–C$_{10}$ aryl), and —(CH$_2$)$_p$(4–10 membered unsaturated heterocyclyl), wherein p is an integer from 0 through 3, or R$^1$ and R$^2$ form a C$_3$–C$_6$ cycloalkyl ring, and wherein any of said R$^1$ and R$^2$ groups are optionally substituted with 1 to 3 R$^6$ groups;

R$^3$ is —(CH$_2$)$_m$(1- or 2-adamantyl),C$_1$–C$_{10}$alkyl, C$_2$–C$_{10}$alkenyl,C$_2$–C$_{10}$alkynyl, —(CH$_2$)$_m$(C$_6$–C$_{10}$ aryl),

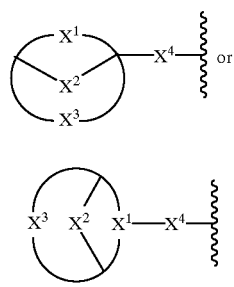

(Ia)

or (Ib)

X$^1$, X$^2$, and X$^3$ are each independently C$_1$–C$_7$ alkylene optionally containing 1 or 2 carbon-carbon double or triple bonds, X$^4$ is a bond or C$_1$–C$_7$ alkylene optionally containing 1 or 2 carbon-carbon double or triple bonds, and, in Formula (Ib), the X$^4$ moiety is attached to the X$^1$ moiety at any available carbon in the X$^1$ moiety, each of the foregoing R$^3$ groups are substituted with an R$^5$ group and optionally With 1 to 4 R$^6$ groups;

or R$^3$ is SO$_2$R$^9$, —C(O)R$^9$, or —(CH$_2$)$_m$(4–10 membered heterocyclyl) optionally substituted with 1 to 5 R$^6$ groups;

m in the aforementioned R$^3$ groups is independently an integer from 0 through 6; and R$^4$ is C$_6$–C$_{10}$ aryl, 4–10 membered heterocyclyl, or C$_1$–C$_6$ alkyl, each of said R$^4$ groups being optionally substituted by 1 to 3 R$^1$ groups;

each R$^5$ is independently selected from halo, C$_1$–C$_6$ alkyl substituted by 1 to 3 halo, nitro, cyano, —OR$^9$, —C(O)R$^9$, —SR$^9$, —SO$_2$R$^9$, —SO$_3$H, —S(O)R$^7$, —NR$^7$R$^8$, —C(O)OR$^9$, —OC(O)R$^9$, —SO$_2$NR$^9$R$^8$, —C(O)NR$^9$R$^8$, —NR$^8$C(O)R$^9$, —OC(O)NR$^9$R$^8$, —C(O)ONR$^7$R$^9$, —NR$^8$C(O)NR$^9$R$^8$, —NR$^8$C(O)O(C$_1$–C$_4$ alkyl), —C(NR$^8$)NR$^9$R$^8$, —C(NCN)NR$^9$R$^8$, —C(NCN)S(C$_1$–C$_4$ alkyl or C$_1$–C$_4$ haloalkyl), —NR$^8$C(NCN(S(C$_1$–C$_4$ alkyl or C$_1$–C$_4$ haloalkyl), —NR$^8$C(NCN)NR$^7$R$^8$, —NR$^8$SO$_2$(C$_1$–C$_4$ alkyl or C$_1$–C$_4$ haloalkyl), —NR$^8$C(O)C(O)R$^8$, —NR$^8$C(O)C(O)NR$^9$R$^8$, —P(O)(OR$^7$)$_2$, and —(CH$_2$)$_q$(4–10 membered heterocyclyl), q is an integer from 0 through 3, and the alkyl and heterocyclyl moieties of the foregoing R$^5$ groups are optionally substituted by 1 to 3 R$^{10}$ groups;

each R$^6$ is independently selected from R$^5$, C$_1$–C$_6$, alkyl, C$_2$–C$_{10}$ alkenyl,C$_2$–C$_{10}$ alkynyl and —(CH$_2$)$_t$(C$_6$–C$_{10}$ aryl) optionally substituted with 1 to 3 R$^{10}$ groups, t being an integer from 0 through 3;

each R$^7$ is independently hydrogen or C$_1$–C$_4$ alkyl optionally substituted by 1 to 3 halo;

each R$^8$ is independently R$^7$ or —OR$^7$;

each R$^9$ is independently selected from hydrogen, C$_1$–C$_6$ alkyl, —(CH$_2$)$_q$(C$_6$–C$_{10}$ aryl), and —(CH$_2$)$_q$(4–10 membered heterocyclyl), said R$^9$ groups, except H, are optionally substituted with 1 to 3 R$^{10}$ groups, and each q is independently an integer from 0 through 3; and, each R$^{10}$ is independently selected from halo, nitro, cyano, C$_1$–C$_6$ alkyl, C$_1$–C$_6$ haloalkyl, C$_1$–C$_6$ alkoxy, C$_1$–C$_6$ haloalkoxy, —C(O)O(C$_1$–C$_6$ alkyl), and C$_6$–C$_{10}$ aryl;

with the proviso that R$^1$ and R$^2$ are not both simultaneously C$_1$–C$_{10}$ alkyl.

Compounds of Formula VIII are useful as intermediates for preparing compounds of Formula I.

This invention also provides a compound of the formula

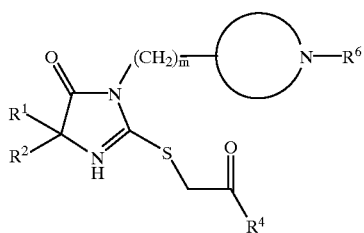

XIV wherein:

R$^1$ and R$^2$ are each independently selected from the group consisting of C$_1$–C$_{10}$ alkyl, C$_2$–C$_{10}$ alkenyl, C$_2$–C$_{10}$ alkynyl, —(CH$_2$)$_p$(C$_6$–C$_{10}$ aryl), and —(CH)(4–10 membered unsaturated heterocyclyl), wherein p is an integer from 0 through 3, or R$^1$ and R$^2$ form a C$_3$–C$_6$ cycloalkyl ring, and wherein any of said R$^1$ and R$^2$ groups are optionally substituted with 1 to 3 R$^6$ groups;

m is an integer from 0 through 6;

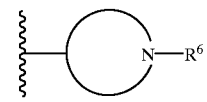

is a saturated 4–10 membered heteroazacyclyl group optionally substituted with from 1 to 4 further R$^6$ groups;

and R$^4$ is C$_6$–C$_{10}$ aryl, 4–10 membered heterocyclyl, or C$_1$–C$_6$ alkyl, each of said R$^4$ groups being optionally substituted by 1 to 3 R$^6$ groups;

each R$^6$ is independently selected from R$^5$, C$_1$–C$_6$ alkyl, C$_2$–C$_{10}$ alkenyl,C$_2$–C$_{10}$ alkynyl and —(CH$_2$)$_t$(C$_6$–C$_{10}$ aryl) optionally substituted with1 to 3 R$^{10}$ groups, t being an integer from 0 through 3;

each R$^5$ is independently selected from halo, C$_1$–C$_6$ alkyl substituted by 1 to 3 halo, nitro, cyano, —OR$^9$, —C(O)R$^9$, —SR$^9$, —SO$_2$R$^9$, —SO$_3$H, —S(O)R$^7$, —NR$^7$R$^8$, —C(O)OR$^9$, —OC(O)R$^9$, —SO$_2$NR$^9$R$^8$, —C(O)NR$^9$R$^8$, —NR$^8$C(O)R$^9$, —OC(O)NR$^9$R$^8$, —C(O)ONR$^7$R$^9$, —NR$^8$C(O)NR$^9$R$^8$, —NR$^8$C(O)O(C$_1$–C$_4$ alkyl), —C(NR$^8$)NR$^9$R$^8$, —C(NCN)NR$^9$R$^8$, —C(NCN)S(C$_1$–C$_4$ alkyl or C$_1$–C$_4$ haloalkyl), —NR$^8$C(NCN)S(C$_1$–C$_4$ alkyl or C$_1$–C$_4$ haloalkyl), —NR$^8$C(NCN)NR$^7$R$^8$, —NR$^8$SO$_2$(C$_1$–C$_4$ alkyl or C$_1$–C$_4$ haloalkyl), —NR$^8$C(O)C(O)R$^8$, —NR$^8$C(O)C(O)NR$^9$R$^8$, —P(O)(OR$^7$)$_2$, and —(CH$_2$)$_q$(4–10 membered heterocyclyl), q is an integer from 0 through 3, and the alkyl and heterocyclyl moieties of the foregoing R$^5$ groups are optionally substituted by 1 to 3 R$^{10}$ groups;

each R$^7$ is independently hydrogen or C$_1$–C$_4$ alkyl optionally substituted by 1 to 3 halo;

each R$^1$ is independently R$^7$ or —OR$^7$;

each R$^9$ is independently selected from hydrogen, C$_1$–C$_6$ alkyl, (CH$_2$)$_q$(C$_6$–C$_{10}$ aryl), and —(CH$_2$)$_q$(4–10 membered heterocyclyl), said R$^9$ groups, except H, are optionally substituted with 1 to 3 R$^{10}$ groups, and each q is independently an integer from 0 through 3; and, each R$^{10}$ is independently selected from halo, nitro, cyano, C$_1$–C$_6$ alkyl, C$_1$–C$_6$ haloalkyl, C$_1$–C$_6$ alkoxy, C$_1$–C$_6$ haloalkoxy, —C(O)O(C$_1$–C$_6$ alkyl), and C$_6$–C$_{10}$ aryl;

with the proviso that $R^1$ and $R^2$ are not both simultaneously $C_1$–$C_{10}$ alkyl.

Compounds of Formula XIV are useful as intermediates for preparing compounds of Formula I.

This invention also provides a compound of the formula Ic

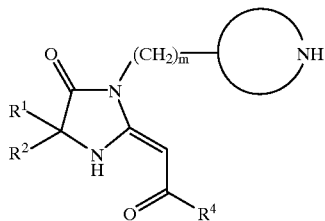

wherein:

$R^1$ and $R^2$ are each independently selected from the group consisting of $C_1$–$C_{10}$ alkyl, $C_2$–$C_{10}$ alkenyl, $C_2$–$C_{10}$ alkynyl, —$(CH_2)_p(C_6$–$C_{10}$ aryl), and —$(CH_2)_p$(4–10 membered unsaturated heterocyclyl), wherein p is an integer from 0 through 3, or $R^1$ and $R^2$ form a $C_3$–$C_6$ cycloalkyl ring, and wherein any of said $R^1$ and $R^2$ groups are optionally substituted with 1 to 3 $R^6$ groups;

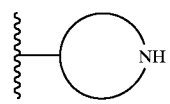

is a saturated 4–10 membered heteroazacyclyl group;

m is an integer from 0 through 6;

and $R^4$ is $C_6$–$C_{10}$ aryl, 4–10 membered heterocyclyl, or $C_1$–$C_6$ alkyl, each of said $R^4$ groups being optionally substituted by 1 to 3 $R^6$ groups;

each $R^6$ is independently selected from $R^5$, $C_1$–$C_6$ alkyl, $C_2$–$C_{10}$ alkenyl, $C_2$–$C_{10}$ alkynyl and —$(CH_2)_t(C_6$–$C_{10}$ aryl) optionally substituted with 1 to 3 $R^{10}$ groups, t being an integer from 0 through 3;

each $R^5$ is independently selected from halo, $C_1$–$C_6$ alkyl substituted by 1 to 3 halo, nitro, cyano, —$OR^9$, —$C(O)R^9$, —$SR^9$, —$SO_2R^9$, —$SO_3H$, —$S(O)R^7$ —$NR^7R^8$, —$C(O)OR^9$, —$OC(O)R^9$, —$SO_2NR^9R^8$, —$C(O)NR^9R^8$, —$NR^8C(O)R^9$, —$OC(O)NR^9R^8$, —$C(O)ONR^7R^9$, —$NR^8C(O)NR^9R^8$, —$NR^8C(O)O(C_1$–$C_4$ alkyl), —$C(NR^8)NR^9R^8$, —$C(NCN)NR^9R^8$, —$C(NCN)S(C_1$–$C_4$ alkyl or $C_1$–$C_4$ haloalkyl), —$NR^8C(NCN)S(C_1$–$C_4$ alkyl or $C_1$–$C_4$ haloalkyl), —$NR^8C(NCN)NR^7R^8$, —$NR^8SO_2(C_1$–$C_4$ alkyl or $C_1$–$C_4$ haloalkyl), —$NR^8C(O)C(O)R^8$, —$NR^8C(O)C(O)NR^9R^8$, —$P(O)(OR^7)_2$, and —$(CH_2)_q$(4–10 membered heterocyclyl), q is an integer from 0 through 3, and the alkyl and heterocyclyl moieties of the foregoing $R^5$ groups are optionally substituted by 1 to 3 $R^{10}$ groups;

each $R^7$ is independently hydrogen or $C_1$–$C_4$ alkyl optionally substituted by 1 to 3 halo;

each $R^8$ is independently $R^7$ or —$OR^7$;

each $R^9$ is independently selected from hydrogen, $C_1$–$C_6$ alkyl, —$(CH_2)_q(C_6$–$C_{10}$ aryl), and —$(CH_2)_q$(4–10 membered heterocyclyl), said $R^9$ groups, except H, are optionally substituted with 1 to 3 $R^{10}$ groups, and each q is independently an integer from 0 through 3; and, each $R^{10}$ is independently selected from halo, nitro, cyano, $C_1$–$C_6$ alkyl, $C_1$–$C_6$ haloalkyl, $C_1$–$C_6$ alkoxy, $C_1$–$C_6$ haloalkoxy, —$C(O)O(C_1$–$C_6$ alkyl), and $C_6$–$C_{10}$ aryl;

with the proviso that $R^1$ and $R^2$ are not both simultaneously $C_1$–$C_{10}$ alkyl.

Compounds of Formula Ic are a subset of compounds of Formula I. In addition to their use described herein in inhibiting farnesyl protein transferase activity, compounds of Formula Ic are useful as intermediates for synthesizing further compounds encompassed by Formula I.

This invention also relates to a method of inhibiting the abnormal growth of cells in a mammal, including a human, comprising administering to said mammal an amount of a compound of the Formula I, as defined above, or a pharmaceutically acceptable salt thereof, that is effective in inhibiting farnesyl protein transferase.

This invention also relates to a method of inhibiting the abnormal growth of cells in a mammal, including a human, comprising administering to said mammal an amount of a compound of the Formula I, as defined above, or a pharmaceutically acceptable salt thereof, that is effective in inhibiting abnormal cell growth.

This invention also relates to a pharmaceutical composition for inhibiting the abnormal growth of cells in a mammal, including a human, comprising an amount of a compound of the Formula I, as defined above, or a pharmaceutically acceptable salt thereof, that is effective in inhibiting farnesyl protein transferase, and a pharmaceutically acceptable carrier.

This invention also relates to a pharmaceutical composition for inhibiting the abnormal growth of cells in a mammal, including a human, comprising an amount of a compound of Formula I, as defined above, or a pharmaceutically acceptable salt thereof, that is effective in inhibiting abnormal cell growth, and a pharmaceutically acceptable carrier.

This invention also provides a method for inhibiting abnormal cell growth in a mammal which comprises administering to said mammal an amount of a compound according to Formula I and an amount of an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, and anti-hormones, wherein the amount of said anti-tumor agent is, in combination with the amount of the compound of Formula I, effective to inhibit abnormal cell growth in the mammal.

This invention further provides a pharmaceutical composition for inhibiting abnormal cell growth in a mammal which comprises an amount of a compound of Formula l; an amount of an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, and anti-hormones; and a pharmaceutically acceptable carrier; wherein the amount of said anti-tumor agent is, in combination with the amount of the compound of Formula I, effective to inhibit abnormal cell growth in a mammal.

The phrase "abnormal cell growth", as used herein, unless otherwise indicated, refers to cell growth that is independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative disorders in which aberrant Ras activation occurs. "Abnormal cell growth"

further includes any unregulated cell growth caused by farnesyl protein transferase activity.

Examples of benign proliferative diseases include, but are not limited to, psoriasis, benign prostatic hypertrophy and restenosis.

The term "halo", as used herein, unless otherwise indicated, means fluoro, chloro, bromo or iodo. Preferred halo groups are fluoro, chloro and bromo.

The term "alkyl", as used herein, unless otherwise indicated, means straight, cyclic, and branched monovalent hydrocarbon radicals. For example, a $C_1$–$C_6$ alkyl includes, but is not limited to, an n-butyl radical and a tert-butyl radical. It is understood that for cyclic moieties at least 3 carbon atoms must be present in said alkyl group.

The term "alkenyl", as used herein, unless otherwise indicated, means straight and branched monovalent hydrocarbon radicals which comprise at least one carbon-carbon double bond. It is understood that at least two carbon atoms must be present for each carbon-carbon double bond in such moieties.

The term "alkynyl", as used herein, unless otherwise indicated, means straight and branched monovalent hydrocarbon radicals which comprise at least one carbon-carbon triple bond. It is understood that at least two carbon atoms must be present for each carbon-carbon triple bond in such moieties.

The term "cycloalkyl", as used herein, unless otherwise indicated includes saturated cyclic alkyl groups as well as cyclic alkyl groups comprising one or more points of unsaturation, i.e. one or more carbon-carbon double bonds.

The term "alkylene", as used herein, unless otherwise indicated, means divalent hydrocarbon radicals which are straight or branched.

The term "haloalky", as used herein, unless otherwise indicated, means alkyl groups, wherein "alkyl" is as defined above, substituted with one or more halo groups, on one or more carbon atoms. Preferably, the haloalkyl comprises 1 to 3 halo groups, such as a hydrocarbon comprising a trifluoromethyl or a trichloromethyl group, or a monohalosubstituted hydrocarbon.

The term "alkoxy", as used herein, unless otherwise indicated, means —O-alkyl groups wherein "alkyl" is as defined above.

"Haloalkoxy", as used herein, unless otherwise indicated, means an —O-haloalkyl group wherein "haloalky" is as defined above.

The term "aryl", as used herein, unless otherwise indicated, means an organic radical derived from an aromatic hydrocarbon by removal of one hydrogen, such as phenyl, naphthyl, and fluorene.

The term "heterocyclyl", as used herein, unless otherwise indicated, means aromatic and non-aromatic heterocyclic groups (including saturated heterocyclic groups) containing one or more heteroatoms each selected from O, S and N, wherein each ring of a heterocyclic group has from 4 to 10 atoms. Non-aromatic heterocyclic groups may include rings having only 4 atoms, but aromatic heterocyclic rings must have at least 5 atoms. Heterocyclic groups of this invention unless otherwise indicated may contain one ring or more than one ring, i.e. they may be monocyclic or multicyclic, for example bicyclic (which may comprise non-aromatic and/or aromatic rings). Preferably, bicyclic heterocyclic groups of this invention contain 6–9 members in their ring systems. Monocyclic hetercyclic groups of this invention preferably contain 5 or 6 members. Examples of bicyclic heterocyclyls include, but are not limited to, non-aromatic azabicyclohexane, azabicycloheptane, and azabicyclooctane groups. Aromatic multicyclic heterocyclic groups include benzo-fused ring systems. The heterocyclic groups of this invention also include ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, piperidinyl, 1,2,3,6-tetrahydropyridinyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The terms "azacyclyl", "azacyclic group", "azabicyclyl", and the like, as used herein, unless otherwise indicated, mean a heterocyclyl group as defined above wherein at least one ring member is a nitrogen. Examples of azacyclyl groups include, but are not limited to, radicals obtainable from 1-azabicyclo[2.2.2]oct-3-ylamine, 1,8-octalactam, N-amino-3-azabicyclyclo(3,3,0)-octane, perhydroindole, azacycloheptane, 3-azabicyclo(3.2.2)nonane, 3-amino-2-oxohexamethylene-imine, azacyclooctane, 3-azabicyclo[3.1.0]hexane, 8-azabicyclo[3.2.1]octane, and 3-azabicyclo[4.1.0]heptane.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating, as "treating" is defined immediately above.

The term "pharmaceutically acceptable salt(s)", as used herein, unless otherwise indicated, includes salts of acidic or basic groups that may be present in the compounds of Formula I. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. The preparation of such salts is described below.

Certain compounds of Formula I may have asymmetric centers and therefore exist in different enantiomeric forms. All optical isomers and stereoisomers of the compounds of Formula I, and mixtures thereof, are considered to be within the scope of the invention. With respect to the compounds of Formula I, the invention includes the use of a racemate, one or more enantiomeric forms, one or more diastereomeric forms, or mixtures thereof. The compounds of Formula I may also exist as tautomers. This invention relates to the use of all such tautomers and mixtures thereof.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention and pharmaceutically acceptable salts of said compounds which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3C$ and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention can generally be prepared by carrying out the procedures disclosed in the Schemes and/or in the Examples below, by substituting a readily available isotopically labelled reagent for a non-isotopically labelled reagent.

Any patient suffering from abnormal cell growth as defined above can be treated with compounds of the Formula I according to the methods of this invention.

Patients that can be treated with compounds of the Formula I, as defined above, or pharmaceutically acceptable salts thereof, according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

Other examples of patients which may be treated with compounds of Formula I or pharmaceutically acceptable salts of such compounds according to the methods of the invention include patients suffering from benign proliferative diseases such as psoriasis, benign prostatic hypertrophy or restenosis.

DETAILED DESCRIPTION OF THE INVENTION

The compounds of Formula I are prepared as described below. In the reaction schemes and discussion that follow, $R^1$, $R^2$, $R^3$, $R^4$, $R^6$ and "m" are as defined above. The symbol "Me" in the following schemes represents a methyl group.

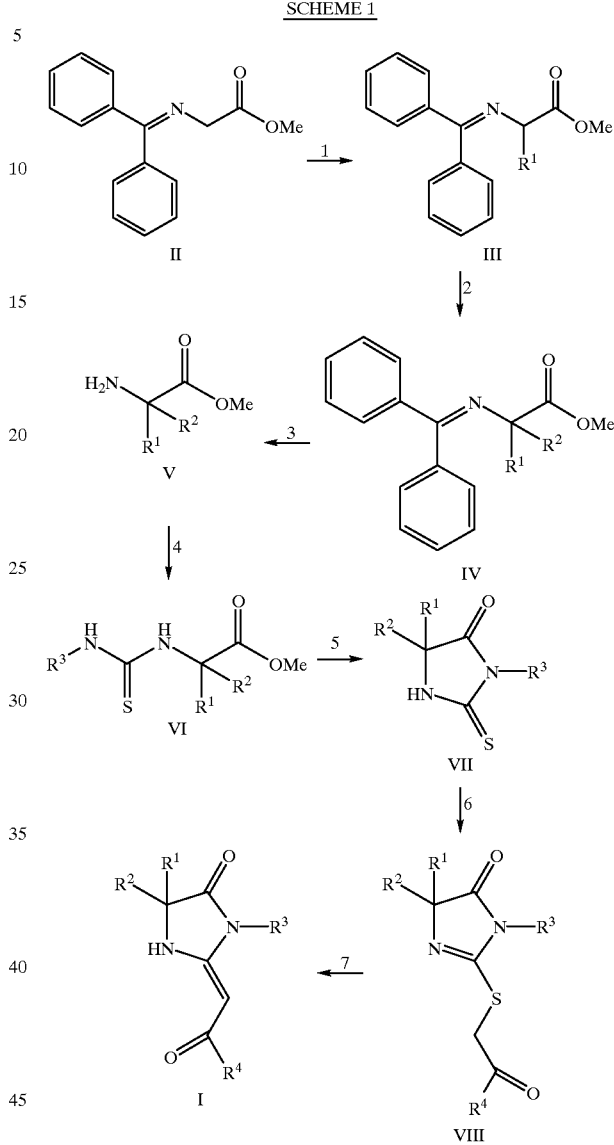

SCHEME 1

Scheme 1 illustrates the synthesis of the compounds of Formula I. In Step 1, the ester of Formula II is reacted with potassium bis(trimethylsilyl)amide in tetrahydrofuran (THF) at a temperature of about −70° C. The reaction mixture is stirred for about 30 minutes, and a compound of the formula $R^1$-X, wherein $R^1$ is as defined above and X is an appropriate leaving group, such as chloride or bromide, is then added to the reaction mixture, which is then allowed to warm to ambient temperature (20–25° C.). This results in the compound of Formula III, which can be isolated or reacted in situ to form the compound of Formula IV. In Step 2, the $R^2$ substituent, wherein $R^2$ is as defined above, is added to the compound of Formula III to provide the compound of Formula IV according to the procedure of Step 1, except that $R^2$-X is substituted for $R^1$-X.

In Step 3, the intermediate of Formula V is formed by reacting the compound of Formula IV with an acid, preferably a mineral acid such as hydrochloric, nitric or sulfuric acid, in an organic co-solvent such as ethyl ether, THF or acetonitrile, preferably THF, at a temperature ranging from about −5° C. to 35° C., preferably from about 0° C. to ambient temperature.

Steps 4 and 5 may be done as a single step or as separate steps. In general, the imidazolidine intermediate of Formula VII is formed by reacting the intermediate of Formula V with a compound of the formula $R^3$-NCS, wherein $R^3$ is as defined above. $R^3$-NCS may be synthesized by reacting $R^3$-NH$_2$ with a thiophosgene or 1,1-thiocarbonyldiimidazole (ImCSIm), in a solvent such as methylene chloride (CH$_2$Cl$_2$), and stirring the reaction mixture for approximately 12 hours. In this process, the intermediate of Formula V and $R^3$-NCS are reacted in a protic solvent, such as methanol or ethanol, preferably ethanol, at a temperature ranging from about ambient temperature to 78° C., preferably at about the reflux of the solvent. The reaction is preferably carried out for about 12 to 24 hours but this period can be longer or shorter depending on the $R^3$ substituent to be added. When $R^3$ is 1- or 2-adamantyl, it is preferable to use a large excess of the reactant $R^3$-NCS and to let the reaction proceed for a period of about two days to a week. For cases in which the intermediate of Formula VI is isolated prior to the formation of the intermediate of Formula VII, a catalytic amount of potassium cyanide is added to the reaction mixture to catalyze the formation of the intermediate of Formula VII.

In Step 6, the intermediate of Formula VII is reacted with a compound of the formula $R^4$—C(O)CH$_2$—X, wherein $R^4$ is as defined above and X is a leaving group, such as chloride or bromide, to provide the intermediate of Formula VIII. In this process, the intermediate of Formula VII is reacted with a strong base, such as sodium hydride, potassium tert-butoxide or potassium bis(trimethylsilyl)amide, preferably potassium bis(trimethylsilyl)amide, in a polar aprotic solvent such as THF, ethyl ether, dimethoxyethane (DME) or dimethylformamide (DMF), preferably THF, at a temperature ranging from about −78° C. to 35° C., preferably about 0° C. The reaction mixture is stirred for about 30 minutes, the compound of Formula $R_4$—C(O)CH$_2$—X is then added to the reaction mixture, and the mixture is then allowed to warm to ambient temperature. Alternatively, the intermediate of Formula VII is reacted with the compound of Formula $R_4$—C(O)CH$_2$—X in a polar solvent, such as THF, DMF, acetonitrile or acetone, preferably acetone, in the presence of an acid scavenger, such as carbonate or an organic tertiary amine, preferably potassium carbonate. The reaction temperature is maintained between about −78° C. to 140° C., preferably between about 0° C. to ambient temperature, to provide the intermediate of Formula VIII.

In Step 7, the compound of Formula I is formed by treating the intermediate of Formula VIII with a thiophile, such as triphenyl phosphine, tributyl phosphine or trimethylphosphite, preferably triphenyl phosphine, in a solvent such as toluene, pyridine or benzene, preferably toluene or pyridine, at a temperature ranging from about 25° C. to 120° C., preferably about 100° C.

The starting materials used in the process of Scheme 1 are either known in the literature or commercially available.

The following Schemes 2 and 3 illustrate preparation of compounds of the invention wherein $R^3$ is —(CH$_2$)$_m$(4–10 membered heterocyclyl) optionally substituted with 1 to 5 $R^6$ groups or, said heterocyclyl being an azacyclic group as defined above, wherein a hetero-nitrogen of the azacyclic group is singly-bonded to all adjacent atoms and is either unsubstituted or substituted by an $R^6$ group:

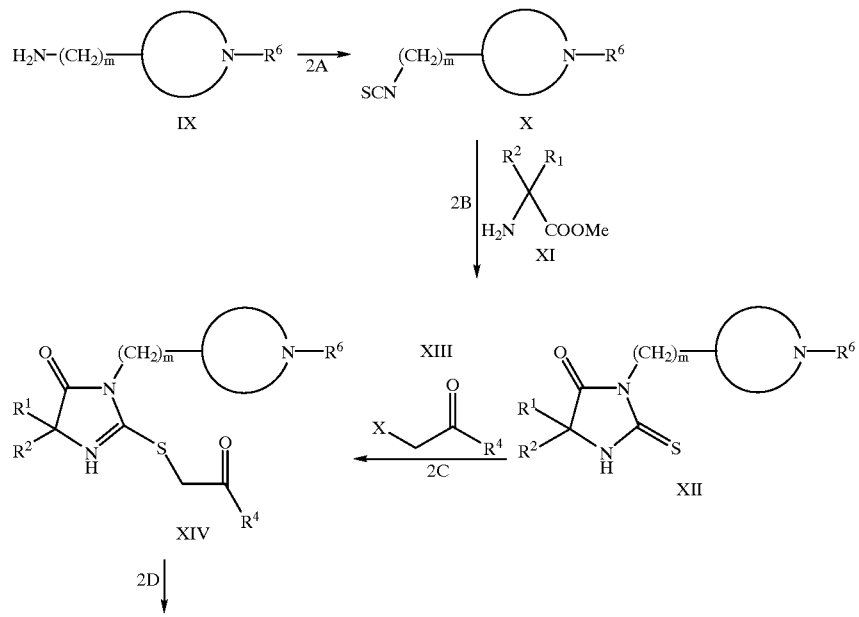

SCHEME 2

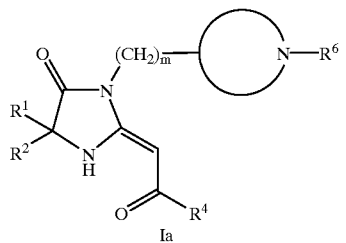
SCHEME 3
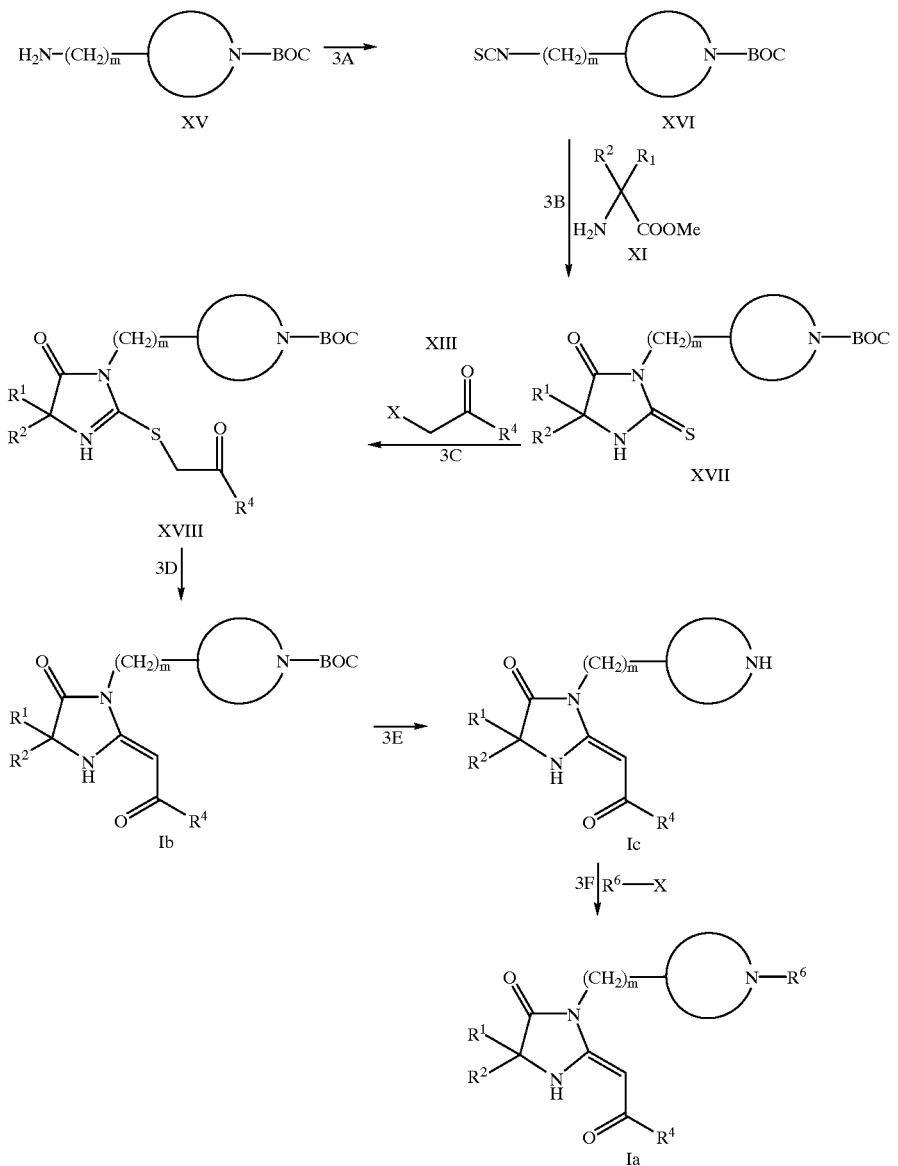
Schemes 2 and 3 are basically variations of Scheme 1. In Schemes 2 and 3,

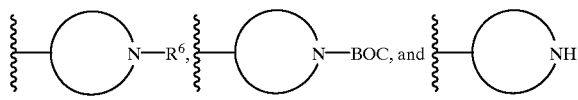

represent 4–10 membered heteroazacyclyl groups as described above, wherein N is singly bonded to all atoms which are adjacent to it and wherein $R^6$ is as described above. The symbol "BOC" represents a t-butyloxycarbonyl group.

In Step 2A of Scheme 2, $R^3$-SCN (Formula X) is prepared by reacting $R^3$-$NH_2$ (Formula IX) with a thiophosgene 1,1-thiocarbonyldiimidazole, in a solvent such as methylene chloride, the reaction mixture being stirred for a period of about 12 hours.

Step 2B corresponds to Steps 4 and 5 of Scheme 1. The starting material of Formula XI may be synthesized according to Steps 1 through 3 of Scheme 1. Starting material Formula XI is reacted with the intermediate of Formula X in a protic solvent, such as methonol or ethanol, preferably ethanol, at a temperature ranging from about ambient temperature to about 78° C., preferably at about the reflux of the solvent.

Step 2C corresponds to Step 6 of Scheme 1. The intermediate of Formula XII is reacted with a strong base in a polar aprotic solvent at a temperature of from about −78° C. to about 35° C. and stirred for about 30 minutes. A compound of Formula XIII, wherein X is a leaving group such as chloride or bromide, is then added and the reaction mixture allowed to warm to ambient temperature. Alternatively, the intermediate of Formula XII is reacted with a compound of Formula XIII in a polar solvent in the presence of an add scavenger, the reaction temperature being maintained between about −78° C. to about 140° C.

Step 2D corresponds to Step 7 of Scheme 1. The intermediate of Formula XIV is treated with a thiophile, such as triphenyl phosphine, tributyl phosphine or trimethylphosphite, in a solvent such as tolune or benzene, at a temperature ranging from about 25° C. to about 120° C., forming compounds of the invention of Formula Ia.

Step 3A of Scheme 3 is the same as Step 2A of Scheme 2. Steps 3B, 3C, and 3D, are the same as Steps 2B, 2C, and 2D of Scheme 2, respectively. Step 2D results in the formation of a compound of Formula 1b of the invention.

In Step 3E, the t-butyloxycarbonyl group of the compound of Formula 1b is removed by adding TFA (trifluoroacetic acid) to the compound of Formula 1b in a solvent such as methylene chloride, thus forming a compound of Formula 1c of the invention.

In Step 3F, the hetero-nitrogen of the $R^3$ group of a compound of Formula 1c is substituted by an $R^6$ group by methods known in the art, resulting in a compound of Formula 1a of the invention. In one process, a compound of Formula 1c is reacted with a compound $R^6$-X, wherein X is a leaving group such as chloride or bromide and $R^6$ is as described above, in a polar solvent such as THF or methylene chloride, in the presence of an acid scavenger, such as a carbonate such as sodium bicarbonate or an organic tertiary amine such as dimethylaminopyridine. The reaction temperature is maintained between about −78° C. to 140° C., preferably between about 0° C. to ambient temperature.

The compounds of Formula I that are basic in nature are capable of forming a wide variety of different salts with various inorganic and organic acids. Although such salts must be pharmaceutically acceptable for administration to animals, it is often desirable in practice to initially isolate the compound of Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Cationic salts of the compounds of Formula I are similarly prepared except through reaction of a carboxy group, such as where $R^5$ is carboxy, with an appropriate cationic salt reagent such as sodium, potassium, calcium, magnesium, ammonium, N,N'-dibenzylethylenediamine, N-methylglucamine (meglumine), ethanolamine, tromethamine, or diethanolamine.

The compounds of Formula I and their pharmaceutically acceptable salts (hereinafter referred to, collectively, as "the therapeutic compounds") can be administered orally, transdermally (e.g., through the use of a patch), parenterally or topically. Oral administration is preferred. In general, compounds of the Formula I and their pharmaceutically acceptable salts are most desirably administered in dosages ranging from about 1.0 mg up to about 1000 mg per day, preferably from about 1 to about 500 mg per day in single or divided (i.e., multiple) doses. Compounds of the Formula I and their pharmaceutically acceptable salts will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect. Larger doses are preferably divided into several small doses for administration throughout the day.

The compounds of Formula I can also be administered in combination with an amount of an anti-tumor agent, wherein the amount of said anti-tumor agent is, in combination with the amount of the compound of Formula I, effective to inhibit abnormal cell growth in the mammal. An amount of an anti-tumor agent useful in the present invention can be determined by a person of ordinary skill in the art. For example, an amount of a particular anti-tumor agent can be based on amounts already known to be useful for that anti-tumor agent. This amount can be adjusted, for example reduced, after combining with a compound of Formula I and testing for abnormal cell-growth inhibition in laboratory animals using known techniques. Anti-tumor agents are known in the art and include mitotic inhibitors, alkylating agents, anti-metabolites, intercalating antibiotics, growth factor inhibitors, cell cycle inhibitors, enzymes, topoisomerase inhibitors, biological response modifiers, and anti-hormones, as examples.

The therapeutic compounds may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored. For oral administration, tablets containing various excipients such as microcrystalline cellulose, sodium ditrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art.

Additionally, it is also possible to administer the therapeutic compounds topically and this may preferably be done by way of creams, jellies, gels, pastes, ointments and the like, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The compounds of Formula I exhibit activity as Ras farnesylation inhibitors and are useful in the treatment of cancer and the inhibition of abnormal cell growth in mammals, including humans. The activity of the compounds of Formula I as Ras farnesylation inhibitors may be determined by their ability, relative to a control, to inhibit Ras farnesyl transferase in vitro. An example of one such procedure is described below.

A crude preparation of human farnesyl transferase (FTase) comprising the cytosolic fraction of homogenized brain tissue is used for screening compounds in a 96-well assay format. The cytosolic fraction is prepared by homogenizing approximately 40 grams fresh tissue in 100 ml of sucrose/$MgCl_2$/EDTA buffer (using a Dounce homogenizer; 10–15 strokes), centrifuging the homogenates at 1000 grams for 10 minutes at 4G, re-centrifuging the supernatant at 17,000 grams for 15 minutes at 4G, and then collecting the resulting supernatant. This supernatant is diluted to contain a final concentration of 50 mM Tris HCl (pH 7.5), 5 mN DTT, 0.2 M KCl, 20 mM $ZnCl_2$, 1 mM PMSF and re-centrifuged at 178,000 grams for 90 minutes at 4G. The supernatant, termed "crude FTase" was assayed for protein concentration, aliquoted, and stored at −70° C.

The assay used to measure in vitro inhibition of human FTase is a modification of the method described by Amersham LifeScience for using their Farnesyl transferase (3H) Scintillation Proximity Assay (SPA) kit (TRKQ 7010). FTase enzyme activity is determined in a volume of 100 ml containing 50 mM N-(2-hydroxy ethyl) piperazine-N-(2-ethane sulfonic acid) (HEPES), pH 7.5, 30 mM $MgCl_2$, 20 uM KCl, 5 mM $Na_2HPO_4$, 5 mM dithiothreitol (DTT), 0.01% Triton X-100, 5% dimethyl sulfoxide (DMSO), 20 mg of crude FTase, 0.12 mM [3H]-farnesyl pyrophosphate ([3H]-FPP; 36000 dpm/pmole, Amersham LifeScience), and 0.2 mM of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 10 ml of steptavidin-coated SPA beads (TRKQ 7010) per well and incubating the reaction mixture for 30 minutes at room temperature. The amount of radioactivity bound to the SPA beads is determined using a MicroBeta 1450 plate counter. Under these assay conditions, the enzyme activity is linear with respect to the concentrations of the prenyl group acceptor, Bt-KTKCVIS, and crude FTase, and inhibition of Bt-KTKCVIS interaction with FTase can be detected. The enzyme activity is saturating with respect to the prenyl donor, FPP. The assay reaction time is also in the linear range.

The test compounds are routinely dissolved in 100% DMSO. Inhibition of farnesyl transferase activity is determined by calculating percent incorporation of tritiated-farnesyl in the presence of the test compound versus its incorporation in control wells (absence of inhibitor). $IC_{50}$ values, that is, the concentration required to produce half maximal farnesylation of Bt-KTKCVIS, is determined from the dose-responses obtained.

The following examples are provided to illustrate aspects of the subject invention. They are not intended, nor should they be construed, to limit the invention as more fully described herein and set forth in the claims. In the following examples, "DMF" means dimethylformamide and "THF" means tetrahydrofuran. "Et" represents an ethyl moiety; hence "OEt" means ethoxyl, "$Et_2O$" means diethylether, "EtOH" means ethanol, and "$NEt_3$" means triethylamine.

EXAMPLE 1

4-{[1-(1α,5α,6α-3-Benzenesulfonyl-3-aza-bicyclo [3.1.0]hex-6-yl)-5-oxo-4,4-bis-pyridin-4-ylmethyl-imidazolidin-2-ylidene]-acetyl}-benzonitrile 1A. 1α,5α,6α-3-Benzenesulfonyl-6-isothiocyanato-3-aza-bicyclo[3.1.0]hexane To a solution of 3-benzenesulfonyl-3-aza-bicyclo[3.1.0] hex-6-ylamine (476 mg, 2.00 mmol) in methylene chloride (10 ml) was added 1,1-thiocarbonyldiimidazole (350 mg, 2.00 mmol). The reaction mixture was stirred overnight and was subsequently taken into water and $CH_2Cl_2$. After separation, the organic layer was washed with brine, dried over magnesium sulfate and concentrated to afford the crude title compound of 1A.

1B. 3-(1α,5α,6α-3-Benzenesulfonyl-3-aza-bicyclo[3.1.0]hex-6-yl)-5,5-bis-pyridin-4-ylmethyl-2-thioxo-imidazolidin-4-one To the crude title compiund of 1A (2 mmol) in absolute ethanol (5 ml) was added a solution of 2-amino-3-pyridin-4-yl-2-pyridin-4-ylmethyl-propionic acid methyl ester (200 mg, 0.73 mmol) in absolute ethanol (5 ml). The reaction mixture was heated to reflux overnight under an atmosphere of dry $N_2$. It was then poured into 10% $K_2CO_3$ aqueous solution and extracted with $CH_2Cl_2$. The organic layer was washed with brine, dried over $MgSO_4$ and concentrated to afford the crude title compound of 1B (390 mg, 0.73 mmol).

Cl-MS: m/e 520.2 [M+1]

1C. 4-{[1-(1α,5α,6α-3-Benzenesulfonyl-3-aza-bicyclo[3.1.0]hex-6-yl)-5-oxo-4,4-bis-pyridin-4-ylmethyl-4,5-dihydro-1H-imidazol-2-ylsulfanyl]-acetyl}-benzonitrile The crude title compound of 1B (390 mg, ca. 0.73 mmol) was dissolved in anhydrous THF (3.0 ml) and cooled to 0° C. To the solution was added potassium bis(trimethylsilyl)-amide (165 mg, 0.83 mmol). After stirring for 15 minutes, 4-cyanophenacyl bromide (185 mg, 0.83 mmol) was added and the reaction was stirred at 0° C. for another 30 minutes. The mixture was subsequently partitioned between $CH_2Cl_2$ and saturated sodium bicarbonate ($NaHCO_3$) solution. The $CH_2Cl_2$ layer was washed with brine, dried over $MgSO_4$ and concentrated under vacuum to give the crude title compound of 1C as a brown solid (430 mg, 0.65 mmol, 89% yield).

Cl-MS: m/e 663.1 [M+1]

1D. 4-{[1-(1α,5α,6α-3-Benzenesulfonyl-3-aza-bicyclo[3.1.0]hex-6-yl)-5-oxo-4,4-bis-pyridin-4-ylmethyl-imidazolidin-2-ylidene]-acetyl}-benzonitrile The crude title compound of 1C (420 mg, 0.63 mmol) was dissolved in anhydrous toluene (10 ml) under an atmosphere of $N_2$. To the solution was added triphenylphosphine (665 mg, 2.53 mmol). The reaction was subsequently heated to 100° C. After stirring for 40 hours, the reaction was concentrated under vacuum and then partitioned between 0.1 N HCl and ethyl ether. The aqueous layer is washed two times with ethyl ether and subsequently basified to pH=8 with $K_2CO_3$. The product was then extracted into $CH_2Cl_2$, dried over $Na_2SO_4$, filtered and concentrated under vacuum to give the crude product. The crude product was chromatographed on silica gel with MeOH—$CHCl_3$—$NH_4OH$ (1:99:0.1) as eluents to afford the title compound of Example 1 as a white solid, 151 mg (0.24 mmol, 38% yield)

Cl-Ms: m/z 631 [M+1]

EXAMPLE 2

4-{[1-(1α, 5α,6α-3-tert-Butoxylcarbonyl-3-aza-bicyclo[3.1.0]hex-6-yl)-5-oxo-4,4-bis-pyridin-4-ylmethyl-imidazolidin-2-ylidene]-acetyl}-benzonitrile 2A. 3-(1α,5α,6α-tert-Butoxylcarbonyl)-6-isothiocyanato-3-aza-bicyclo [3.1.0]hexane To a solution of 3-(t-butoxylcarbonyl)-3-aza-bicyclo[3.1.0]hex-6-ylamine (9 g, 45.45 mmol) in methylene chloride (80 ml) was added 1,1-thiocarbonyldiimidazole (8.10 g, 45.45 mmol). The reaction mixture was stirred overnight. It was then partitioned between water and $CH_2Cl_2$. After separation, the organic layer was washed with brine, dried over magnesium sulfate and concentrated to afford the crude title compound of 2A, 10.46 g (43.58 mmol, 96% yield).

2B. 3-(1α,5α,6α-3-tert-Butoxylcarbonyl-3-aza-bicyclo[3.1.0]hex-6-yl)-5,5-bis-pyridin-4-ylmethyl-2-thioxo-imidazolidin-4-one A solution of the crude title compound of 2A (10.46 g, 43.58 mmol) and 2-amino-3-pyridin-4-yl-2-pyridin-4-ylmethyl-propionic acid methyl ester (5.91 g, 21.8 mmol) in absolute ethanol (60 ml) was heated to reflux for 16 hours. The reaction mixture was poured into 10% $K_2CO_3$ aqueous solution and extracted with $CH_2Cl_2$. The organic layer was washed with brine, dried over $Na_2SO_4$ and concentrated to afford the crude title compound of 2B.

Cl-MS: m/z 480 M+1], 380[(M-BOC)+1]

2C. 4-{[1-3(1α,5α,6α-tert-Butoxylcarbonyl)-3-aza-bicyclo-[3.1.0]hex-6-yl)-5-oxo-4,4-bis-pyridin-4-ylmethyl-4,5-dihydro-1H-imidazol-2-ylsulfanyl]-acetyl}-benzonitrile A solution of the crude title compound of 2B (21.8 mmol) in anhydrous THF (15 ml) was added to a suspension of potassium bis(trimethylsilyl)amide (5.04 g, 23.98 mmol) in THF (30 ml) at −78° C. The reaction was warmed to room temperature and stirred for 15 minutes. To the solution was added 4-cyanophenacyl bromide (5.37 g, 23.98 mmol). The mixture was stirred for 60 minutes. After quenching with water, THF was removed. The reaction mixture was subsequently partitioned between $CH_2Cl_2$ and saturated sodium bicarbonate ($NaHCO_3$) solution. The $CH_2Cl_2$ layer was dried over $MgSO_4$, filtered, and concentrated under vacuum to give the crude product as a brown solid. The crude product was chromatographed on silica gel with MeOH—$CHCl_3$—$NH_4OH$ (2:98:0.1) as eluents to afford the title compound of 2C, 11.52 g (18.52 mmol, 85% yield for two steps).

Cl-MS: rm/z 663.1 [M+1]

2D. 4-{[1-(1α,5α,6α-3-tert-Butoxylcarbonyl-3-aza-bicyclo[3.1.0]hex-6-yl)-5-oxo-4,4-bis-pyridin-4-ylmethyl-imidazolidin-2-ylidene]-acetyl}-benzonitrile A solution of the title compound of 2C (11.52 g, 18.52 mmol) and triphenylphosphine (14.6 g, 55.55 mmol) in anhydrous toluene (40 ml) was heated to reflux. After 40 hours, the reaction was concentrated under vacuum and then partitioned between 0.1 N HCl and ethyl ether. The aqueous layer was washed two times with ethyl ether and subsequently basified to pH=8 with $K_2CO_3$. The product was then extracted into $CH_2Cl_2$ dried over $MgSO_4$, filtered and concentrated under vacuum to give the crude product. The crude product was chromatographed on silica gel with MeOH—$CHCl_3$—$NH_4OH$ (2:98:0.1) as eluents to afford the title compound of Example 2 as a white solid, 8.56 g (14,48 mmol, 78.2% yield).

Cl-MS: m/z 592.1 [M+1]

EXAMPLE 3

4-{[1-(1α,5α,6α-3-Aza-bicyclo[3.1.0]hex-6-yl)-5-oxo-4,4-bis-pyridin-4-ylmethyl-imidazolidin-2-ylidene]-acetyl}-benzonitrile The title compound of Example 2 (6.79 g, 11.51 mmol) was dissolved in $CH_2Cl_2$ (5 ml). To the solution was added TFA (5 ml) dropwise at 0° C. The mixture was stirred for 16 hours at ambient temperature after which time the acid was removed. The reaction mixture was partitioned between $CH_2Cl_2$ and 10% $K_2CO_3$. The $CH_2Cl_2$ layer was washed with brine, dried over $MgSO_4$, filtered and concentrated under vacuum to give the title compound of Example 3 as a white solid, 5.13 g (10.46 mmol, 91%).

Cl-MS: m/z 374 [M+1]

EXAMPLE 4

4-{[1-1α,5α,6α-3-(4-Methoxy-benzenesulfonyl)-3-aza-bicyclo[3.1.0]hex-6-yl]-5-oxo-4,4-bis-pyridin-4-ylmethyl-imidazolidin-2-ylidene}-acetyl)-benzonitrile Using the same procedure as described in Example 1, 6-isothiocyanato-3-(4-methoxy-benzenesulfonyl)-3-aza-bicyclo[3.1.0]hexane (1.94 mmol) was used in the place of 3-benzenesulfonyl-6-isothiocyanato-3-aza-bicyclo[3.1.0]hexane. After cyclization with 2-amino-3-pyridin-4-yl-2-pyridin-ylmethyl-propionic acid methyl ester as described in 1B, sulfur-alkylation of 4-cyanophenacyl bromide in the presence of potassium bis(trimethylsilyl)amide as described in 1C and sulfur-extrusion in the presence of triphenylphosphine as described in 1D, 159.5 mg of the title compound was obtained as a white solid.

Cl-MS: m/z 661.1 [M+1]

EXAMPLE 5

1α,5α,6α-6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hexane-3-sulfonic acid dimethylamide Using the same procedure as described in Example 1, 6-isothiocyanato-3-aza-bicyclo[3.1.0]hexane-3-sulfonic acid dimethylamide (1.33 mmol) was used in the place of 3-benzenesulfonyl-6-isothiocyanato-3-aza-bicyclo[3.1.0]hexane. After cyclization with 2-amino-3-pyridin-4-yl-2-pyridin-4-ylmethyl-propionic acid methyl ester (as described in 1B), sulfur-alkylation of 4-cyanophenacyl bromide in the presence of potassium bis(trimethylsilyl)amide (as described in 1C) and sulfur-extrusion in the presence of triphenylphosphine as described in 1D), 25 mg of the title compound was obtained as a white solid.

Cl-MS: m/z [M+1]

EXAMPLE 6

4-({1-[1α,5α,6α-3-(4-Fluoro-benzenesulfonyl)-3-aza-bicyclo[3.1.0]hex-6-yl]-5-oxo-4,4-bis-pyridin-4-ylmethyl-imidazolidin-2-ylidene}-acetyl)-benzonitrile Using the same procedure as described in Example 1, 3-(4-fluorobenzenesulfonyl)-6-isothiocyanato-3-aza-bicyclo[3.1.0]hexane (2.62 mmol) was used in the place of 3-benzenesulfonyl-6-isothiocyanato-3-aza-bicyclo[3.1.0]hexane. After cyclization with 2-amino-3-pyridin-4-yl-2-pyridin-4-ylmethyl-propionic acid methyl ester (as described in 1B), sulfur-alkylation of 4-cyanophenacyl bromide in the presence of potassium bis(trimethylsilyl)amide (as described in 1C) and sulfur-extrusion in the presence of triphenylphosphine as described in 1D), 125 mg of the title compound was obtained as a white solid.

Cl-MS: m/z 649.3 [M+1]

EXAMPLE 7

4-{[5-Oxo-1-(1α,5α,6α-3-phenylmethanesulfonyl-3-aza-bicyclo[3.1.0]hex-6-yl)-4,4-bis-pyridin-4-ylmethyl-imidazolidin-2-ylidene]-acetyl}-benzonitrile Using the same procedure as described in Example 1, 6-isothiocyanato-3-phenylmethanesulfonyl-3-aza-bicyclo [3.1.0]hexane (1.80 mmol) was used in the place of 3-benzenesulfonyl-6-isothiocyanato-3-aza-bicyclo[3.1.0]hexane. After cyclization with 2-amino-3-pyridin-4-yl-2-pyridin-4-ylmethyl-propionic acid methyl ester (as described in 1B), sulfur-alkylation of 4-cyanophenacyl bromide in the presence of potassium bis(trimethylsilyl)amide (as described in 1C) and sulfur-extrusion in the presence of triphenylphosphine as described in 1D), 20 mg of the title compound was obtained as a white solid.

Cl-MS: m/z 645.2 [M+1]

EXAMPLE 8

4-{[1-(1α,5α,6α-3-(4-Chlorobenzene)sulfonyl-3-aza-bicyclo [3.1.0]hex-6-yl)-5-oxo-4,4-bis-pyridin-4-ylmethyl-imidazolidin-2-ylidene]-acetyl}-benzonitrile Using the same procedure as described in Example 1, 3-(4-chlorobenzenesulfonyl)-6-isothiocyanato-3-aza-bicyclo[3.1.0]hexane(1.48 mmol) was used in the place of 3-benzenesulfonyl-6-isothiocyanato-3-aza-bicyclo[3.1.0]hexane. After cyclization with 2-amino-3-pyridin-4-yl-2-pyridin-4-ylmethyl-propionic acid methyl ester (as described in 1B), sulfur-alkylation of 4-cyanophenacyl bromide in the presence of potassium bis(trimethylsilyl)amide (as described in 1C) and sulfur-extrusion in the presence of triphenylphosphine as described in 1D), 60 mg of the title compound was obtained as a white solid.

Cl-MS: m/z 667.4, 6654 [M+1]

EXAMPLE 9

4-({1-[1α,5α,6α-3-(Naphthalene-2-sulfonyl)3-aza-bicyclo[3.1.0]hex-6-yl-5-oxo-4,4-bis-pyridin-4ylmethyl-imidazolidin-2-ylidene]-acetyl}-benzonitrile Using the same procedure as described in Example 1, 6-isothiocyanato-3-(naphthalene-1-sulfonyl)-3-aza-bicyclo [3.1.0]hexane (1.48 mmol) was used in the place of 3-benzenesulfonyl-6-isothiocyanato-3-aza-bicyclo[3.1.0]hexane. After cyclization with 2-amino-3-pyridin-4-yl-2-pyridin-4-ylmethyl-propionic acid methyl ester (as described in 1B), sulfur-alkylation of 4-cyanophenacyl bromide in the presence of potassium bis(trimethylsilyl)amide (as described in 1C) and sulfur-extrusion in the presence of triphenylphosphine as described in 1D), 79.1 mg of the title compound was obtained as a white solid.

Cl-MS: m/z 681 [M+1]

EXAMPLE 10

4-({5-Oxo-4,4-bis-pyridin-4-ylmethyl-1-[1α.5α,6α-3-(toluene-4-sulfonyl)-3-aza-bicyclo[3.1.0]hex-6-yl]-imidazolidin-2-ylidene}-acetyl)-benzonitrile Using the same procedure as described in Example 1, 6-isothiocyanato-3-(toluene-4-sulfonyl)-3-aza-bicyclo [3.1.0]hexane (1.29 mmol) was used in the place of 3benzenesulfonyl-6-isothiocyanato-3-aza-bicyclo[3.1.0]hexane. After cyclization with 2-amino-3-pyridin-4-yl-2-pyridin-4-ylmethyl-propionic acid methyl ester (as described in 1B), sulfur-alkylation of 4-cyanophenacyl bromide in the presence of potassium bis(trimethylsilyl)amide (as described in 1C) and sulfur-extrusion in the presence of triphenylphosphine as described in 1D), 45.4 mg of the title compound was obtained as a white solid.

Cl-MS: m/z 645.2 [M+1]

EXAMPLE 11

4-({5-Oxo-4,4-bis-pyridin-4-methyl-1-[1α,5α,6α-3-(toluene-2-sulfonyl)-3-aza-bicyclo[3.1.0]hex-6-yl]-imidazolidin-2-ylidene}-acetyl)-benzonitrile Using the same procedure as described in Example 1, 6-isothiocyanato-3-(toluene-2-sulfonyl)-3-aza-bicyclo[3.1.0]hexane (0.78 mmol) was used in the place of 3-benzenesulfonyl-6-isothiocyanato-3-aza-bicyclo[3.1.0]hexane. After cyclization with 2-amino-3-pyridin-4-yl-2-pyridin-4-ylmethyl-propionic acid methyl ester as described in 1B, sulfur-alkylation of 4-cyanophenacyl bromide in the presence of potassium bis(trimethylsilyl)amide as described in 1 C and sulfur-extrusion in the presence of triphenylphosphine as described in 1D, 86.7 mg of the title compound of Example 11 was obtained as a white solid.

Cl-MS: m/z 645.3 [M+1]

EXAMPLE 12

4-({5-Oxo-1-[1α,5α,6α-3-(piperidine-1-sulfonyl)-3-aza-bicyclo[3.1.0]hex-6-yl]-4,4-bis-pyridin-4-ylmethyl-imidazolidin-2-ylidene}-acetyl)-benzonitrile Using the same procedure as described in Example 1, 6-isothiocyanato-3-(piperidine-1-sulfonyl)-3-aza-bicyclo[3.1.0]hexane (1.55 mmol) was used in the place of 3-benzenesulfonyl-6-isothiocyanato-3-aza-bicyclo[3.1.0]hexane. After cyclization with 2-amino-3-pyridin-4-yl-2-pyridin-4-ylmethyl-propionic acid methyl ester as described in 1B, sulfur-alkylation of 4-cyanophenacyl bromide in the presence of potassium bis(trimethylsilyl)amide as described in 1C and sulfur-extrusion in the presence of triphenylphosphine as described in 1D, 140 mg of the title compound was obtained as a white solid.

Cl-MS: m/z 638 [M+1]

EXAMPLE 13

4-({1-[1α,5α,6α-3-(4-Methyl-piperazine-1-sulfonyl)-3-aza-bicyclo[3.1.0]hex-6-yl]-5-oxo-4,4-bis-pyridin-4-ylmethyl-imidazolidin-2-ylidene}-acetyl)-benzonitrile A solution of 4-methyl-piperazine-1-sulfonyl chloride (61 mg, 0.31 mmol) in $CH_2Cl_2$ (0.5 mml) was added into a solution of the title compound of Example 3, 4-{[1-(3-aza-bicyclo[3.1.0]hex-6-yl)-5-oxo-4,4-bis-pyridin-4-ylmethyl-imidazolidin-2-ylidene]-acetyl}-benzonitrile (72 mg, 0.155 mmol) and triethylamine (43 ml, 0.31 mmol) in $CH_2Cl_2$ (0.5 ml). The reaction mixture was stirred at ambient temperature overnight and was subsequently partitioned between $CH_2Cl_2$ and saturated sodium bicarbonate ($NaHCO_3$) solution. The $CH_2Cl_2$ layer was washed with brine, dried over $MgSO_4$, filtered, and concentrated under vacuum. The crude product was chromatographed on silica gel with MeOH—$CHCl_3$—$NH_4OH$ (1:99:0.1) as eluents to afford the title compound as a slightly yellow solid, 11 mg (0.017 mmol, 11% yield).,

EXAMPLE 14

4-({5-Oxo-4,4-bis-pyridin-4-ylmethyl-1-[1α,5α,6α-3-(thiophene-2-sulfonyl)-3-aza-bicyclo[3.1.0]hex-6-yl]-imidazolidin-2-ylidene}-acetyl)-benzonitrile According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl-benzonitrile (70 mg, 0.142 mmol) and 2-thionensulfonyl chloride (53 mg, 0.246 mmol) were reacted to generate the title compound (28 mg, 0.044 mmol, 31% yield).

Cl-MS: m/z 637.1 [M+1]

EXAMPLE 15

4-(1α,5α,6α-6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hexane-3-sulfonyl)-piperazine-1-carboxylic acid tert-butyl ester According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl}-benzonitrile (100 mg, 0.204 mmol) and 4-Chlorosulfonyl-piperazine-1-carboxylic acid tert-butyl ester (174 mg, 0.612 mmol) were reacted to generate the title compound (62.3 mg, 0.084 mmol, 41% yield).

Cl-MS: m/z 739.3 [M+1]

EXAMPLE 16

4-({1-[1α,5α,6α-3-(5-Bromo-thiophene-2-sulfonyl)-3-aza-bicyclo[3.1.0]hex-6-yl]-5-oxo-4,4-bis-pyridin-4-ylmethyl-imidazolidin-2-ylidene}-acetyl)-benzonitrile According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl}-benzonitrile (50 mg, 0.102 mmol) and 5-bromothiophene-2-sulfonyl chloride (40 mg, 0.153 mmol) were reacted to generate the title compound (43.2 mg, 0.060 mmol, 59% yield).

Cl-MS: m/z 716.9 [M+1]

EXAMPLE 17

4-({1-[1α,5α,6α-3-(4-Ethyl-piperazine-1-sulfonyl)-3-aza-bicyclo[3.1.0]hex-6-yl]-5-oxo-4,4-bis-pyridin-4-ylmethyl-imidazolidin-2-ylidene}-acetyl}-benzonitrile According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl}-benzonitrile (50 mg, 0.102 mmol) and 4-ethyl-piperazine-1-sulfonyl chloride (130 mg, 0.612 mmol) were reacted to generate the title compound as an off-white solid (47.8 mg, 0.072 mmol, 70% yield).

Cl-MS: m/z 667.2 [M+1]

EXAMPLE 18

4-({1-[1α,5α,6α-3-(3-Chloro-propane-1-sulfonyl)-3-aza-bicyclo[3.1.0]hex-6-yl]-5-oxo-4,4-bis-pyridin-4-ylmethyl-imidazolidin-2-ylidene}-acetyl)-benzonitrile According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl}-benzonitrile (50 mg, 0.102 mmol) and 3-chloropropanesulfonyl chloride (54.2 mg, 0.306 mmol) were reacted to generate the title compound as an off-white solid (37.9 mg, 0.060 mmol, 70% yield).

Cl-MS: m/z 631.2 [M+1]

EXAMPLE 19

4-({1-[3-(4-Methyl-piperidine-1-sulfonyl)-3-aza-bicyclo[3.1.0]hex-6-yl]-5-oxo-4,4-bis-pyridin-4-ylmethyl-imidazolidin-2-ylidene}-acetyl)-benzonitrile According to the procedure of Example 13, 4-{[1-(3-aza-bicyclo[3.1.0]hex-6-yl)-5-oxo-4,4-bis-pyridin-4-ylmethylimidazolidin-2-ylidene]-acetyl}-benzonitrile (50 mg, 0.102 mmol) and 4-methyl-piperidine-1-sulfonyl chloride (60.2 mg, 0.306 mmol) were reacted to generate the title compound as an off-white solid (62 mg, 0.095 mmol, 93% yield).

Cl-MS: m/z 652.3 [M+1]

EXAMPLE 20

1-(1α,5α,6α-6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hexane-3-sulfonyl)-piperidine-4-carboxylic acid ethyl ester According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl}-benzonitrile (50 mg, 0.102 mmol) and 1-chlorosulfonyl-piperidine-4-carboxylic acid (153 mg, 0.60 mmol) were reacted to generate the title compound as an off-white solid (10 mg, 0.014 mmol, 14% yield).

Cl-MS: m/z 597.3 [M+1]

EXAMPLE 21

4-({5-Oxo-1-[1α,5α,6α-3-(4-propyl-piperidine-1-sulfonyl)-3-aza-bicyclo[3.1.0]hex-6-yl]-4,4-bis-pyridin-4-ylmethyl-imidazolidin-2-ylidene}-acetyl)-benzonitrile According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl}-benzonitrile (50 mg, 0.102 mmol) and 4-propyl-piperidine-1-sulfonyl chloride (135 mg, 0.60 mmol) were reacted to generate the title compound as an off-white solid (40 mg mg, 0.059 mmol, 59% yield).

Cl-MS: m/z 680.3 [M+1]

EXAMPLE 22

4-({1-[1α,5α,6α-3-(2,5-Dichloro-thiophene-3-sulfonyl)-3-aza-bicyclo[3.1.0]hex-6-yl]-5-oxo-4,4-bis-pyridin-4-ylmethyl-imidazolidin-2-ylidene}-acetyl)-benzonitrile According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl}-benzonitrile (50 mg, 0.102 mmol) and 2,5-dichlorothiophen-3-sulfonyl chloride (77 mg, 0.306 mmol) were reacted to generate the title compound as an off-white solid (20 mg, 0.028 mmol, 28% yield).

Cl-MS: m/z 705.1 [M+1]

EXAMPLE 23

4-{[1-(1α,5α,6α-3-Chloromethanesulfonyl-3-aza-bicyclo[3.1.0]hex-6-yl)-5-oxo-4,4-bis-pyridin-4-ylmethyl-imidazolidin-2-ylidene]-acetyl}-benzonitrile According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl}-benzonitrile (50 mg, 0.102 mmol) and 3-chloromethanesulfonyl chloride (45.6 mg, 0.306 mmol) were reacted to generate the title compound as an off-white solid (21 mg, 0.035 mmol, 34% yield).

Cl-MS: m/z 603.1 [M+1]

EXAMPLE 24

4-({1-[1α,5α,6α-3-(4-Isopropyl-piperazine-1-sulfonyl)-3-aza-bicyclo[3.1.0]hex-6-yl]-5-oxo-4,4-bis-pyridin-4-ylmethyl-imidazolidin -2-ylidene}-acetyl)-benzonitrile According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl}-benzonitrile (100 mg, 0.204 mmol) and 4-isopropylpiperazine-1-sulfonyl chloride (169 mg, 0.754 mmol) were reacted to generate the title compound as an off-white solid (25 mg, 0.027 mmol, 13% yield).

Cl-MS: m/z 681.3 [M+1]

EXAMPLE 25

4({5-Oxo-1-[1α,5α,6α-3-(1-phenyl-1H-tetrazol-5-yl)-3-aza-bicyclo[3.1.0]hex-6-yl]-4,4-bis-pyridin-4-ylmethyl-imidazolidin-2-ylidene}-acetyl)-benzonitrile Using the same procedure as described in Example 1, 6-isothiocyanato-3-(1-phenyl-1H-tetrazol-5-yl)3-aza-bicyclo[3.1.0]hexane (0.74 mmol) was used in the place of 3-benzenesulfonyl-6-isothiocyanato-3-aza-bicyclo[3.1.0]hexane. After cyclization with 2-amino-3-pyridin-4-yl-2-pyridin-4-ylmethyl-propionic acid methyl ester (as described in 1B), sulfur-alkylation of 4-cyanophenacyl bromide in the presence of potassium bis(trimethylsilyl)amide (as described in 1C) and sulfur-extrusion in the presence of triphenylphosphine as described in 1D), 78.5 mg of the title compound was obtained as a white solid.

Cl-MS: m/z 635.2 [M+1]

EXAMPLE 26

1α,5α,6α-6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hexane-3-carboxylic acid benzyl ester To a solution of 4-{[5-oxo-4,4-bis-pyridin-4-ylmethyl-1-(3-aza-bicyclo[3.1.0]hex-6-yl)-imidazolidin-2-ylidene]-acetyl}benzonitrile (70 mg, 0.143 mmol) in THF (1 ml) was added 3 ml of 1N NaHCO$_3$ aqueous solution followed by addition of benzyl chloroformate (0.025 ml, 0.171 mmol) in THF (2ml). The mixture was stirred overnight. After removal of THF, the reaction mixture was partitioned between CH$_2$Cl$_2$ and H$_2$O. After separation, the organic layer was washed with brine, dried over Na$_2$SO$_4$ and concentrated. The crude product was chromatographed on silica gel with MeOH—CHCl$_3$—NH$_4$OH (1:99:0.1) as eluents to afford the title compound as a white solid, 33 mg (0.053 mmol, 37% yield).

Cl-MS: m/z 625.2 [M+1]

EXAMPLE 27

4-({1-[1α,5α,6α-3-(3,3-Dimethyl-butyryl)-3-aza-bicyclo[3.1.0]hex-6-yl]-5-oxo-4,4-bis-pyridin-4-ylmethyl-imidazolidin-2-ylidene}-acetyl)-benzonitrile Using the same procedure as described in Example 26, 4-{[5-oxo-4,4-bis-pyridin-4-ylmethyl-1-(3-aza-bicyclo[3.1.0]hex-6-yl)-imidazolidin-2-ylidene]-acetyl}-benzonitrile (70 mg, 0.143 mmol) and 3,3-dimethyl-butyryl chloroformate (23 mg 0.171 mmol) were reacted to generate the title compound as a white solid, 56 mg (0.095 mmol, 67% yield).

Cl-MS: m/z 589.3 [M+1]

EXAMPLE 28

4-({5-Oxo-4,4-bis-pyridin-4-ylmethyl-1-[1α,5α,6α-3-(thiophen-2-yl-acetyl)-3-aza-bicyclo[3.1.0]hex-6-yl]-imidazolidin-2-ylidene}-acetyl)-benzonitrile Using the same procedure as described in Example 26, 4-{[5-oxo-4,4-bis-pyridin-4-ylmethyl-1-(3-aza-bicyclo

[3.1.0]hex-6-yl)imidazolidin-2-ylidene]-acetyl}-benzonitrile (70 mg, 0.143 mmol) and thiophen-2-yl-acetyl chloride (23 mg 0.171 mmol) were reacted to generate the title compound as a white solid, 56 mg (0.095 mmol, 67% yield).

Cl-MS: m/z 589.3 [M+1]

EXAMPLE 29

1α,5α,6α-(6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hex-3-yl)-phosphonic acid diethyl ester To a solution of 4-{[5-oxo-4,4-bis-pyridin-4-ylmethyl-1-(3-aza-bicyclo[3.1.0]hex-6-yl)-imidazolidin-2-ylidene]-acetyl}-benzonitrile (200 mg, 0.408 mmol) in $CH_2Cl_2$ (2.5 ml) was added 4-dimethylaminopyridine (150 mg, 1.224 mmol) followed by addition of diethyl chlorophosphate (141 mg, 0.816 mmol) at 0° C. The mixture was stirred for 1 h at ambient temperature. The reaction mixture was partitioned between $CH_2Cl_2$ and $H_2O$. After separation, the organic layer was washed with $CuSO_4$ solution, brine, dried over $Na_2SO_4$ and concentrated. The crude product was chromatographed on silica gel with $MeOH-CHCl_3-NH_4OH$ (2:98:0.2) as eluents to afford the title compound as a white solid, 169.6 mg (0.27 mmol, 66% yield).

Cl-MS: m/z 627.1 [M+1]

EXAMPLE 30

1α,5α,6α-6-{4-Allyl-2-[2-(4-cyano-phenyl)-2-oxo-ethylidene]-5-oxo-4-pyridin-4-ylmethyl-imidazolidin-1-yl}-3-aza-bicyclo[3.1.0]hexane-3-carboxylic acid tert-butyl ester 30A. 6-(4-Allyl-5-oxo-4-pyridin-4-ylmethyl-2-thioxo-imidazolidin-1-yl)-3-aza-bicyclo[3.1.0]hexane-3-carboxylic acid tert-butyl ester Using the same procedure as described in Example 2B, 3-(tert-butoxylcarbonyl)-6-isothiocyanato-3-aza-bicyclo[3.1.0]hexane (23.4 mmol, prepared in 1A) and 2-amino-2-allyl-3-pyridin-4-yl-propionic acid methyl ester (11.6 mmol) were reacted to afford the title compound of 30A (4.37 g, 10.2 mmol, 88% yield).

Cl-MS: m/z 480 [M+1],380 [(M−BOC)+1]

30B. 6-{4-Allyl-2-[2-(4-cyano-phenyl)-2-oxo-ethylsulfanyl]-5-oxo-4-pyridin-4-ylmethyl-4,5-dihydro-imidazol-1-yl}-3-aza-bicyclo[3.1.0]hexane-3-carboxylic acid tert-butyl ester Using the same procedure as described in Example 2C, the reaction of the title compound of 30A (10.3 mmol) and 4-cyanophenacyl bromide (11.3 mmol) in the presence of potassium bis(trimethylsilyl)amide (11.3 mmol) generated the title compound of 30B, 4.82 g (8.4 mmol, 84% yield).

30C. 6-{4-Allyl-2-[2-(4-cyano-phenyl)-2-oxo-ethylidene]-5-oxo-4-pyridin-4-ylmethyl-imidazolidin-1-yl}-3-aza-bicyclo[3.1.0]hexane-3-carboxylic acid tert-butyl ester Using the same procedure as described in Example 2D, the reaction of the title compound of 30B and triphenylphosphine in reflux toluene generated the title compound of example 30, 2.97 g (5.95 mmol, 71% yield).

Cl-MS: m/z 540.1 [M+1]

EXAMPLE 31

4-{[4-Allyl-1-(1α,5α,6α-3-benzenesulfonyl-3-aza-bicyclo[3.1.0]hex-6-yl)-5-oxo-4-pyridin-4-ylmethyl-imidazolidin-2-ylidene]-acetyl}-benzonitrile 31A. 4-{[1[-(3-aza-bicyclo[3.1.0]hex-6-yl)-5-oxo-4-allyl-4-pyridin-4-ylmethyl-imidazolidin-2-ylidene]-acetyl}-benzonitrile Using the same procedure as described in Example 3, the title compound of Example 30 (3.07 g, 5.70 mmol) was treated with TFA (5 ml) in $CH_2Cl_2$ to give the title compound of 31A, 2.17 g (4.94 mmol, 87%).

Cl-MS: m/z 440.2 [M+1]

31B. 4-{[4-Allyl-1-(1α,5α,6α-3-benzenesulfonyl-3-aza-bicyclo[3.1.0]hex-6-yl)-5-oxo-4-pyridin-4-ylmethyl-imidazolidin-2-ylidene]-acetyl}-benzonitrile According to the procedure of Example 13, the title compound of 31A (100 mg, 0.23 mmol) and bezenesulfonyl chloride (0.043 ml, 0.34 mmol) were reacted to generate the title compound as a white solid (65.1 mg, 0.112 mmol, 49% yield).

Cl-MS: m/z 580.2 [M+1]

EXAMPLE 32

4-{[5-Oxo-4-allyl-4-pyridin-4-ylmethyl-1-(1α,5α,6α-3-(thiophene-2-acetyl)-3-aza-bicyclo[3.1.0]hex-6-yl)-imidazolidin-2-ylidene]-acetyl}-benzonitrile According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl}-benzonitrile (100 mg, 0.23 mmol) and thiophene-2-yl-acetyl chloride (63 mg, 0.34 mmol) were reacted to generate the title compound (15 mg, 0.026 mmol, 11% yield).

Cl-MS: m/z 586.1 [M+1]

EXAMPLE 33

4-({4-Allyl-5-oxo-4-pyridin-4-ylmethyl-1-[3-(thiophene-2-sulfonyl)-3-aza-bicyclo[3.1.0]hex-6-yl]-imidazolidin-2-ylidene}-acetyl)-benzonitrile According to the procedure of Example 13, 4-{[1-(3-aza-bicyclo[3.1.0]hex-6-yl)-5-oxo-4,4-bis-pyridin-4-ylmethyl-imidazolidin-2-ylidene]-acetyl}-benzontrile (100 mg, 0.23 mmol) and 3-(thiophene-2-acetyl)sulfonyl chloride (0.04 ml, 0.34 mmol) were reacted to generate the title compound (5 mg, 0.009 mmol, 4% yield).

Cl-MS: m/z 564.2 [M+1]

EXAMPLE 34

1α,5α,6α-6-[2-[2-(4-Cyano-phenyl)-2-oxo-ethylidene]-4-(3-methyl-but-2-enyl)-5-oxo-4-pyridin-4-ylmethyl-imidazolidin-1-yl]-3-aza-bicyclo[3.1.0]hexane-3-carboxylic acid tert-butyl ester Using the same procedure as described in Example 1, 3-(tert-butoxylcarbonyl)-6-isothiocyanato-3-aza-bicyclo[3.1.0]hexane (14 mmol, prepared in 2A) was used in the place of 3-benzenesulfonyl-6-isothiocyanato-3-aza-bicyclo[3.1.0]hexane. After cyclization with 2-amino-2-(3-methyl-2-buten-1-yl)-3-pyridin-4-yl-propionic acid methyl ester (1.24 g, 5 mmol), as described in 1B, sulfur-alkylation of 4-cyanophenacyl bromide in the presence of potassium bis(trimethylsilyl)amide (as described in 1C) and sulfur-extrusion in the presence of triphenylphosphine as described in 1D), 1.53 g (2.22 mmol) of the title compound was obtained as a white solid.

Cl-MS: m/z 568.3 [M+1]

EXAMPLE 35

4-{[1-[1α,5α,6α-3-(5-Bromo-thiophene-2-sulfonyl)-3-aza-bicyclo[3.1.0]hex-6-yl]-4-(3-methyl-but-2-enyl)-5-oxo-4-pyridin-4-ylmethyl-imidazolidin-2-ylidene]-acetyl}-benzonitrile 35A. 4-{[1-(3-Aza-bicyclo[3.1.0]hex-6-yl)-4-(3-methyl-but-2-enyl)-5-oxo-4-pyridin-4-ylmethyl-imidazolidin-2-ylidene]-acetyl}-benzonitrile Using the same procedure as described in Example 3, the title compound of Example 34 (1.23 g, 2.45 mmol) was treated with TFA (2.25 ml) in CH$_2$Cl$_2$ to give the title compound of 35A (0.831 g, 1.77 mmol, 73% yield).

Cl-MS: m/z 468.2 [M+1]

35B. 4-{[1-[1α,5α,6α-3-(5-Bromo-thiophene-2-sulfonyl)-3-aza-bicyclo[3.1.0]hex-6-yl]-4-(3-methyl-but-2-enyl)-5-oxo-4-pyridin-4-ylmethyl-imidazolidin-2-ylidene]-acetyl}-benzonitrile According to the procedure of Example 13, the title compound of Example 35A (35 mg, 0.075 mmol) and 5bromo-thiophene-2-sulfonyl chloride (29 mg, 0.112 mmol) were reacted to generate the title compound as a white solid (11 mg, 0.016 mmol, 22% yield).

$^1$H NMR (CDCl$_3$): δ8.70 (br d, 2H), 8.00(d,J=8.3Hz, 2H), 7.87(d,J=4.8Hz, 2H), 7.82(d,J=8.1 Hz, 2H), 7.42(d,J=3.9Hz, 1H), 7.27(d,J=3.9Hz, 1H), 4.95(t, J=7.3 Hz, 2H), 3.74(d, J=10.0Hz, 1H), 3.70(d, J=10.0Hz, 1H), 3.47 (s, 2H), 3.29(m, 2H), 2.68 (m, 2H), 2.3 (S, 1H), 1.85 (S, 2H),1.63(s, 3H), 1.61 (s, 3H).

EXAMPLE 36

1α,5α,6α-6-{2-[2-(4-Cyano-phenyl)-2-oxo-ethylidene]-5-oxo-4-pyridin-4-ylmethyl-4-thiophen-3-ylmethyl-imidazolidin-1-yl}-3-aza-bicyclo[3.1.0]hexane-3-carboxylic acid tert-butyl ester Using the same general procedure described in Example 1, 3-(tert-butoxylcarbonyl)-6-isothiocyanato-3-aza-bicyclo[3.1.0]hexane (8.81 mmol, prepared in 2A) was used in the place of 3-benzenesulfonyl-6-isothiocyanato-3-aza-bicyclo[3.1.0]hexane. After cyclization with 2-amino-3-pyridin-4-yl-2-thiophen-3-ylmethyl-propionic acid methyl ester (0.77 g, 2.81 mmo) as described in 1B, sulfur-alkylation of 4-cyanophenacyl bromide in the presence of potassium bis(trimethylsilyl)amide as described in 1C and sulfur-extrusion in the presence of triphenylphosphine as described in 1D, 0.739 g (1.24 mmol) of the title compound was obtained.

Cl-MS: m/z 596.0 [M+1]

EXAMPLE 37

4-{[1-(1α,5α,6α-3-Benzenesulfonyl-3-aza-bicyclo[3.1.0]hex-6-yl)-5-oxo-4-pyridin-4-ylmethyl-4-thiophen-3-ylmethyl-imidazolidin-2-ylidene]-acetyl}-benzonitrile 37A. 4-{[1-(3-Aza-bicyclo[3.1.0]hex-6-yl)-5-oxo-4-pyridin-4-ylmethyl-4-thiophen-3-ylmethyl-imidazolidin-2-ylidene]-acetyl}-benzonitrile Using the same procedure as described in Example 3, the title compound of Example 36 (0.653 g, 1.10 mmol) was treated with TFA (1.10 ml) in CH$_2$Cl$_2$ to give the title compound of 37A (0.311 g, 0.63 mmol, 57% yield).

Cl-MS: m/z 496.2 [M+1].

37B. 4-{[1-(3-Benzenesulfonyl-3-aza-bicyclo[3.1.0]hex-6-yl)-5-oxo-4-pyridin-4-ylmethyl-4-thiophen-3-ylmethyl-imidazolidin-2-ylidene]-acetyl}-benzonitrile According to the procedure of Example 13, the title compound of 37A (60 mg, 0.12 mmol) and benzenesulfonyl chloride (0.023 ml, 0.18 mmol) were reacted to generate the title compound as a white solid (58 mg, 0.091 mmol, 76% yield).

Cl-MS: m/z 637.2 [M+1]

EXAMPLE 38

1α,5α,6α-6-{4-(3-Chloro-but-2-enyl)-2-[2-(4-cyano-phenyl)-2-oxo-ethylidene]-5-oxo-4-pyridin-4-ylmethyl-imidazolidin-1-yl}-3-aza-bicyclo[3.1.0]hexane-3-carboxylic acid tert-butyl ester Using the same procedure as described in Example 1, 3-(tert-butoxylcarbonyl)-6-isothiocyanato-3-aza-bicyclo[3.1.0]hexane (7.25 mmol, prepared in 2A) was used in the place of 3-benzenesulfonyl-6-isothiocyanato-3-aza-bicyclo[3.1.0]hexane. After cyclization with 2-amino-5-chloro-2-pyridin-4-ylmethyl-hex4-enoic acid methyl ester (0.5 g, 1.87 mmol), as described in 1B, sulfur-alkylation of 4-cyanophenacyl bromide in the presence of potassium bis(trimethylsilyl)amide (as described in 1C) and sulfur-extrusion in the presence of triphenylphosphine as described in 1D), 0.774 g (1.32 mmol) of the tile compound was obtained.

Cl-MS: m/z 588.1 [M+1]

EXAMPLE 39

4-{[1-[1α,5α,6α-3-(5-Bromo-thiophene-2-sulfonyl)-3-aza-bicyclo[3.1.0]hex-6-yl]-4-(3-chloro-but-2-enyl)-5-oxo-4-pyridin-4-ylmethyl-imidazolidin-2-ylidene]-acetyl}-benzonitrile 39A. 4-{[1-(3-Aza-bicyclo[3.1.0]hex-6-yl)-4-(3-chloro-but-2-enyl)-5-oxo-4-pyridin-4-ylmethyl-imidazolidin-2-ylidene]-acetyl}-benzonitrile Using the same procedure as described in Example 3, the title compound of 38 (0.774 g, 1.32 mmol) was treated with TFA (1.30 ml) in CH$_2$Cl$_2$ to give the title compound of 39A (0.527 g, 1.08 mmol, 82% yield).

Cl-MS: m/z 488.0 [M+1]

39B. 4-{[1-[3-(5-Bromo-thiophene-2-sulfonyl)-3-aza-bicyclo[3.1.0]hex-6-yl]-4-(3-chloro-but-2-enyl)-5-oxo-4-pyridin-4-ylmethyl-imidazolidin-2-ylidene]-acetyl}-benzonitrile According to the procedure of Example 13, the title compound of Example 39A (35 mg, 0.072 mmol) and 5-bromothiophene-2-sulfonyl chloride (28 mg, 0.108 mmol) were reacted to generate the title compound as a white solid (7 mg, 0.010 mmol, 14% yield).

Cl-MS: m/z 712.0, 714.0 [M+1]

EXAMPLE 40

4-{[1-(1-Benzenesulfonyl-piperidin-4-ylmethyl)-5-oxo-4,4-bis-pyridin-4-ylmethyl-imidazolidin-2-ylidene]-acetyl}-benzonitrile 40A. 4-{2-[2-(4-Cyano-phenyl)-2-oxo-ethylidene]-5-oxo-4,4-bis-pyridin-4-ylmethyl-imidazolidin-1-ylmethyl}-piperidine-1-carboxylic acid tert-butyl ester Using the same procedure as described in Example 1, 4-isothiocyanatomethyl-piperidine-1-carboxylic acid tert-butyl ester (6.04 mmol) was used in the place of 3-benzenesulfonyl-6-isothiocyanato-3-aza-bicyclo[3.1.0]hexane. After cyclization with 2-amino-3-pyridin-4-yl-2-pyridin-4-ylmethyl-propionic acid methyl ester (1.36 g, 5.03 mmol), as described in 1B, sulfur-alkylation of 4-cyanophenacyl bromide in the presence of potassium bis(trimethylsilyl)amide as described in 1C and sulfur-extrusion in the presence of triphenylphosphine as described in 1D, 1.036 g (1.78 mmol) of the title compound of 40A was obtained.

Cl-MS: m/z 607.3 [M+1]

40B. 4-[(5-Oxo-1-piperidin-4-ylmethyl-4,4-bis-pyridin-4-ylmethyl-imidazolidin-2-ylidene)-acetyl]-benzonitrile Using the same procedure as described in Example 3, the title compound of 40A (0.958 g, 1.58 mmol) was treated with TFA (3 ml) in CH$_2$Cl$_2$ to give the title compound of 40B (0.621 g, 1.23 mmol, 78% yield).

Cl-MS: m/z 488.0 [M+1].

40C. 4-{[1-(1-Benzenesulfonyl-piperidin-4-ylmethyl)-5-oxo-4,4-bis-pyridin-4-ylmethyl-imidazolidin-2-ylidene]-acetyl}benzonitrile According to the procedure of Example 13, the title compound of 40B (50 mg, 0.099 mmol) and benzenesulfonyl chloride (0.025 ml, 0.198 mmol) were reacted to generate the title compound as a white solid (25 mg, 0.037 mmol, 37% yield).

Cl-MS: m/z 677.2 [M+1]

EXAMPLE 41

4-{2-[2-(4Cyano-phenyl)-2-oxo-ethylidene]-5-oxo-4,4-bis-pyridin-4-ylmethyl-imidazolidin-1-ylmethyl}-piperidine-1-sulfonic acid dimethylamide According to the procedure of Example 13, the title compound of 40B (50 mg, 0.099 mmol) and N,N-dimethylsulfamyl chloride (0.025 ml, 0.237 mmol) were reacted to generate the title compound as a white solid (14 mg, 0.023 mmol, 19% yield).

Cl-MS: m/z 614.2 [M+1]

EXAMPLE 42

4-({5-Oxo-1-[1-(1-phenyl-1H-tetrazol-5-yl)-piperidin-4-ylmethyl]-4,4-bis-pyridin-4-ylmethyl-imidazolidin-2-ylidene}-acetyl)-benzonitrile To a solution of the title compound of 40B (100 mg, 0.20 mmol) and (1-phenyl-1H-tetrazol-5-yl chloride (50 mg, 0.30 mmol) in $CH_3CN$ (1 ml) was added $K_2CO_3$ (0.08 9, 0.06 mmol). The mixture was stirred overnight. After removal of $CH_3CN$, the reaction mixture was partitioned between $CH_2Cl_2$ and $H_2O$. After separation, the organic layer was washed with brine, dried over $Na_2SO_4$ and concentrated. The crude product was chromatographed on silica gel with MeOH—$CHCl_3$—$NH_4OH$ (1:99:0.1) as eluents to afford the title compound as a white solid, 5 mg (0.077 mmol, 4% yield).

Cl-MS: m/z 651.2 [M+1]

EXAMPLE 43

4-({1-[1-(1-Methyl-1H-imidazole-4-sulfonyl)-piperidin-4-ylmethyl]-5-oxo-4,4-bis-pyridin-4-ylmethyl-imidazolidin-2-ylidene}-acetyl)-benzonitrile According to the procedure of Example 13, the title compound of 40B (100 mg, 0.20 mmol) and 1-methylimidazol-4-ylsulfonyl chloride (50 mg, 0.30 mmol) were reacted to generate the title compound as a white solid (9 mg, 0.014 mmol, 7% yield).

Cl-MS: m/z 651.0 [M+1]

EXAMPLE 44

4-({5-Oxo-4,4-bis-pyridin-4-ylmethyl-1-[1-(thiophene-2-sulfonyl)-piperidin-4-ylmethyl]-imidazolidin-2-ylidene}-acetyl)-benzonitrile According to the procedure of Example 13, the title compound of 40B (36 mg, 0.071 mmol) and thiophene-2-sulfonyl chloride (16 mg, 0.085 mmol) were reacted to generate the title compound (9 mg, 0.014 mmol,19% yield).

Cl-MS: m/z 653.0 [M+1]

EXAMPLE 45

4-{[1-(1-Benzenesulfonyl-pyrrolidin-3-yl)-5-oxo-4,4-bis-pyridin-4-ylmethyl-imidazolidin-2-ylidene]-acetyl}-benzonitrile Using the same procedure as described in Example 1, 1-phenylsulfonylpyrrolidin-3-ylisocyanate (1.38 mmol) was used in the place of 3-benzenesulfonyl-6-isothiocyanato-3-aza-bicyclo[3.1.0]hexane. After cyclization with 2-amino-3-pyridin-4-yl-2-pyridin-4-ylmethyl-propionic acid methyl ester (1.10 mmol) as described in 1B, sulfur-alkylation of 4-cyanophenacyl bromide in the presence of potassium bis(trimethylsilyl)amide as described in 1C and sulfur-extrusion in the presence of triphenylphosphine as described in 1D, 40 mg of the title compound was obtained as a white solid.

Cl-MS: m/z 619.2 [M+1]

EXAMPLE 46

4-{[1-(1-Benzenesulfonyl-pyrrolidin-3-ylmethyl)-5-oxo-4,4-bis-pyridin4-ylmethyl-imidazolidin-2-ylidene]acetyl}-benzonitrile 46A. 4-{[5-Oxo-4,4-bis-pyridin-4-ylmethyl-1-(1-butoxycarbonyl-pyrrolidin-3-ylmethyl)-imidazolidin-2-ylidene]-acetyl}-benzonitrile Using the same procedure as described in Example 1, 3-isothiocyanatomethyl-pyrrolidine-1-carboxylic acid tert-butyl ester (21.2 mmol) was used in the place of 3-benzenesulfonyl-6-isothiocyanato-3-aza-bicyclo[3.1.0] hexane. After cyclization with 2-amino-3-pyridin-4-yl-2-pyridin-4-ylmethyl-propionic acid methyl ester (14.1 mmol), as described in 1B, sulfur-alkylation of 4-cyanophenacyl bromide in the presence of potassium bis(trimethylsilyl)amide as described in 1C and sulfur-extrusion in the presence of triphenylphosphine as described in 1D, 4.0 g (6.75 mmol) of the title compound of 46A was obtained.

Cl-MS: m/z 594.3 [M+1]

46B. 4-[(5-Oxo-4,4-bis-pyridin-4-ylmethyl-1-pyrrolidin-3-ylmethyl-imidazolidin-2-ylidene)-acetyl]-benzonitrile Using the same procedure as described in Example 3, the title compound of 46A (6.73 mmol) was treated with TFA (10 ml) in $CH_2Cl_2$ to give the title compound of 46B (2.232 g, 4.53 mmol, 78% yield).

Cl-MS: m/z 494.3 [M+1]

46C. 4-{[1-(1-Benzenesulfonyl-pyrrolidin-3-ylmethyl)-5-oxo-4,4-bis-pyridin-4-ylmethyl-imidazolidin-2-ylidene]-acetyl}-benzonitrile According to the procedure of Example 13, the title compound of 46B (100 mg, 0.20 mmol) and benzenesulfonyl chloride (0.04 ml, 0.198 mmol) were reacted to generate the title compound of Example 46 as a white solid (25 mg, 0.037 mmol, 37% yield).

Cl-MS: m/z 677.2 [M+1]

EXAMPLE 47

4-({5-Oxo-4,4-bis-pyridin-4-ylmethyl-1-[1-thiophene-2-sulfonyl)-pyrrolidin-3-ylmethyl]-imidazolidin-2-ylidene}-acetyl)-benzonitrile According to the procedure of Example 13, the title compound of 46B (70 mg, 0.14 mmol) and thiophen-2- ylsulfonyl chloride (38.4 mg, 0.21 mmol) were reacted to generate the title compound as a white solid (60 mg, 0.093 mmol, 67% yield).

Cl-MS: m/z 639.2 [M+1]

EXAMPLE 48

4-{[1α,5α,6β-1-(3-Benzenesulfonyl-3-aza-bicyclo [3.1.0]hex-6-ylmethyl)-5-oxo-4,4-bis-pyridin-4-ylmethyl-imidazolidin-2-ylidene]-acetyl}-benzonitrile Using the same procedure as described in Example 1, 1 a,5a,6b-6-isothiocyanatomethyl-3-benzenesulfonyl-3-aza-bicyclo[3.1.0]hexane (1.36 mmol) was used in the place of 3-benzenesulfonyl-6-isothiocyanato3-aza-bicyclo[3.1.0] hexane. After cyclization with 2-amino-3-pyridin-4-yl-2-pyridin-4-ylmethyl-propionic acid methyl ester (1.48 mmol) as described in 1B, sulfur-alkylation of 4-cyanophenacyl bromide in the presence of potassium bis(trimethylsilyl) amide as described in 1C and sulfur-extrusion in the presence of triphenylphosphine as described in 1D, 111 mg (0.172 mmol) of the title compound was obtained as a white solid.

$^{13}$C NMR (CDCl$_3$): δ187(s), 173.2 (s), 158.7 (s), 149.6 (d), 142.7 (s), 142.3 (s), 135.7 (s), 132.6 (d), 132.1 (d), 128.8 (d), 127.5 (d), 127.3 (d), 118.2 (s), 114.5 (s),75.6 (d), 66.7 (s), 48.9 (t), 42.5 (t), 40.5 (t), 21.4 (d), 18.0 (d).

EXAMPLE 49

4-{[1α,5α,6α-1-(3-Benzenesulfonyl-3-aza-bicyclo [3.1.0]hex-6-ylmethyl)-5-oxo-4,4-bis-pyridin-4-ylmethyl-imidazolidin-2-ylidene]-acetyl}-benzonitrile Using the same procedure as described in Example 1, 1α,5α,6α-6-isothiocyanatomethyl-3-benzenesulfonyl-3-aza-bicyclo[3.1.0]hexane (0.38 mmol) was used in the place of 3-benzenesulfonyl-6-isothiocyanato-3-aza-bicyclo[3.1.0] hexane. After cyclization with 2-amino-3-pyridin-4-yl-2-pyridin-4-ylmethyl-propionic acid methyl ester (0.42 mmol) as described in 1B, sulfur-alkylation of 4-cyanophenacyl bromide in the presence of potassium bis(trimethylsilyl) amide as described in 1C and sulfur-extrusion in the presence of triphenylphosphine as described in 1D, 16 mg (0.025 mmol) of the title compound was obtained as a white solid.

Cl-MS: m/z 645.3 [M+1]

EXAMPLE 50

4-{[1α,6α,7α-1-(3-Benzenesulfonyl-3-aza-bicyclo [4.1.0]hept-7-ylmethyl)-5-oxo-4,4-bis-pyridin-4-ylmethyl-imidazolidin-2-ylidene]-acetyl}-benzonitrile Using the same procedure as described in Example 1, 1α,6α,7α-7-isothiocyanatomethyl-3-benzenesulfonyl-3-aza-bicyclo[4.1.0]heptane (0.529 mmol) was used in the place of 3-benzenesulfonyl-6-isothiocyanato-3-aza-bicyclo [3.1.0]hexane. After cyclization with 2-amino-3-pyridin-4-yl-2-pyridin-4-ylmethyl-propionic acid methyl ester (0.635 mmol) as described in 1B, sulfur-alkylation of 4-cyanophenacyl bromide in the presence of potassium bis(trimethylsilyl)amide as described in 1C and sulfur-extrusion in the presence of triphenylphosphine as described in 1D, 10 mg (0.16 mmol) of the title compound was obtained as a white solid.

Cl-MS: m/z 658.5 [M+1]

EXAMPLE 51

4-{[1α,6α,7α-1-(3-Benzenesulfonyl-3-aza-bicyclo [4.1.0]hept-7-yl)-5-oxo-4,4-bis-pyridin-4-ylmethyl-imidazolidin-2-ylidene]-acetyl}-benzonitrile Using the same procedure as described in Example 1, 1α,6α,7α-7-isothiocyanato-3-benzenesulfonyl-3-aza-bicyclo[4.1.0]heptane (0.529 mmol) was used in the place of 3-benzenesulfonyl-6-isothiocyanato-3-aza-bicyclo[3.1.0] hexane. After cyclization with 2-amino-3-pyridin-4-yl-2-pyridin-4-ylmethyl-propionic acid methyl ester (0.635 mmol) as described in 1B, sulfur-alkylation of 4-cyanophenacyl bromide in the presence of potassium bis(trimethylsilyl)amide as described in 1C and sulfur-extrusion in the presence of triphenylphosphine as described in 1D, 10 mg (0.16 mmol) of the title compound was obtained as a white solid.

Cl-MS: m/z 658.5 [M+1]

EXAMPLE 52

4-{[1α,5α,6β-1-(3-Benzenesulfonyl-3-aza-bicyclo [3.1.0]hex-6-yl)-5-oxo-4,4-bis-pyridin-4-ylmethyl-imidazolidin-2-ylidene]-acetyl}-benzonitrile Using the same procedure as described in Example 1, 1α,5α,6β-6-isothiocyanato-3-benzenesulfonyl-3-aza-bicyclo[3.1.0]hexane (0.529 mmol) was used in the place of 3-benzenesulfonyl-6-isothiocyanato-3-aza-bicyclo[3.1.0] hexane. After cyclization with 2-amino-3-pyridin-4-yl-2-pyridin-4-ylmethyl-propionic acid methyl ester (0.635 mmol) as described in 1B, sulfur-alkylation of 4-cyanophenacyl bromide in the presence of potassium bis(trimethylsilyl)amide as described in 1C and sulfur-extrusion in the presence of triphenylphosphine as described in 1D, 10 mg (0.16 mmol) of the title compound was obtained as a white solid.

Cl-MS: m/z 658.5 [M+1]

EXAMPLE 53

4-{[1-(1α,5α,6α-3-Benzenesulfonyl-3-aza-bicyclo [3.1.0]hex-6-yl)-4,4-bis-1H-imidazol-4-ylmethyl)-5-oxo-imidazolidin-2-ylidene]-acetyl}-benzonitrile 53A. 2-(Benzylidene-amino)-3-(1-trityl-1H-imidazol-4-yl)-2-(1-trityl-1H-imidazol-4-ylmethyl)-propionic acid methyl ester A solution of potassium bis(trimethylsilyl)amide (11.34 g, 54 mmol) in THF (100 ml) was added dropwise to a mixture of (benzylidene-amino)-acetic acid methyl ester (3.83 g, 21.63 mmol) and 4-chloromethyl-1-trityl-1H-imidazole (21.6 g, 60.18 mmol) in THF (200 ml) at −78° C. The resultant solution was warmed to ambient temperature and stirred for 24 hours. After removal of THF, the reaction mixture was subsequently partitioned between ethyl acetate and brine. The aqueous layer was washed two times with ethyl acetate. The ethyl acetate extracts were combined, dried over MgSO$_4$, filtered and concentrated to give the crude title compound of 53A.

53B. 2-Amino-3-(1-trityl-1H-imidazol-4-yl)-2-(1-trityl-1H-imidazol-4-ylmethyl)-propionic acid methyl ester The crude title compound of 53A was dissolved in anhydrous THF (40 ml). To the reaction was added 10 ml of a solution of 2.0 M aqueous hydrochloric acid (HCl) at 0° C.

The mixture was stirred at ambient temperature for two hours. The reaction was subsequently concentrated under vacuum to remove the THF. The reaction was then partitioned between ethyl ether and water. The aqueous layer was washed two more times with ethyl ether. The pH of the aqueous layer was then adjusted to 9 with sodium carbonate ($Na_2CO_3$) and the solution is extracted with methylene chloride until virtually no product is left in the methylene chloride ($CH_2Cl_2$) layer. The $CH_2Cl_2$ extracts were combined, dried over $MgSO_4$, filtered and concentrated under vacuum to give the crude product. The crude product was chromatographed on silica gel with MeOH—$CHCl_3$—$NH_4OH$ (1:99:0.1) as eluents to afford the title compound of 56B as a white foam, 10.78 g (14.7 mmol, 68% yield for two steps).

53C. 3-(3-Benzenesulfonyl-3-aza-bicyclo[3.1.0]hex-6-yl)-2-thioxo-5,5-bis-(1-trityl-1H-imidazol-4-ylmethyl)-imidazolidin 4one Using the same procedure as described in Example 1B, the reaction mixture of the title compound of 53B (0.68 mmol) and 3-benzenesulfonyl-6-isothiocyanato-3-aza-bicyclo[3.1.0]hexane (6.71 mmol, prepared in 1A) was heated to reflux overnight under an atmosphere of dry $N_2$. It was then poured into 10% $K_2CO_3$ aqueous solution and extracted with $CH_2Cl_2$. The organic layer was washed with brine, dried over $MgSO_4$ and concentrated to afford the crude product. The crude product was chromatographed on silica gel with MeOH—$CHCl_3$—$NH_4OH$ (1:99:0.1) as eluents to afford the title compound of 56B as a yellow solid, 0.548 g (0.558 mmol, 82% yield).

Cl-MS: m/e 982.4 [M+1]

53D. 4-{[1-(3-Benzenesulfonyl-3-aza-bicyclo[3.1.0]hex-6-yl)-4,4-bis-(1-trityl-1H-imidazol-4-ylmethyl)-4,5-dihydro-5-oxo-1H-imidazol-2-ylsulfanyl]-acetyl}-benzonitrile Using the same procedure as described in Example 1C, the title compound of 53C (0.548 g, 0.558 mmol) and 4-cyanophenacyl bromide (138 mg, 0.614 mmol) in the presence of potassium bis(trimethylsilyl)-amide (129 mg, 0.614 mmol) reacted to yield the title compound of 53D, after chromatographic purification, 0.46 g (0.41 mmol, 73% yield).

53E. 4-{[1-(3-Benzenesulfonyl-3-aza-bicyclo[3.1.0]hex-6-yl)-4,4-bis-(1-trityl-1H-imidazol-4-ylmethyl)-5-oxo-imidazolidin-2-ylidene]-acetyl}-benzonitrile Using the same procedure as described in Example 1D, the title compound of 53D (460 mg, 0.41 mmol) and triphenylphosphine (320 mg, 1.23 mmol) in refluxed toluene yielded the title compound of 53E, after chromatographic purification, 0.324 g (0.35 mmol, 86% yield).

Cl-Ms: m/z 923.4 [M+1]

53F. 4-{[1-(3-Benzenesulfonyl-3-aza-bicyclo[3.1.0]hex-6-yl)-4,4-bis-(1H-imidazol-4-ylmethyl)-5-oxo-imidazolidin-2-ylidene]-acetyl}-benzonitrile To a solution of the title compound of 53 E (0.324 g, 0.33 mmol) in $CH_2Cl_2$ (3 ml) was added $NH_4F$ (48 mg, 1.01 mmol) and triethylsilane (021 ml, 1.30 mmol) followed by addition of 3 ml TFA. The reaction mixture was stirred at ambient temperature for 12 h. It was partitioned between $CH_2Cl_2$ and saturated sodium bicarbonate ($NaHCO_3$) solution. The $CH_2Cl_2$ layer was dried over $MgSO_4$, filtered, and concentrated under vacuum to give the crude product. The crude product was chromatographed on silica gel with MeOH—$CHCl_3$—$NH_4OH$ (6:94:0.1) as eluents to afford the title compound of example 53, 20 mg (0.033 mmol, 10% yield).

Cl-MS: m/z 609.2 [M+1]

EXAMPLE 54

4-({4,4-Bis-(1H-imidazol-4-ylmethyl)-1-[1α,5α,6α-3-(4-methyl-piperidine-1-sulfonyl)-3-aza-bicyclo[3.1.0]hex-6-yl]-5-oxo-imidazolidin-2-ylidene}-acetyl)-benzonitrile Using the same procedure as described in Example 53, 6-isothiocyanato-3-(4-methyl-piperidine-1-sulfonyl)-3-aza-bicyclo3.1.0]hexane (6.8 mmol) was used in the place of 3-benzenesulfonyl-6-isothiocyanato-3-aza-bicyclo[3.1.0]hexane. After cyclization with 2-amino-3-(1-trityl-1H-imidazol-4-yl)-2-(1-trityl-1H-imidazol-4-ylmethyl)-propionic acid methyl ester (0.68 mmol) as described in 53C, sulfur-alkylation of 4-cyanophenacyl bromide in the presence of potassium bis(trimethylsilyl)amide as described in 53D, sulfur-extrusion in the presence of triphenylphosphine as described in 53E and removal of the trityl groups as described in 53F, 4 mg (0.006 mmol) of the title compound was obtained as a white solid.

Cl-MS: m/z 630.3 [M+1]

EXAMPLE 55

4-{[1-[1α,5α,6α-3-(5-Bromo-thiophene-2-sulfonyl)-3-aza-bicyclo[3.1.0]hex-6-yl]-4,4-bis-(1H-imidazol-4-ylmethyl)-5-oxo-imidazolidin-2-ylidene]-acetyl}-benzonitrile Using the same procedure as described in Example 53, 6-isothiocyanato-3-(5-bromo-thiophene-2-sulfonyl)-3-aza-bicyclo[3.1.0]hexane (7.17 mmol) was used in the place of 3-benzenesulfonyl-6-isothiocyanato-3-aza-bicyclo[3.1.0]hexane. After cyclization with 2-amino-3-(1-trityl-1H-imidazol-4-yl)-2-(1-trityl-1H-imidazol-4-ylmethyl)-propionic acid methyl ester (0.68 mmol) as described in 53C, sulfur-alkylation of 4-cyanophenacyl bromide in the presence of potassium bis(trimethylsilyl)amide as described in 53D, sulfur-extrusion in the presence of triphenylphosphine as described in 53E and removal of the trityl groups as described in 53F, 20 mg (0.03 mmol) of the title compound was obtained as a white solid.

Cl-MS: m/z 693.1 [M+1]

EXAMPLE 56

4-{[1-(1α,5α,6α-3-Aza-3-(tert-butoxylcarbonyl)-bicyclo[3.1.0]hex-6-yl)-4,4-bis-(3-methyl-3H-imidazolylmethyl)-5-oxo-imidazolidin-2-ylidene]-acetyl}-benzonitrile 56A. 2-(Benzhydrylidene-amino)-3-(3-methyl-3H-imidazol-4-yl)-2-(3-methyl-3H-imidazol-4-ylmethyl)-propionic acid methyl ester Using the same procedure as described in 53A, the reaction of 4-chloromethyl-1-methyl-1H-imidazole (2.5 g, 12.5 mmol) and (benzhydrylidene-amino)-acetic acid methyl ester (1.056 g, 4.17 mmol) in the presence of potassium bis(trimethylsilyl)-amide (5.24g, 25.02 mmol) in THF yielded 1.40 g (3.181 mmol, 76% yield) of the title compound of 56A, after chromatographic purification.

56B. 2-Amino-3-(3-methyl-3H-imidazol-4-yl)-2-(3-methyl-3H-imidazol-4-ylmethyl)-propionic acid methyl ester Using the same procedure as described in Example 53B, the title compound of 56A (960 mg, 2.17 mmol) was treated with HCl in THF to afford the title compound of 56B, 652 mg (77% yield).

56C. 6-[4,4-Bis-3-methyl3H-imidazol-4-ylmethyl)-5-oxo-2-thioxo-imidazolidin-1-yl]-3-aza-bicyclo[3.1.0]hexane-3-carboxylic acid tert-butyl ester Using the same procedure as described in Example 1B, the reaction mixture of the title compound of 56B (0.39 g, 1.01 mmol) and 3-(tert-butoxylcarbonyl)-6-isothiocyanato-3-aza-bicyclo[3.1.0]hexane (2.53 mmol, prepared in 2A) was heated in reflux ethanol to generate 0.448 g (0.92 mmol, 92% yield) of the title compound of 56C, after chromatographic purification.

Cl-MS: m/e 486.2 [M+1]

56D. 6-[2-[2-(4-Cyano-phenyl)-2-oxo-ethylsulfanyl]-4,4-bis-3-methyl-3H-imidazol-4-ylmethyl)-5-oxo-4,5dihydro-imidazol-1-yl]-3-aza-bicyclo[3.1.0]hexane-3-carboxylic acid tert-butyl ester Using the same procedure as described in Example 1C, the title compound of 56C (0.448 g, 0.924 mmol) and 4-cyanophenacyl bromide (228 mg, 1.02 mmol) in the presence of potassium bis(trimethylsilylamide (214 mg, 1.02 mmol) reacted to yield the title compound of 56D, 0.554 g (0.882 mmol, 95% yield).

Cl-Ms: m/z 629.3 [M+1]

56E. 4-{[1-(1α,5α,6α-3-Aza-3-(tert-butoxylcarbonyl)-bicyclo[3.1.0]hex-6-yl)-4,4-bis-(3-methyl-3H-imidazol-4-ylmethyl)-5-oxo-imidazolidin-2-ylidene]-acetyl}-benzonitrile Using the same procedure as described in Example 1D, the title compound of 56D (318 mg, 0.988 mmol) and triphenylphosphine (776 mg, 2.96 mmol) in refluxed toluene yielded the title compound of Example 56, after chromatographic purification, 0.196 g (0.63 mmol, 63% yield).

Cl-Ms: m/z 597.3 [M+1]

EXAMPLE 57

4-{[1-(1α,5α,6α-3-Aza-bicyclo[3.1.0]hex-6-yl)-4,4-bis-(3-methyl-3H-imidazol-4-ylmethyl)-5-oxo-imidazolidin-2-ylidene]-acetyl}-benzonitrile Using the same procedure as described in Example 3, the title compound of 56 (196.4 mg, 0.33 mmol) was treated with TFA (0.3 ml) in $CH_2Cl_2$ to afford the title compound, 99.5 mg (0.2mmol, 61% yield).

$^1$H NMR (CDCl$_3$): δ7.87(d,J=8.3Hz, 2H), 7.70(d,=8.3Hz, 2H), 7.33(s, 2H), 6.77(s, 2H), 5.53(s, 1H), 3.56(s, 6H), 3.21(d,J=15.2Hz, 2H), 3.20(d,J=11.1Hz, 2H), 3.07(d, J=15.2Hz, 2H), 2.98(d, J=11.1Hz, 2H), 2.15(s, 1H), 1.50(s, 2H)

EXAMPLE 58

4-{[1-(1α,5α,6α-3-Benzenesulfonyl-3-aza-bicyclo[3.1.0]hex-6-yl)-4,4-bis-(3-methyl-3H-imidazol-4-ylmethyl)-5-oxo-imidazolidin-2-ylidene]-acetyl}-benzonitrile According to the procedure of Example 13, the title compound of 57, 4-{[1-(3-aza-bicyclo[3.1.0hex-6-yl)-4,4-bis-(3-methyl-3H-imidazol-ylmethyl)-5-oxo-imidazolidin-2-ylidene]-acetyl}-benzonitrile (25 mg, 0.05 mmol) and benzenesulfonyl chloride (0.0096 ml, 0.075 mmol) were reacted to generate the title compound (20 mg, 0.031 mmol, 63% yield).

Cl-MS: m/z 637.2 [M+1]

EXAMPLE 59

4-({4,4-Bis-(3-methyl-H-imidazol-4-ylmethyl)-1-[1α,5α,6α-3-(4-methyl-piperazine-1-sulfonyl)-3-aza-bicyclo[3.1.0]hex6-yl]-5-oxo-imidazolidin-2-ylidene}-acetyl)-benzonitrile According to the procedure of Example 13, the title compound of 57, 4-{[1-(3-aza-bicyclo[3.1.0]hex-6-yl)-4,4-bis-(3-methyl-3H-imidazol-4-ylmethyl)-5-oxo-imidazolidin-2-lidene]-acetyl}-benzonitrile (25 mg, 0.05 mmol) and 4-methyl-piperazine-1-sulfonyl chloride (0.05 mg, 0.25 mmol) were reacted to generate the title compound (10 mg, 0.016 mmol, 30% yield).

Cl-MS: m/z tbd [M+1]

EXAMPLE 60

4-{[1-[1α,5α,6α-3-(5-Bromo-thiophene-2-sulfonyl)-3-aza-bicyclo[3.1.0]hex-6-yl]-4,4-bis-(3-methyl-3H-imidazol-4-ylmethyl)-5-oxo-imidazolidin-2-ylidene]-acetyl}-benzonitrile According to the procedure of Example 13, the title compound of 57, 4-{[1-(3-aza-bicyclo[3.1.0]hex-6-yl)-4,4-bis-(3-methyl-3H-imidazol-4-ylmethyl)-5-oxo-imidazolidin-2-ylidene]-acetyl}-benzonitrile (25 mg, 0.05 mmol) and 5-bromo-thiophene-2-sulfonyl chloride (0.02 mg, 0.075 mmol) were reacted to generate the title compound (10 mg, 0.014 mmol, 28% yield).

Cl-MS: m/z 721.1, 723.1 [M+1]

EXAMPLE 61

3-{2-[2-(4-Cyano-phenyl)-2-oxo-ethylidene]-5-oxo-4,4-bis-pyridin -4-ylmethyl-imidazolidin-1-ylmethyl}-8α-aza-bicyclo[3.2.1]octane-8-carboxylic acid tert-butyl ester A. 3-Ethoxycarbonylmethyl-8α-aza-bicyclo[3.2.1]octane-8-carboxylic acid tert-butyl ester (8α-Aza-bicyclo[3.2.1]oct-3-yl)-acetic acid ethyl ester (2.64 g, 13.4 mmol) was dissolved in $CH_2Cl_2$ (40 mL) under an atmosphere of dry $N_2$. To this solution was added Di-tert-butyl dicarbonate (3.33 g, 15.2 mmol) and the reaction was stirred at room temperature overnight. The reaction was partitioned between $CH_2Cl_2$ and 10% $NaHSO_4$. The product was extracted into $CH_2Cl_2$, dried over $MgSO_4$, filtered and concentrated (vacuum) to give an oil. The oil was purified by flash column chromatography over silica gel (eluent: ethyl acetate/hexanes 20/80). The relevant fractions were collected and concentrated (vacuum) to give 2.32 g of the title compound.

C.I. m/z 198 [M+1–Boc]; $^1$H NMR (CDCl$_3$) δ 4.10 (m, 2 H), 4.08 (q, J=7.1 Hz, 2 H), 2.41 (m, 2 H), 2.15 (m, 3 H), 1.95 (m, 2 H), 1.64 (m, 2 H), 1.42 (s, 9 H), 1.21 (t, J=7.1 Hz, 3 H).

B. 3-Carboxymethyl-8α-aza-bicyclo[3.2.1]octane-8-carboxylic acid tert-butyl ester 3-Ethoxycarbonylmethyl-8α-aza-bicyclo[3.2.1]octane-8-carboxylic acid tert-butyl ester (2.40 g, 8.08 mmol) was dissolved in EtOH (50 mL). To the mixture was added 1.0 N NaOH (16.2 mL) and the reaction was stirred overnight at room temperature. The mixture was then concentrated (vacuum) and then partitioned between $Et_2O$ and water. The water layer was then acidified to pH=2 using 0.5 N HCl and the product was extracted into $CH_2Cl_2$, dried over $MgSO_4$, filtered and concentrated (vacuum) to give 1.13 g of the title compound.

C.I. m/z 170 [M+1–Boc]; $^1$H NMR (CDCl$_3$) δ 4.11 (m, 2 H), 2.50 (m, 2 H), 2.20 (m, 3 H), 1.97 (m, 2 H), 1.65 (m, 2 H), 1.41(s, 9 H).

C. 3-(Benzyloxycarbonylamino-methyl)-8α-aza-bicyclo [3.2.1]octane-8-carboxylic acid tert-butyl ester 3-Carboxymethyl-8α-aza-bicyclo[3.2.1]octane-8-carboxylic acid tert-butyl ester (1.13 g, 4.20 mmol) was dissolved in anhydrous toluene (40 mL) under an atmosphere of dry $N_2$. To this solution was added triethylamine (760 mL, 5.46 mmol) and diphenylphosphoryl azide (1.10 mL, 5.03 mmol). The mixture was stirred at ambient temperature for 1.5 hours after which time benzyl alcohol (520 mL, 5.03 mmol) was added. The reaction mixture was heated to 96° C. The mixture was stirred at this temperature for 3 hours after which time it was cooled to 70° C. and stirred overnight. The mixture was then cooled to room temperature and diluted with ethyl acetate. The mixture was partitioned between ethyl acetate and 0.1 N NaOH. The organic layer was dried over $MgSO_4$, filtered and concentrated (vacuum) to give 1.79 g of the title compound as a yellow oil.

C.I. m/z 275 [M+1–Boc]; $^1$H NMR (CDCl$_3$) δ 7.35 (m, 5 H), 5.09 (s, 2 H), 4.11 (m, 3 H), 3.25 (m, 2 H), 1.70–2.20 (m, 7 H), 1.42 (s, 9 H), 1.31 (m, 2 H).

D. 3-Aminomethyl-8α-aza-bicyclo[3.2.1]octane-carboxylic acid tert-butyl ester 3-(Benzyloxycarbonylamino-methyl)-8α-aza-bicyclo [3.2.1]octane-8-carboxylic acid-tert-butyl ester (1.49 g, 3.97 mmol) and 500 mL of acetic acid were dissolved in EtOH (25 mL) in a Paar bottle. To the mixture was added 148 mg of 10% palladium on carbon. The reaction vessel was placed on a Paar shaker and charged with 48 psi of hydrogen. The reaction was shaken overnight at room temperature after which time it was then filtered through celite. The celite was washed with ethanol and the combined filtrates were concentrated (vacuum) to give 732 mg of the title compound.

C.I. m/z 241 [M+1]; $^1$H NMR (CDCl$_3$) δ=4.10 (m, 4H), 3.27 (m, 2 H), 1.20–2.20 (m, 9H), 1.44 (s, 9 H).

E. 3-Isothiocyanatomethyl-8α-aza-bicyclo[3.2.1]octane-8-carboxylic acid tert-butyl ester 3-Aminomethyl-8α-aza-bicyclo[3.2.1]octane-8-carboxylic acid tert-butyl ester (725 mg, 3.02 mmol) and 1,1'-thiocarbonyldiimidazole (718 mg, 3.62 mmol) were dissolved in CH$_2$Cl$_2$ (15 mL) under an atmosphere of dry N$_2$ at room temperature. The reaction was stirred for 4 hours and then partitioned between 10% NaHSO$_4$ and CH$_2$Cl$_2$. The organic layer was washed again with 10% NaHSO$_4$ followed by water and finally saturated NaHCO$_3$. The organic layer was dried over MgSO$_4$, filtered and concentrated (vacuum) to give 822 mg of the title compound.

C.I. m/z 183 [M+1–Boc]; $^1$H NMR (CDCl$_3$) δ=4.17 (m, 2 H), 3.57 (d, J=7.1 Hz, 2 H), 1.40–2.20 (m, 7 H), 1.42 (s, 9 H), 1.20 (m, 2 H).

F. 3-(5-Oxo-4,4-bis-pyridin-4-ylmethyl-2-thioxo-imidazolidin-1-ylmethyl)-8α-aza-bicyclo[3.2.1]octane-8-carboxylic acid tert-butyl ester 3-Isothiocyanatomethyl-8α-aza-bicyclo[3.2.1]octane-8-carboxylic acid tert-butyl ester (819 mg, 3.02 mmol) and 2-amino-3-pyridin-4-yl-2-pyridin-4-ylmethyl-propionic acid methyl ester (853 mg, 3.02 mmol) were dissolved in EtOH (10 mL) under an atmosphere of dry N$_2$. The reaction was heated to 75° C. and run at this temperature for 2 days. The reaction was concentrated (vacuum) to give 1.83 g of a black residue. The residue was purified via flash coloumn chromatography over silica gel (eluent: gradient ethyl acetate to CH$_3$OH/ethyl acetate 6/94) to give 678 mg of the title compound.

C.I. m/z 522 [M+1]; $^1$H NMR (CDCl$_3$) δ=8.50 (m, 4 H), 8.20 (br s, 1 H), 7.12 (m, 4 H), 4.01 (m, 2 H), 3.50 (d, J=7.1 Hz, 2 H), 3.21 (d, J=13.1 Hz, 2 H), 3.07 (d, J=13.1 Hz, 2 H), 1.50–1.95 (m, 7 H), 1.47 (s, 9 H), 0.79 (m, 2 H).

G. 3-{2-[2-(4-Cyano-phenyl)-2-oxo-ethylsulfanyl]-5-oxo-4,4-bis-pyridin-4-ylmethyl-4,5-dihydro-imidazol-1-ylmethyl}-8α-aza-bicyclo[3.2.1]octane-8-carboxylic acid tert-butyl ester To a −78° C. solution of potassium bis(trimethylsilyl) amide (272 mg, 1.36 mmol) in anhydrous THF (15 mL) under an atmosphere of dry N$_2$ was added 3-(5-Oxo-4,4-bis-pyridin-4-ylmethyl-2-thioxo-imidazolidin-1-ylmethyl)-8α-aza-bicyclo[3.2.1]octane-8-carboxylic acid tert-butyl ester (678 mg, 1.30 mmol). The solution was warmed up to room temperature and after 15 minutes was cooled to −78° C. To this solution was added 4-cyanophenacyl bromide (305 mg, 1.36 mmol). The reaction was warmed up to room temperature and stirred for 1 hour. The mixture was partitioned between CH$_2$Cl$_2$ and saturated NaHCO$_3$. The organic layer was dried over MgSO$_4$, filtered and concentrated (vacuum) to give 1.50 g of an orange residue. The residue was purified by flash coloumn chromatography over silica gel (eluent: gradient of ethyl acetate to MeOH/ethyl acetate 5/95) to give 744 mg of the title compound.

C.I. m/z 665 [M+1]; $^1$H NMR (CDCl$_3$) δ=8.40 (m, 4 H), 8.19 (d, J=8.4 Hz, 2 H), 7.90 (d, J=8.4 Hz, 2 H), 6.96 (m, 4 H), 4.61 (s, 2 H), 3.99 (m, 2 H), 3.50 (d, J=7.1 Hz, 2 H), 3.11 (m, 2 H), 3.01 (m, 4 H), 1.50–1.95 (m, 7 H), 1.45 (s, 9 H), 0.73 (m, 2 H).

H. 3-{2-[2-(4Cyano-phenyl)-2-oxo-ethylidene]-5-oxo-4,4-bis-pyridin-4-ylmethyl-imidazolidin-1-ylmethyl}-8α-aza-bicyclo[3.2.1]octane-8-carboxylic acid tert-butyl ester 3-{2-[2-(4-Cyano-phenyl)-2-oxo-ethylsulfanyl]-5-oxo-4,4-bis-pyridin-4-ylmethyl-4,5-dihydro-imidazol-1-ylmethyl}-8α-aza-bicyclo[3.2.1]octane-8-carboxylic acid tert-butyl ester (34 mg, 0.059 mmol) was dissolved in anhydrous toluene (5.0 ml) under an atmosphere of dry N$_2$. To this solution was added triphenyl phosphine (62 mg, 0.23 mmol) and 18 mL of N-ethyldiisopropyl amine and the mixture was heated to 100° C. After stirring for 48 hours, the reaction was concentrated (vacuum) and then partitioned between 0.01 N HCl and Et$_2$O. The aqueous layer was washed two times with Et$_2$O and then basified to pH=8 with NaHCO$_3$. The product was extracted into CH$_2$Cl$_2$, dried over MgSO$_4$, filtered and concentrated (vacuum) to give a tan solid. The solid was triturated with CH$_2$Cl$_2$/hexanes to give 29 mg of the title compound as a white solid.

C.I. m/z 633 [M+1]; $^1$H NMR (CDCl$_3$) δ 10.42 (br s, 1 H), 8.46 (m, 4 H), 7.86 (d, J=8.4 Hz, 2 H), 7.71 (d, J=8.4 Hz, 2 H), 7.12 (m, 4 H), 5.10 (s, 1 H), 4.00 (m, 2 H), 3.29 (d, J=13.2 Hz, 2 H), 3.20 (m, 2 H), 3.10 (d, J=13.2Hz, 2 H), 1.95 (m, 2 H), 1.5–1.7 (m, 5 H), 1.4 (s, 9 H), 0.71 (m, 2 H).

EXAMPLE 62

4-{[1-(8α-Aza-bicyclo[3.2.1]oct-3-ylmethyl)-5-oxo-4,4-bis-pyridin-4-ylmethyl-imidazolidin-2-ylidene]-acetyl}-benzonitrile 3-{2-[2-(4-Cyano-phenyl)-2-oxo-ethylidene]-5-oxo-4,4-bis-pyridin-4-ylmethyl-imidazolidin-1-ylmethyl}-8α-aza-bicyclo[3.2.1]octane-8-carboxylic acid tert-butyl ester (713 mg, 1.12 mmol) was dissolved in 10 ml of TFA under an atmosphere of dry N$_2$. The mixture was heated to 40° C. for 10 minutes. The mixture was then concentrated (vacuum) and the residue was partitioned between CH$_2$Cl$_2$ and 0.01 N NaOH. The CH$_2$Cl$_2$ layer was dried over MgSO$_4$, filtered and concentrated (vacuum) to give 545 mg of the title compound as a tan foam.

C.I. m/z 533 [M+1]; $^1$H NMR (CDCl$_3$) δ 10.38 (br s, 1 H), 8.46 (m, 4 H), 7.88 (d, J=8.3 Hz, 2 H), 7.72 (d, J=8.3 Hz, 2 H), 7.12 (m, 4 H), 5.12 (s, 1 H), 3.05–3.36 (m, 9 H), 1.3–1.7 (m, 5 H), 0.70 (m, 2 H).

EXAMPLE 63

4-{[1-(8-Acetyl-8α-aza-bicyclo[3.2.1]oct-3-ylmethyl)-5-oxo-4,4-bis-pyridin-4-ylmethyl-imidazolidin-2-ylidene]-acetyl}-benzonitrile 4-{[1-(8α-Aza-bicyclo[3.2.1]oct-3-ylmethyl-5-oxo-4,4-bis-pyridin-4-ylmethyl-imidazolidin-2-ylidene]- acetyl}benzonitrile (54 mg, 0.10 mmol) was dissolved in 1.0 mL of CH$_2$Cl$_2$ under an atmosphere of dry N$_2$. To this solution was added NEt$_3$ (36 mL, 0.26 mmol) and acetic anhydride (24 mL, 0.26 mmol). The mixture was stirred overnight at room temperature and then partitioned between CH$_2$Cl$_2$ and saturated NaHCO$_3$. The CH$_2$Cl$_2$ layer was dried over MgSO$_4$, filtered and concentrated (under vacuum) to give 59 mg of a brown residue. The residue was triturated with CH$_2$Cl$_2$/hexanes to give 45 mg of the title compound as a white solid.

C.I. m/z 575[M+1]; $^1$H NMR (CDCl$_3$) δ 10.44 (br s, 1 H), 8.47 (m, 4 H), 7.85 (d, J=8.4 Hz, 2 H), 7.71 (d, J=8.4 Hz, 2 H), 7.15 (m, 4 H), 5.11 (s, 1 H), 4.46 (m, 1 H), 3.90 (m, 1 H), 3.00–3.36 (m, 6 H), 1.96 (s, 3 H), 0.70–1.7 (m, 9 H).

EXAMPLE 64

4-{[1-(8-Methanesulfonyl-8α-aza-bicyclo[3.2.1]oct-3-ylmethyl)-5-oxo-4,4-bis-pyridin-4-ylmethyl-imidazolidin-2-ylidene]-acetyl}-benzonitrile 4-{[1-(8α-Aza-bicyclo[3.2.1]oct-3-ylmethyl)-5-oxo-4,4-bis-pyridin-4-ylmethyl-imidazolidin-2-ylidene]-acetyl}-benzonitrile (54 mg, 0.10 mmol) was dissolved in 1.0 mL of CH$_2$Cl$_2$ under an atmosphere of dry N$_2$. To this solution was added NEt$_3$ (18 mL, 0.13 mmol) and methanesulphonyl chloride (9.5 mL, 0.13 mmol). The mixture was stirred overnight at room temperature and then partitioned between CH$_2$Cl$_2$ and saturated NaHCO$_3$. The CH$_2$Cl$_2$ layer was dried over MgSO$_4$, filtered and concentrated (under vacuum) to give 56 mg of a brown residue. The residue was triturated with CH$_2$Cl$_2$/hexanes to give 49 mg of the title compound as a white solid.

C.I. m/z 611[M+1]; $^1$H NMR (CDCl$_3$) δ 10.39 (br s, 1 H), 8.48 (m, 4 H), 7.88 (d, J=8.4 Hz, 2 H), 7.72 (d, J=8.4 Hz, 2 H), 7.16 (m, 4 H), 5.10 (s, I H), 4.03 (m, 2 H), 3.10–3.30 (m, 6 H), 2.82 (s, 3 H), 2.05 (m, 2 H), 0.70-1.80 (m, 7 H).

EXAMPLE 65

3-{2-[2-(4-Cyano-phenyl)-2-oxo-ethylidene]-5-oxo-4,4-bis-pyridin-4-ylmethyl-imidazolidin-1-ylmethyl}-8α-aza-bicyclo[3.2.1octane-8-carboxylic acid ethyl ester 4-{[1-(8α-Aza-bicyclo[3.2.1]oct-3-ylmethyl)-5-oxo-4,4-bis-pyridin-4-ylmethyl-imidazolidin-2-ylidene]-acetyl}-benzonitrile (54 mg, 0.10 mmol) was dissolved in 1.0 mL of CH$_2$Cl$_2$ under an atmosphere of dry N$_2$. To this solution was added NEt$_3$ (21 mL, 0.15 mmol) and ethyl chloroformate (12 mL, 0.12 mmol). The mixture was stirred overnight at room temperature and then partitioned between CH$_2$Cl$_2$ and NaHCO$_3$. The CH$_2$Cl$_2$ layer was dried over MgSO$_4$, filtered and concentrated in vacuo to give 87 mg of a brown residue. The residue was triturated with CH$_2$Cl$_2$/hexanes to give 54 mg of the title compound as a white solid.

C.I. m/z 605[M+1]; $^1$H NMR (CDCl$_3$) δ 10.42 (br s, 1 H), 8.45 (m, 4 H), 7.85 (d, J=8.3 Hz, 2 H), 7.70 (d, J=8.3 Hz, 2 H), 7.10 (m, 4 H), 5.10 (s, 1 H), 4.03 (m,4 H), 3.05–3.30 (m, 6 H), 2.82 (s, 3 H), 1.95 (m, 2 H), 0.70–1.70 (m, 10 H).

EXAMPLE 66

4-{[1-(8-Formyl-8α-aza-bicyclo[3.2.1]oct-3-ylmethyl)-5-oxo-4,4-bis-pyridin-4-ylmethyl-imidazolidin-2-ylidene]-acetyl}-benzonitrile 4-{[1-(8α-Aza-bicyclo[3.2.1]oct-3-ylmethyl)-5-oxo-4,4-bis-pyridin-4-ylmethyl-imidazolidin-2-ylidene]-acetyl}-benzonitrile (54 mg, 0.10 mmol) was dissolved in 1.0 mL of CH$_2$Cl$_2$ under an atmosphere of dry N$_2$. To this solution was added NEt$_3$ (28 mL, 0.20 mmol) and acetic formic anhydride (23 mL, 0.26 mmol). The mixture was stirred overnight at room temperature and then partitioned between CH$_2$Cl$_2$ and aqueous saturated bicarbonate solution. The CH$_2$Cl$_2$ layer was dried over MgSO$_4$, filtered and concentrated (under vacuum) to give 58 mg of a brown residue. The residue was triturated with CH$_2$Cl$_2$/hexanes to give 45 mg of the title compound as a tan powder.

C.I. m/z 561[M+1]; $^1$H NMR (CDCl$_3$) δ 10.40 (br s, 1 H), 8.47 (m, 4 H), 8.01 (s, 1 H), 7.89 (d, J=8.4 Hz, 2 H), 7.73 (d, J=8.4 Hz, 2 H), 7.12 (m, 4 H), 5.10 (s, 1 H), 4.40 (m, 1 H), 3.80 (m, 1 H), 3.05–3.30 (m, 6 H), 0.70–2.00 (m, 9 H).

EXAMPLE 67

3-{2-[2-(4Cyano-phenyl)-2-oxo-ethylidene]-5-oxo-4,4-bis-pyridin-4-ylmethyl-imidazolidin-1-ylmethyl}-8α-aza-bicyclo[3.2.1]octane-8-carboxylic acid methyl ester 4-{[1-(8α-Aza-bicyclo[3.2.1]oct-3-ylmethyl)-5-oxo-4,4-bis-pyridin-4-ylmethyl-imidazolidin-2-ylidene]-acetyl}-benzonitrile (54 mg, 0.10 mmol) was dissolved in 1.0 mL of CH$_2$Cl$_2$ under an atmosphere of dry N$_2$. To this solution was added NEt$_3$ (21 mL, 0.15 mmol) and methyl chloroformate (9.3 mL, 0.12 mmol). The mixture was stirred for 48 hours at room temperature and then partitioned between CH$_2$Cl$_2$ and saturated NaHCO$_3$. The CH$_2$Cl$_2$ layer was dried over MgSO$_4$, filtered and concentrated (under vacuum) to give a brown residue. The residue was triturated with CH$_2$Cl$_2$/hexanes to give 51 mg of the title compound as a white solid.

C.I. m/z 591[M+1]; $^1$H NMR (CDCl$_3$) δ 10.38 (br s, 1 H), 8.46 (m, 4 H), 7.88 (d, J=8.4 Hz, 2 H), 7.71 (d, J=8.4 Hz, 2 H), 7.13 (m, 4 H), 5.11 (s, 1 H), 3.62 (s, 3 H), 3.05–3.30 (m, 6 H), 0.70–2.00 (m, 9 H).

EXAMPLE 68

4-{[1-(8-Benzenesulfonyl-8α-aza-bicyclo[3.2.1]oct-3-ylmethyl)-5-oxo-4,4-bis-pyridin-4-ylmethyl-imidazolidin-2-ylidene]-acetyl}-benzonitrile 4-{[1-(8α-Aza-bicyclo[3.2.1]oct-3-ylmethyl)-5-oxo-4,4-bis-pyridin-4-ylmethyl-imidazolidin-2-ylidene]-acetyl}-benzonitrile (54 mg, 0.10 mmol) was dissolved in 1.0 mL of CH$_2$Cl$_2$ under an atmosphere of dry N$_2$. To this solution was added NEt$_3$ (21 mL, 0.15 mmol) and benzenesulphonyl chloride (15 mL, 0.12 mmol). The mixture was stirred overnight at room temperature and then partitioned between CH$_2$Cl$_2$ and saturated NaHCO$_3$. The CH$_2$Cl$_2$ layer was dried over MgSO$_4$, filtered and concentrated (under vacuum) to give a brown residue. The residue was triturated with CH$_2$Cl$_2$/hexanes to give 67 mg of the title compound as a white solid.

C.I. m/z 673[M+1]; $^1$H NMR (CDCl$_3$) δ 10.45 (br s, 1 H), 8.44 (m, 4 H), 7.40–7.90 (m, 9 H), 7.10 (m, 4 H), 5.09 (s, 1 H), 4.05 (m, 2 H), 3.05–3.30 (m, 6 H), 0.70–2.00 (m, 9 H).

EXAMPLE 69

3-{2-[2-(4-Cyano-phenyl)-2-oxo-ethylidene]-5-oxo-4,4-bis-pyridin-4-ylmethyl-imidazolidin-1-ylmethyl}-8α-aza-bicyclo[3.2.1]octane-8-sulfonic acid dimethylamide 4-{[1-(8α-Aza-bicyclo[3.2.1]oct-3-ylmethyl)-5-oxo-4,4-bis-pyridin-4-ylmethyl-imidazolidin-2-ylidene]-acetyl}- benzonitrile (54 mg, 0.10 mmol) was dissolved in 1.0 ml of $CH_2Cl_2$ under an atmosphere of dry $N_2$. To this solution was added $NEt_3$ (42 mL, 0.30 mmol) and dimethylsulfamoyl chloride (26 mL, 0.24 mmol). The mixture was stirred overnight at room temperature and then partitioned between $CH_2Cl_2$ and saturated $NaHCO_3$. The $CH_2Cl_2$ layer was dried over $MgSO_4$, filtered and concentrated (under vacuum) to give a brown residue. The residue was triturated with $CH_2Cl_2$/hexanes to give 72 mg of the title compound as a tan powder.

C.I. m/z 640[M+1]; $^1H$ NMR ($CDCl_3$) δ 10.40 (br s, 1 H), 8.47 (m, 4 H), 7.86 (d, J=8.3 Hz, 2 H), 7.71 (d, J=8.3Hz, 2 H), 7.13 (m, 4 H), 5.11 (s, 1 H), 3.90 (m, 2 H), 3.05–3.30 (m, 6 H), 2.71 (s, 6 H), 0.70–2.00 (m, 9 H).

EXAMPLE 70

4-{[1-(8-Ethanesulfonyl-8α-aza-bicyclo[3.2.1]oct-3-ylmethyl)-5-oxo-4,4-bis-pyridin-4-ylmethyl-imidazolidin-2-ylidene]-acetyl}-benzonitrile 4-{[1-(8α-Aza-bicyclo[3.2.1]oct-3-ylmethyl)-5-oxo-4,4-bis-pyridin-4-ylmethyl-imidazolidin-2-ylidene]-acetyl}-benzonitrile (54 mg, 0.10 mmol) was dissolved in 1.0 mL of $CH_2Cl_2$ under an atmosphere of dry $N_2$. To this solution was added $NEt_3$ (42 mL, 0.30 mmol) and ethylsulphonyl chloride (22 mL, 0.24 mmol). The mixture was stirred overnight at room temperature and then partitioned between $CH_2Cl_2$ and saturated $NaHCO_3$. The $CH_2Cl_2$ layer was dried over $MgSO_4$, filtered and concentrated (vacuum) to give a brown residue. The residue was triturated with $CH_2Cl_2$/hexanes to give 64 mg of the title compound as a tan powder.

C.I. m/z 625[M+1]; $^1H$ NMR ($CDCl_3$) δ 10.38 (br s, 1 H), 8.43 (m, 4 H), 7.88 (d, J 8.4 Hz, 2 H), 7.71 (d, J=8.4 Hz, 2 H), 7.12 (m, 4 H), 5.11 (s, 1 H), 3.98 (m, 2 H), 3.05–3.30 (m, 6 H), 2.90 (m, 2 H), 0.70–2.05 (m, 12 H).

EXAMPLE 71

4-({5-Oxo-1-[8-(propane-1-sulfonyl)-8α-aza-bicyclo[3.2.1]oct-3-ylmethyl]-4,4-bis-pyridin-4-ylmethyl-imidazolidin-2-ylidene}-acetyl)-benzonitrile 4-{[1-(8α-Aza-bicyclo[3.2.1]oct-3-ylmethyl-5-oxo-4,4-bis-pyridin-4-ylmethyl-imidazolidin-2-ylidene]-acetyl}-benzonitrile (54 mg, 0.10 mmol) was dissolved in 1.0 mL of $CH_2Cl_2$ under an atmosphere of dry $N_2$. To this solution was added $NEt_3$ (42 mL, 0.30 mmol) and propylsulphonyl chloride (28 mL, 0.24 mmol). The mixture was stirred overnight at room temperature and then partitioned between $CH_2Cl_2$ and saturated $NaHCO_3$. The $CH_2Cl_2$ layer was dried over $MgSO_4$, filtered and concentrated (vacuum) to give a brown residue. The residue was triturated with $CH_2Cl_2$/hexanes to give 47 mg of the title compound as a tan powder.

C.I. m/z 639[M+1]; $^1H$ NMR ($CDCl_3$) δ 10.40 (br s, 1 H), 8.45 (m, 4 H), 7.88 (d, J=8.4 Hz, 2 H), 7.71 (d, J=8.4 Hz, 2 H), 7.11 (m, 4 H), 5.11 (s, I H), 4.00 (m, 2 H), 3.05–3.30 (m, 6 H), 2.89 (m, 2 H), 0.70–2.05 (m, 14 H).

EXAMPLE 72

3-{2-[2-(4-Cyano-phenyl)-2-oxo-ethylidene]-5-oxo-4,4-bis-pyridin-4-ylmethyl-imidazolidin-1-ylmethyl}-8β-aza-bicyclo[3.2.1]octane-8-carboxylic acid tert-butyl ester A. 3-Oxo-aza-bicyclo[3.2.1]octane-8-carboxylic acid tert-butyl ester 8-Aza-bicyclo[3.2.1]octan-3-one (9.64 g, 77.1 mmol) was dissolved in $CH_2Cl_2$ (100 mL) under an atmosphere of dry $N_2$ at room temperature. To this solution was added Di-tert-butyl dicarbonate (20.2 g, 92.7 mmol). The reaction was stirred at room temperature for 48 hours and then partitioned between 10% $NaHSO_4$ and $CH_2Cl_2$. The $CH_2Cl_2$ layer was washed with saturated $NaHCO_3$ followed by brine. The $CH_2Cl_2$ layer was dried over $MgSO_4$, filtered and concentrated (vacuum) to give 23.1 g of the title compound as an oil.

C.I. m/z 126 [M+1–Boc]; $^1H$ NMR ($CDCl_3$) δ 4.41 (m, 2 H), 2.62 (m, 2 H), 2.32 (m, 2 H), 2.06 (m, 2 H), 1.40–1.50 (m, 11 H).

B. 3-Methylene-8-aza-bicyclo[3.2.1]octane-8-carboxylic acid tert-butyl ester

Methyltriphenylphosphonium iodide (40.0 g, 99.1 mmol) was suspended in anhydrous THF (200 mL) under an atmosphere of dry $N_2$. To this solution was added 1.0 M potassium tert-butoxide in THF (100 mL). The mixture was stirred for 30 minutes. A solution of 3-Oxo-8-aza-bicyclo[3.2.1]octane-8-carboxylic acid tert-butyl ester (14.9 g, 66.0 mmol) in anhydrous THF (100 mL) was added to the mixture which was then stirred overnight. The mixture was concentrated (vacuum) and the resulting residue taken up in ethyl acetate/hexanes (10/90). The solution was filtered and the filtrate was concentrated (vacuum) to give 27.1 g of a brown oil which was subsequently purified using flash coloumn chromatography over silica gel (eluent: gradient from ethyl acetate/hexanes 1/99 to ethyl acetate/hexanes 20/80) to give 9.50 g of the title compound as an oil.

C.I. m/z 124 [M+1–Boc]; $^1H$ NMR ($CDCl_3$) δ 4.26 (m, 2 H), 2.50 (m, 2 H), 2.04 (m, 2 H), 1.85 (m, 2 H), 1.55 (m, 2 H), 1.46 (s, 9 H).

C. 3-Hydroxymethyl-8α-aza-bicyclo[3.2.1]octane-8-carboxylic acid tert-butyl ester 3-Methylene-8-aza-bicyclo[3.2.1]octane-8-carboxylic acid tert-butyl ester (8.52 g, 38.2 mmol) was dissolved in anhydrous THF (100 mL) under an atmosphere of dry $N_2$ at room temperature. The solution was then cooled to 0° C. and to this solution was added 1.0 M borane in THF (42 mL). After 10 minutes, the mixture was warmed to room temperature and stirred overnight. The mixture was cooled to 0° C. to which was added 2.0 N NaOH (45 mL) and 30% hydrogen peroxide (15 mL). After 10 minutes the reaction was warmed to room temperature and was stirred for 3.5 hours. The THF was then removed under vacuum and the mixture was partitioned between $CH_2Cl_2$ and water. The $CH_2Cl_2$ layer was then washed succesively with 10% $NaHSO_3$ and brine. The $CH_2Cl_2$ layer was dried over $MgSO_4$, filtered and concentrated (vacuum) to give 10.3 g of an oil. The oil was purified by flash coloumn chromatography over silica gel (eluent: a gradient ethyl acetate/hexanes 10/90 to ethyl cetate/hexanes 50/50 ) to give 8.26 g of the title compound as a colorless oil.

C.I. m/z 142 [M+1–Boc]; $^1H$ NMR ($CD_3OD$) δ 4.10 (m, 2 H), 3.54 (m, 2 H), 2.06 (m, 2 H), 1.95 (m, 2 H), 1.80 (m, 1 H), 1.64 (m, 2 H), 1.45 (m, 2 H), 1.44(s, 9 H).

D. 3-Hydroxymethyl-8β-aza-bicyclo[3.2.1]octane-8-carboxylic acid tert-butyl ester PCC (4.40 g, 20.4 mmol) was dissolved in $CH_2Cl_2$ (30 mL) under an atmosphere of dry $N_2$ at room temperature. To this solution was added 10 g of 4A molecular sieves followed by a solution of 3-hydroxymethyl-8α-aza-bicyclo[3.2.1]octane-8-carboxylic acid tert-butyl ester (3.28 g, 13.6 mmol) in $CH_2Cl_2$ (30 mL). The rection mixture was stirred for 4 hours and then diluted with $Et_2O$ (200 mL). The resulting solution was decanted and passed through a silica gel plug eluting with $CH_2Cl_2$. The combined filtrates were concentrated (vacuum) to give 3-formyl-8α-aza-bicyclo[3.2.1]octane-8-carboxylic acid tert-butyl ester (2.70 g, 11.3 mmol) as an oil. The aldehyde was epimerized by dissolving the oil in anhydrous $CH_2Cl_2$ (45 mL) and treating the resulting solution with 1,8-diazabicyclo[5.4.0]undec-7-ene (350 mL, 2.33 mmol). The mixture was stirred overnight at room temperature and then concentrated (vacuum) to give an oil. The oil was dissolved in MeOH (50 mL) and then treated with $NaBH_4$ (515 mg, 13.6 mmol). The mixture was stirred for 5 hours and then concentrated (vacuum) to give an oil. The oil was partitioned between $CH_2Cl_2$ and water. The $CH_2Cl_2$ layer was washed with brine, dried over $MgSO_4$, filtered and concentrated (vacuum) to give 2.58 g of an oil. The oil was purified by flash coloumn chromatography over silica gel (eluent: a gradient ethyl acetate/hexanes 25/75 to ethyl acetate/hexanes 50/50) to give 1.88 g of the title compound.

C.I. m/z 186 [M+1 - isobutylene]; $^1$H NMR ($CD_3OD$) δ 4.16 (m, 2 H), 3.31 (m, 2 H), 2.03 (m, 1 H), 1.99 (m, 2 H), 1.70 (m, 2 H), 1.60 (m, 2 H), 1.44 (s, 9 H), 1.38 (m, 2 H).

E. 3-Methanesulfonyloxymethyl-8β-aza-bicyclo[3.2.1]octane-8-carboxylic acid tert-butyl ester 3-Hydroxymethyl-8β-aza-bicyclo[3.2.1]octane-8-carboxylic acid tert-butyl ester (1.35 g, 5.60 mmol) was dissolved in $CH_2Cl_2$ (25 mL) under an atmsophere of dry $N_2$. The solution was cooled to 0° C. to which $NEt_3$ (910 mL, 6.50 mmol) and methanesulphonyl chloride (500 mL, 6.46 mmol) were added. After 10 minutes the mixture was warmed to room temperature and stirred at this temperature for 45 minutes. The mixture was concentrated (vacuum) and then partitioned between $Et_2O$ and 0.01 N HCl. The $Et_2O$ layer was washed succesively with 0.01 N HCl, saturated $NaHCO_3$ and brine. The EtO layer was dried over $MgSO_4$, filtered and concentrated (vacuum) to give 1.77 g of the title compound as a colorless oil.

C.I. m/z 264 [M+1 - isobutylene]; $^1$H NMR ($CD_3Cl$) δ 4.11 (m, 2 H), 3.98 (m, 2 H), 2.97 (s, 3 H), 2.28 (m, 1 H), 1.95 (m, 2 H), 1.70 (m, 2 H), 1.60 (m, 4 H), 1.44 (s, 9 H).

F. 3-(1,3-Dioxo-1,3-dihydro-isoindol-2-ylmethyl)-8β-aza-bicyclo[3.2.1]octane-8carboxylic acid tert-butyl ester 3-Methanesufonyloxymethyl-8β-aza-bicyclo[3.2.1]octane-8-carboxylic acid tert-butyl ester (1.70 g, 5.33 mmol) was dissolved in anhydrous DMF (25 mL) under an atmosphere of dry $N_2$. To this solution was added potassium pthalimide (1.35 g, 7.30 mmol). The mixture was heated to 80° C. and stirred for 48 hours. The mixture was concentrated (vacuum) and then partitioned between $Et_2O$ and water. The $Et_2O$ layer was washed twice with water and then with brine. The $Et_2O$ layer was dried over $MgSO_4$, filtered and concentrated (vacuum) to give 1.90 g of a white foam.

C.I. m/z 315 [M+1- isobutylene]; $^1$H NMR (CDCl) δ 7.69–87 (m, 5 H), 4.09 (m, 2 H), 3.51 (m, 2 H), 2.32 (m, 1 H), 1.88 (m, 2 H), 1.46–1.60 (m, 6 H), 1.44 (s, 9 H).

G. 3-Aminomethyl-8β-aza-bicyclo[3.2.1]octane-8-carboxylic acid tert-butyl ester 3-(1,3-Dioxo-1,3-dihydro-isoindol-2-ylmethyl)-8β-aza-bicyclo[3.2.1]octane-8-carboxylic acid tert-butyl ester (1.88 g, 5.08 mmol) was dissolved in EtOH (45 mL) under an atmsophere of dry $N_2$. To this solution was added hydrazine hydrate (500 mL). The mixture was heated to 80° C. and stirred for 1 hour. The mixture was filtered and the resulting filtrate was concentrated (vacuum) to give 1.47 g of a white semi-solid. The semi-solid was triturated with $CH_2Cl_2$. The $CH_2Cl_2$ washings were combined and concentrated (vacuum) to give 970 mg of the title compound as a colorless oil.

C.I. m/z 185 [M+1- isobutylene]; $^1$H NMR ($CD_3OD$) δ 4.16 (m, 2 H), 2.44 (m, 2 H), 1.93 (m, 3 H), 1.60–1.80 (m, 4 H), 1.44 (s, 9 H), 1.25 (m, 2 H).

H. 3-Isothiocyanatomethyl-8β-aza-bicyclo[3.2.1]octane-8-carboxylic acid tert-butyl ester 3-Aminomethyl-8β-aza-bicyclo[3.2.1]octane-8-carboxylic acid tert-butyl ester (940 mg, 3.92 mmol) and 1,1'-thiocarbonyldiimidazole (800 mg, 4.04 mmol) were dissolved in $CH_2Cl_2$ (20 mL) under an atmosphere of dry $N_2$ at room temperature. The reaction was stirred overnight and then partitioned between 10% $NaHSO_4$ and $CH_2Cl_2$. The $CH_2Cl_2$ layer was washed succesively with 10% $NaHSO_4$, water and saturated $NaHCO_3$. The organic layer was dried over $MgSO_4$, filtered and concentrated (vacuum) to give 1.18 g of the title compound.

C.I. m/z 227 [M+1-isobutylene]; $^1$H NMR ($CDCl_3$) d=4.22 (m, 2 H), 3.55 (m, 2 H), 2.19 (m, 1 H), 1.96 (m, 2 H), 1.48–1.78 (m, 6 H), 1.45 (s, 9 H).

I. 3-(5Oxo-4,4-bis-pyridin-4-ylmethyl-2-thioxo-imidazolidin-1-ylmethyl)-8β-aza-bicyclo[3.2.1]octane-8-carboxylic acid tert-butyl ester 3-Isothiocyanatomethyl-8β-aza-bicyclo[3.2.1]octane-8-carboxylic acid tert-butyl ester (1.15 g, 4.08 mmol) and 2-amino-3-pyridin-4-yl-2-pyridin-4-ylmethyl-propionic acid methyl ester (1.66 g, 6.13 mmol) were dissolved in EtOH (10 mL) under an atmosphere of dry $N_2$. The mixture was heated to 80° C. and run at this temperature overnight. The reaction was concentrated (vacuum) and the resulting residue was purified by flash column chromatography over silica gel (eluent: a gradient of ethyl acetate to MeOH/ethyl acetate 6/94 ) to give 1.20 g of the title compound as a yellow foam.

C.I. m/z 522 [M+1]; $^1$H NMR ($CDCl_3$) δ=8.50 (m, 4 H), 7.98 (br s, 1 H), 7.11 (m, 4 H), 4.00 (m, 2 H), 3.16 (m, 4 H), 3.04 (d, J=13.2 Hz, 2 H), 1.60–2.00 (m, 5 H), 1.44 (s, 9 H), 1.33 (m, 2 H), 0.75 (m, 2 H).

J. 3-{2-[2-(4-Cyano-phenyl)-2-oxo-ethylsulfanyl]-5-oxo-4,4-bis-pyridin-4-ylmethyl-4,5-dihydro-imidazol-1-ylmethyl}-8β-aza-bicyclo[3.2.1octane-8-carboxylic acid tert-butyl ester To a −78° C. solution of potassium bis(trimethylsilyl)amide (500 mg, 2.39 mmol) in anhydrous THF (5 mL) under an atmosphere of dry $N_2$ was added 3-(5-Oxo-4,4-bis-pyridin-4-ylmethyl-2-thioxo-imidazolidin-1-ylmethyl-8β-aza-bicyclo[3.2.1]octane-8-carboxylic acid tert-butyl ester (1.13 mg, 2.17 mmol). The solution was warmed up to room temperature and after 15 minutes was cooled to −78° C. To this solution was added 4-cyanophenacyl bromide (486 mg, 2.17 mmol) and the mixture was warmed up to room temperature and stirred for 1 hour. The mixture was then partitioned between $CH_2Cl_2$ and saturated $NaHCO_3$. The $CH_2Cl_2$ layer was dried over $MgSO_4$, filtered and concentrated (vacuum) to give 1.52 g of an orange residue. The residue was purified by flash coloumn chromatography over silica gel (eluent: a gradient of ethyl acetate to MeOH/ethyl-acetate 5/95) to give 980 mg of the title compound as a yellow oil.

C.I. m/z 665 [M+1]; $^1$H NMR ($CDCl_3$) δ=8.42 (m, 4 H), 8.19 (d, J=8.4 Hz, 2 H), 7.90 (d, J=8.4 Hz, 2 H), 6.96 (m, 4 H), 4.59 (s, 2 H), 4.01 (m, 2 H), 3.05 (m, 4 H), 2.80 (m, 2 H), 1.82 (m, 2 H), 1.75 (m, 1 H), 1.43 (s, 9 H), 1.33 (m, 2 H), 0.62 (m, 2 H).

K. 3-{2-[2-(4-Cyano-phenyl)-2-oxo-ethylidene]-5-oxo-4,4-bis-pyridin-4-ylmethyl-imidazolidin-1-ylmethyl}-8β-aza-bicyclo[3.2.1]octane-8-carboxylic acid tert-butyl ester 3-{2-[2-(4-Cyano-phenyl)-2-oxo-ethylsulfanyl]-5-oxo-4,4-bis-pyridin-4-ylmethyl-4,5-dihydro-imidazol-1-ylmethyl}-8β-aza-bicyclo[3.2.1]octane-8-carboxylic acid tert-butyl ester (950 mg, 1.43 mmol) and triphenyl phosphine (1.50 g, 5.73 mmol) were dissolved in anhydrous toluene (15.0 ml) under an atmosphere of dry $N_2$. The mixture was heated to 100° C. and stirred for 13 hours. The mixture was concentrated (vacuum) and then partitioned between 0.01 N HCl and $Et_2O$. The aqueous layer was washed two times with $Et_2O$ and then basified to pH=8 with NaHCO3. The product was extracted into $CH_2Cl_2$, dried over $MgSO_4$, filtered and concentrated (vacuum) to give a tan solid. The solid was triturated with $CH_2Cl_2$/hexanes to give 810 mg of the title compound as a white solid.

C.I. m/z 633 [M+1]; $^1$H NMR (CDCl$_3$) δ 10.40 (br s, 1 H), 8.46 (m, 4 H), 7.83 (d, J=8.4 Hz, 2 H), 7.71 (d, J=8.4Hz, 2 H), 7.11 (m, 4 H), 5.10 (s, 1 H), 4.00 (m, 2 H), 3.26 (d, J=13.2 Hz, 2 H), 3.07 (d, J=13.2 Hz, 2 H), 2.86(m, 2 H), 1.85 (m, 2 H), 1.70 (m, 1 H), 1.43 (s, 9 H), 1.30 (m, 2 H), 0.65 (m, 2 H).

EXAMPLE 73

4-{[1-(8β-Aza-bicyclo[3.2.1]oct-3-ylmethyl)-5-oxo-4,4-bis-pyridin-4-ylmethyl-imidazolidin-2-ylidene]-acetyl}-benzonitrile 3-{2-[2-(4-Cyano-phenyl)-2-oxo-ethylidene]-5-oxo-4,4-bis-pyridin-4-ylmethyl-imidazolidin-1-ylmethyl}8β-aza-bicyclo[3.2.1]octane-8-carboxylic acid tert-butyl ester (780 mg, 1.23 mmol) was dissolved in 5 mL of TFA under an atmosphere of dry $N_2$. The mixture was stirred at room temperature for 1 hour and then concentrated (vacuum). The resulting residue was partitioned between $CH_2Cl_2$ and 0.01 N NaOH. The $CH_2Cl_2$ layer was dried over $MgSO_4$, filtered and concentrated (vacuum) to give 550 mg of the title compound as a tan foam.

C.I. m/z 533 [M+1]; $^1$H NMR (CDCl$_3$) δ 10.40 (br s, 1 H), 8.46 (m, 4 H), 7.86 (m, 2 H), 7.71 (m, 2 H), 7.10(m, 4 H), 5.20 (s, 1 H), 3.38 (m, 2H), 3.25 (d, J=13.5 Hz, 2 H), 3.06 (d, J=13.5 Hz, 2 H), 2.88 (d, J=8.5 Hz, 2 H), 1.5–1.8 (m, 3H), 1.39 (m, 2 H), 1.07 (m, 2 H), 0.73 (m, 2 H).

EXAMPLE 74

4-{(1-(8-Acetyl-8β-aza-bicyclo[3.2.1 1oct-3-ylmethyl)-5-oxo-4,4-bis-pyridin-4-ylmethyl-imidazolidin-2-ylidene]-acetyl}-benzonitrile 4-{[1-(8β-Aza-bicyclo[3.2.1]oct-3ylmethyl)-5-oxo-4,4-bis-pyridin-4-ylmethyl-imidazolidin-2-ylidene]-acetyl}-benzonitrile (51 mg, 0.096 mmol) was dissolved in 1.0 mL of $CH_2Cl_2$ under an atmosphere of dry $N_2$. To this solution was added $NEt_3$ (20 mL, 0.14 mmol) and acetic anhydride (11 mL, 0.12 mmol) and the mixture was stirred overnight at room temperature. The mixture was then partitioned between $CH_2Cl_2$ and saturated $NaHCO_3$. The $CH_2Cl_2$ layer was dried over $MgSO_4$, filtered and concentrated (vacuum) to give a brown residue. The residue was triturated with $CH_2Cl_2$/hexanes to give 46 mg of the title compound as a tan powder.

C.I. m/z 575[M+1]; $^1$H NMR (CDCl$_3$) δ 10.55 (br s, 1 H), 8.46 (m, 4 H), 7.83 (m, 2 H), 7.72 (m, 2 H), 7.12 (m, 4 H), 5.08 (s, 1 H), 4.51 (m, 1 H), 3.89 (m, 1 H), 3.25 (m, 2 H), 3.08 (m, 2 H), 2.84 (m, 2 H), 1.98 (s, 3 H), 1.70–1.97 (m, 3 H), 1.38 (m, 2 H), 1.22 (m, 2 H), 0.60 (m, 2H).

EXAMPLE 75

4-{[1-(8-Methanesulfonyl-8β-aza-bicyclo[3.2.1]oct-3-ylmethyl)-5-oxo-4,4-bis-pyridin-4-ylmethyl-imidazolidin-2-ylidene]-acetyl}-benzonitrile 4-{[1-(8β-Aza-bicyclo[3.2.1]oct-3ylmethyl-5-oxo-4,4-bis-pyridin-4-ylmethyl-imidazolidin-2-ylidene]-acetyl}-benzonitrile (50 mg, 0.094 mmol) was dissolved in 1.0 mL of $CH_2Cl_2$ under an atmosphere of dry $N_2$. To this solution was added $NEt_3$ (20 mL, 0.14 mmol) and methanesulphonyl chloride (9.0 mL, 0.12 mmol). The mixture was stirred overnight at room temperature and then partitioned between $CH_2Cl_2$ and saturated $NaHCO_3$. The $CH_2Cl_2$ layer was dried over $MgSO_4$, filtered and concentrated (vacuum) to give a brown residue. The residue was triturated with $CH_2Cl_2$,hexanes to give 52 mg of the title compound as a tan powder.

C.I. m/z 611[M+1]; $^1$H NMR (CDCl$_3$) δ 10.43 (br s, 1 H), 8.47 (m, 4 H), 7.84 (m, 2 H), 7.72 (m, 2 H), 7.11 (m, 4 H), 5.10 (s, 1 H), 4.04 (m, 2 H), 3.25 (d, J=13.5 Hz, 2 H), 3.08 (d, J=13.5 Hz, 2 H), 2.90 (d, J=7.5 Hz, 2 H), 2.81 (s, 3 H), 1.93 (m, 2 H), 1.45 (m, 2 H), 1.22 (m, 2 H), 0.77 (m, 2 H).

EXAMPLE 76

4-{[1-(8-Benzenesulfonyl-8β-aza-bicyclo[3.2.1]oct-3-ylmethyl)-5-oxo-4,4-bis-pyridin-4-ylmethyl-imidazolidin-2-ylidene]-acetyl}-benzonitrile 4-{[1-(8β-Aza-bicyclo[3.2.1]oct-3ylmethyl)-5-oxo-4,4-bis-pyridin-4-ylmethyl-imidazolidin-2-ylidene]-acetyl}-benzonitrile (50 mg, 0.094 mmol) was dissolved in 1.0 mL of $CH_2Cl_2$ under an atmosphere of dry $N_2$. To this solution was added $NEt_3$ (20 mL, 0.14 mmol) and benzenesulphonyl chloride (14 mL, 0.11 mmol). The mixture was stirred overnight at room and then partitioned between $CH_2Cl_2$ and saturated $NaHCO_3$. The $CH_2Cl_2$ layer was dried over $MgSO_4$, filtered and concentrated (vacuum) to give a brown residue. The residue was triturated with $CH_2Cl_2$/hexanes to give 63 mg of the title compound as a tan powder.

C.I. m/z 673[M+1]; $^1$H NMR (CDCl$_3$) δ 10.40 (br s, 1 H), 8.44 (m, 4 H), 7.84 (m, 2 H), 7.78 (m, 2 H), 7.72 (m, 2 H), 7.55 (m, 1 H), 7.46 (m, 2 H), 7.09 (m, 4 H), 5.10 (s, 1 H), 4.05 (m, 2 H), 3.24 (d, J=13.4 Hz, 2 H), 3.07 (d, J=13.4 Hz, 2 H), 2.87 (d, J=7.5 Hz, 2 H), 0.70–1.80 (m, 9 H).

EXAMPLE 77

3-{2-[2-(4-Cyano-phenyl)-2-oxo-ethylidene]-5-oxo-4,4-bis-pyridin-4-ylmethyl-imidazolidin-1-ylmethyl}-8α-aza-bicyclo[3.2.1]octane-8-sulfonic acid dimethylamide 4-{[1-(8α-Aza-bicyclo[3.2.1]oct-3-ylmethyl-5-oxo-4,4-bis-pyridin-4-ylmethyl-imidazolidin-2-ylidene]-acetyl}benzonitrile (50 mg, 0.094mmol) was dissolved in 1.0 mL of $CH_2Cl_2$ under an atmosphere of dry $N_2$. To this solution was added $NEt_3$ (20 mL, 0.14 mmol) and dimethylsulfamoyl chloride (12 mL, 0.11 mmol). The mixture was stirred overnight at room temperature and then partitioned between $CH_2Cl_2$ and saturated $NaHCO_3$. The $CH_2Cl_2$ layer was dried over $MgSO_4$, filtered and concentrated (vacuum) to give a brown residue. The residue was triturated with $CH_2C_2$/hexanes to give 67 mg of the title compound as a yellow powder.

C.I. m/z 640[M+1]; $^1$H NMR (CDCl$_3$) δ 10.38 (br s, 1 H), 8.46 (m, 4 H), 7.84 (d, J=8.1 Hz, 2 H), 7.72 (d, J=8.1 Hz, 2 H), 7.11 (m, 4 H), 5.13 (s, 1 H), 3.89 (m, 2 H), 3.26 (d, J=13.3 Hz, 2 H), 3.09 (d, J=13.3 Hz, 2 H), 2.91 (d, J=7.2 Hz, 2 H), 2.74 (s, 6 H), 1.98 (m, 2 H), 0.70–1.80 (m, 7 H).

EXAMPLE 78

4-({1-[8-(1-Methyl-1H-imidazole-4-sulfonyl)-8β-aza-bicyclo[3.2.1]oct-3-ylmethyl]-5-oxo-4,4-bis-pyridin-4-ylmethyl-imidazolidin-2-ylidene}-acetyl)-benzonitrile 4-{[1-(8β-Aza-bicyclo[3.2.1]oct-3-ylmethyl)-5-oxo-4,4-bis-pyridin-4-ylmethyl-imidazolidin-2-ylidene3-acetyl}- benzonitrile (50 mg, 0.094mmol) was dissolved in 1.0 mL of CH$_2$Cl$_2$ under an atmosphere of dry N$_2$. To this solution was added NEt$_3$ (20 mL, 0.14 mmol) and 1-methylimidazole-4-sulphonyl chloride (21 mg, 0.11 mmol). The mixture was stirred overnight at room temperature and then partitioned between CH$_2$Cl$_2$ and saturated NaHCO$_3$. The CH$_2$Cl$_2$ layer was dried over MgSO$_4$, filtered and concentrated (vacuum) to give a brown residue. The residue was triturated with CH$_2$Cl$_2$/hexanes to give 55 mg of the title compound as a yellow powder.

C.I. m/z 677[M+1]; $^1$H NMR (CDCl$_3$) δ 10.43 (br s, 1 H), 8.43 (m, 4 H), 7.84 (m, 2 H), 7.71 (m, 2 H), 7.39 (d, J=1.3 Hz, 1 H), 7.35 (d, J=1.3 Hz, 1 H), 7.09 (m, 4 H), 5.12 (s, 1 H), 4.09 (m, 2 H), 3.71 (s, 3 H), 3.23 (d, J=13.3 Hz, 2 H), 3.06 (d, J=13.3 Hz, 2 H), 2.87 (d, J=7.3 Hz, 2 H), 0.70–2.00 (m, 9 H).

EXAMPLE 79

4-{2-[2-(4-Cyano-phenyl)-2-oxo-ethylidene]-5-oxo-4,4-bis-pyridin-4-ylmethyl-imidazolidin-1-ylmethyl}-N,N-dimethyl-benzenesulfonamide The same procedure that was used in Example 61 was followed except that 4-aminomethyl-N,N-dimethyl-benzenesulfonamide was used in the place of 3-aminomethyl-8α-aza-bicyclo[3.2.1]octane-8-carboxylic acid tert-butyl ester in Step E of Example 61 to give the title compound as a white solid.

$^1$H NMR (CDCl$_3$) δ 10.42 (br s, 1 H), 8.48 (m, 4 H), 7.84 (m, 2 H), 7.69 (m, 2 H), 7.66 (m, 2 H), 7.55 (d, J=8.2 Hz, 1 H), 7.14 (m, 4 H), 6.48 (d, J=8.2 Hz, 1 H), 4.96 (s, 1 H), 4.39 (s, 2 H), 3.33 (d, J=13.1 Hz, 2 H), 3.15 (d, J=13.1 Hz, 2 H), 2.69 (s, 6 H).

EXAMPLE 80

4-{[1-(3-Chloro-benzyl)-5-oxo-4,4-bis-pyridin-4-ylmethyl-imidazolidin-2-ylidene]-acetyl}-benzonitrile The same procedure that was used in Example 61 was followed except 1-chloro-3-isothiocyanatomethyl-benzene was used in the place of 3-isothiocyanatomethyl-8α-aza-bicyclo3.2.1]-octane-8-carboxylic acid tert-butyl ester in Step F of Example 61 to give the title compound as a white solid.

C.I. m/z 534[M+I]; $^1$H NMR (CDCl$_3$) δ 10.44 (br s, 1 H), 8.40 (m, 4 H), 7.68 (d, J=8.2 Hz, 2 H), 7.64 (d,J=8.2 Hz, 2 H), 7.15 (m, 5 H), 7.02 (t, J=7.8 Hz, 1 H), 6.82 (s, 1 H), 6.01 (d, J=7.8 Hz, I H), 5.03 (s, I H), 4.20 (s, 2 H), 3.31 (d, J=13.3 Hz, 2 H), 3.16 (d, J=13.3 Hz, 2 H).

EXAMPLE 81

4-{[1-(3-Methoxy-benzyl)-5-oxo-4,4-bis-pyridin-4-ylmethyl-imidazolidin-2-ylidene]-acetyl}-benzonitrile The same procedure that was used in Example 61 was followed except 1-isothiocyanatomethyl-3-methoxy-benzene was used in the place of 3-isothiocyanatomethyl-8α-aza-bicyclo[3.2.1]-octane-8-carboxylic acid tert-butyl ester in Step F of Example 61 to give the title compound as a white solid.

C.I. m/z 530[M+1]; $^1$H NMR (CDCl$_3$) δ 10.44 (br s, 1 H), 8.44 (m, 4 H), 7.72 (m, 2 H), 7.64 (m, 2 H), 7.11 (m, 4 H), 7.04 (t, J=8.1 Hz, 1 H), 6.74 (m, 1 H), 6.44 (s, 1 H), 5.72 (m, I H), 5.10 (s, 1 H), 4.24 (s, 2 H), 3.74 (s, 3 H), 3.32 (d, J=13.3 Hz, 2 H), 3.09 (d, J=13.3 Hz, 2 H).

EXAMPLE 82

4-{[1-(3-Fluoro-benzyl)-5-oxo-4,4-bis-pyridin-4-ylmethyl-imidazolidin-2-ylidene]-acetyl}-benzonitrile The same procedure that was used in Example 61 was followed 1-fluoro-3-isothiocyanatomethyl-benzene was used in the place of 3-isothiocyanatomethyl-8α-aza-bicyclo [3.2.1]-octane-8-carboxylic acid tert-butyl ester in Step F of Example 61 to give the title compound as a white solid.

C.I. m/z 518[M+1]; $^1$H NMR (CDCl$_3$) δ 10.40 (br s, 1 H), 8.45 (m, 4 H), 7.71 (d, J=8.4 Hz, 2 H), 7.65 (d, J=8.4 Hz, 2 H), 7.12 (m, 5 H), 6.91 (m, 1 H), 6.44 (m, 1 H), 5.99 (m, 1 H), 5.05 (s, 1H), 4.26 (s, 2 H), 3.33 (d, J=13.3 Hz, 2 H), 3.12 (d, J=13.3 Hz, 2 H).

EXAMPLE 83

4-{[1-(2-Chloro-benzyl)-5-oxo-4,4-bis-pyridin-4-ylmethyl-imidazolidin-2-ylidene]-acetyl}-benzonitrile The same procedure that was used in Example 61 was 1-chloro-2-isothiocyanatomethyl-benzene was used in the place of 3-isothiocyanatomethyl-8α-aza-bicyclo[3.2.1]-octane-8-carboxylic acid tert-butyl ester in Step F of Example 61 to give the title compound as a white solid.

C.I. m/z 534 {M+1]; $^1$H NMR (CDCl$_3$) δ 10.42 (br s, 1 H), 8.41 (m, 4 H), 7.69 (m, 2 H), 7.62 (m, 2 H), 7.24 (m, 1 H), 7.17 (m, 4 H), 7.09 (m, 1 H), 6.86 (m, I H), 5.38 (d, J=7.7 Hz, 1 H), 4.99 (s, 1 H), 4.35 (s, 2 H), 3.32 (d, J=13.3 Hz, 2 H), 3.18 (d, J=13.3 Hz, 2 H).

EXAMPLE 84

4-{[1-(4-Methanesulfonyl-benzyl)-5-oxo-4,4-is-pyridin-4-ylmethyl-imidazolidin-2-ylidene]-acetyl}-benzonitrile The same procedure that was used in Example 61 was followed except that 4-methanesulfonyl-benzylamine was used in the place of 3-aminomethyl-8α-aza-bicyclo[3.2.1] octane-8-carboxylic acid tert-butyl ester in Step E of Example 61 to give the title compound as a white solid.

C.I. m/z 578 [M+1]; $^1$H NMR (CDCl$_3$) δ 10.43 (br s, I H), 8.46 (d, J=5.9 Hz, 4 H), 7.65–7.72 (m, 6 H), 7.11 (d, J=5.9 Hz, 4 H), 6.50 (d, J=8.0 Hz, 1 H), 4.97 (s, 1 H), 4.35 (s, 2 H), 3.32 (d, J=13.1 Hz, 2 H), 3.13 (d, J=13.1 Hz, 2 H), 3.05 (s, 3 H).

EXAMPLE 85

4-{[1-(2-Methoxy-benzyl)-5-oxo-4,4-bis-pyridin-4-ylmethyl-imidazolidin-2-ylidene]-acetyl}-benzonitrile The same procedure that was used in Example 61 was followed except 1-isothiocyanatomethyl-2-methoxy-benzene was used in the place of 3-isothiocyanatomethyl-8α-aza-bicyclo[3.2.1]-octane-8-carboxylic acid tert-butyl ester in Step F of Example 61 to give the title compound as a white solid.

C.I. m/z 530[M+1]; $^1$H NMR (CDCl$_3$) δ 10.41 (br s, 1 H), 8.44 (d, J=5.4 Hz, 4 H), 7.75 (d, J=8.4 Hz, 2 H), 7.66 (d, J=8.4 Hz, 2 H), 7.17 (m, 5 H), 6.79 (d, J=8.3 Hz, 1 H), 6.71

(t, J=8.3 Hz, 1 H), 5.94 (d, J=8.3 Hz, 1 H), 5.29 (s, 1 H), 4.30 (s, 2 H), 3.74 (s, 3 H), 3.35 (d, J=13.3 Hz, 2 H), 3.14 (d, J=13.3 Hz, 2 H).

EXAMPLE 86

4-[2-[2-(4-Cyano-phenyl)-2-oxo-ethylidene]-4,4-bis-(3-methyl-3H-imidazol4-ylmethyl)-5-oxo-imidazolidin-1-ylmethyl]-N,N-dimethyl-benzenesulfonamide Using the same procedure as described in Example 53, 4-isothiocyanatomethyl-N,N-dimethyl-benzenesulfonamide (0.36 mmol) was used in the place of 3-benzenesulfonyl-6-isothiocyanato-3-aza-bicyclo[3.1.0]hexane. After cyclization with 2-amino-3-(3-methyl-3H-imidazol-4-yl)-2-(3-methyl-3H-imidazol-4-ylmethyl)-propionic acid methyl ester, sulfur-alkylation of 4-cyanophenacyl bromide in the presence of potassium bis(trimethylsilyl)amide, and sulfur-extrusion in the presence of triphenylphosphine, 9 mg of the title compound was obtained as a white solid.

Cl-MS. m/z 613.2 [M+1]

What is claimed is:

1. A compound of the formula

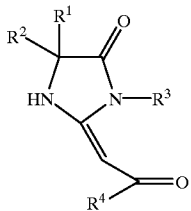

or a pharmaceutically acceptable salt thereof, wherein:

$R^1$ and $R^2$ are each independently selected from the group consisting of $C_1$–$C_{10}$ alkyl, $C_2$–$C_{10}$ alkenyl, $C_2$–$C_{10}$ alkynyl, —$(CH_2)_p(C_6$–$C_{10}$ aryl), and —$(CH_2)_p$(4–10 membered unsaturated heterocyclyl), wherein p is an integer from 0 through 3, or $R^1$ and $R^2$ form a $C_3$–$C_6$ cycloalkyl ring, and wherein any of said $R^1$ and $R^2$ groups are optionally substituted with 1 to 3 $R^6$ groups, provided that when $R^1$ and $R^2$ form a $C_3$–$C_6$ cycloalkyl ring, said $C_3$–$C_6$ cycloalkyl ring is substituted with at least one $R^6$ selected from $C_2$–$C_{10}$ alkenyl, $C_2$–$C_{10}$ alkynyl, and —$(CH_2)_t(C_6$–$C_{10})$ aryl wherein t is an integer from 1 to 3;

and wherein one or both of $R^1$ and $R^2$ is —$(CH_2)_p$(6 membered unsaturated heterocyclyl containing one or more nitrogen atoms);

$R^3$ is —$(CH_2)_m$(4–10 membered heterocyclyl) optionally substituted with 1 to 5 $R^6$ groups;

m in the aforementioned $R^3$ groups is independently an integer from 0 through 6; and $R^4$ is $C_6$–$C_{10}$ aryl, 4–10 membered heterocyclyl, or $C_1$-$C_6$ alkyl, each of said $R^4$ groups being optionally substituted by 1 to 3 $R^6$ groups;

each $R^5$ is independently selected from halo, $C_1$–$C_6$ alkyl substituted by 1 to 3 halo, nitro, cyano, —$OR^9$, —$C(O)R^9$, —$SR^9$, —$SO_2R^9$, —$SO_3H$, —$S(O)R^7$, —$NR^7R^8$, —$C(O)OR^9$, —$OC(O)R^9$, —$SO_2NR^9R^8$, —$C(O)NR^9R^8$, —$NR^8C(O)R^9$, —$OC(O)NR^9R^8$, —$C(O)ONR^7R^9$, —$NR^8C(O)NR^9$ $R^8$, —$NR^8C(O)O(C_1$–$C_4$ alkyl), —$C(NR^8)NR^9R^8$, —$C(NCN)NR^9R^8$, —$C(NCN)S(C_1$–$C_4$ alkyl or $C_1$–$C_4$ haloalkyl), —$NR^8C(NCN)S(C_1$–$C_4$ alkyl or $C_1$–$C_4$ haloalkyl), —$NR^8C(NCN)NR^7R^8$, —$NR^8SO_2(C_1$–$C_4$ alkyl or $C_1$–$C_4$ haloalkyl), —$NR^8C(O)C(O)R^8$, —$NR^8C(O)C(O)NR^9R^8$, —$P(O)(OR^7)_2$, and —$(CH_2)_q$(4–10 membered heterocyclyl), q is an integer from 0 through 3, and the alkyl and heterocyclyl moieties of the foregoing $R^5$ groups are optionally substituted by 1 to 3 $R^{10}$ groups;

each $R^6$ is independently selected from $R^5$, $C_1$–$C_6$ alkyl, $C_2$–$C_{10}$ alkenyl, $C_2$–$C_{10}$ alkynyl and —$(CH_2)_t(C_6$–$C_{10}$ aryl) optionally substituted with1 to 3 $R^{10}$ groups, t being an integer from 0 through 3;

each $R^7$ is independently hydrogen or $C_1$–$C_4$ alkyl optionally substituted by 1 to 3 halo;

each $R^8$ is independently $R^7$ or —$OR^7$;

each $R^9$ is independently selected from hydrogen, $C_1$–$C_6$ alkyl, —$(CH_2)_q(C_6$–$C_{10}$ aryl), and —$(CH_2)_q$(4–10 membered heterocyclyl), said $R^9$ groups, except H, are optionally substituted with 1 to 3 $R^{10}$ groups, and each q is independently an integer from 0 through 3; and, each $R^{10}$ is independently selected from halo, nitro, cyano, $C_1$–$C_6$ alkyl, $C_1$–$C_6$ haloalkyl, $C_1$–$C_6$ alkoxy, $C_1$–$C_6$ haloalkoxy, —$C(O)O(C_1$–$C_6$ alkyl), and $C_6$–$C_{10}$ aryl; with the proviso that $R^1$ and $R^2$ are not both simultaneously $C_1$–$C_{10}$ alkyl.

2. The compound of claim 1 wherein one or both of $R^1$ and $R^2$ is 2- 3- or 4-pyridinylmethyl.

3. The compound of claim 1 wherein $R^3$ is —$(CH2)_m$ (4–10 membered azacyclyl), optionally substituted with 1 to 3 $R^6$ groups.

4. The compound of claim 3 selected from the group consisting of:

4-{[1-(1α,5α,6α-3-tert-Butoxylcarbonyl-3-aza-bicyclo[3.1.0]hex-6-yl)-5-oxo-4,4-bis-pyridin-4-ylmethyl-imidazolidin-2-ylidene]-acetyl}-benzonitrile;

4-{[1-(1α,5α,6α-3-Aza-bicyclo[3.1.0]hex-6-yl)-5-oxo-4,4-bis-pyridin-4-ylmethyl-imidazolidin-2-ylidene]-acetyl}-benzonitrile;

4-({5-Oxo-1-[1α,5α,6α-3-(1-phenyl-1H-tetrazol-5-yl)-3-aza-bicyclo[3.1.0]hex-6-yl]-4,4-bis-pyridin-4-ylmethyl-imidazolidin-2-ylidene}-acetyl)-benzonitrile;

1α,5α,6α-6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hexane-3-carboxylic acid benzyl ester;

4-({1-[1α,5α,6α-3-(3,3-Dimethyl-butyryl)-3-aza-bicyclo[3.1.0]hex-6-yl]-5-oxo-4,4-bis-pyridin-4-ylmethyl-imidazolidin-2-ylidene}-acetyl)-benzonitrile;

4-({5-Oxo-4,4-bis-pyridin-4-ylmethyl-1-[1α,5α,6α-3-(thiophen-2-yl-acetyl)-3-aza-bicyclo[3.1.0]hex-6-yl]-imidazolidin-2-ylidene}-acetyl)-benzonitrile;

1α,5α,6α-(6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hex-3-yl)-phosphonic acid diethyl ester;

4-{[1-(1α,5α,6α-3-Benzenesulfonyl-3-aza-bicyclo[3.1.0]hex-6-yl-5-oxo-4,4-bis-pyridin-4-ylmethyl-imidazolidin-2-ylidene]-acetyl}-benzonitrile;

4-({1-[1α,5α,6α-3-(4-Methoxy-benzenesulfonyl)-3-aza-bicyclo[3.1.0]hex-6-yl]-5-oxo-4,4-bis-pyridin-4-ylmethyl-imidazolidin-2-ylidene}-acetyl)-benzonitrile;

4-{[5-Oxo-1-(1α,5α,6α-3-phenylmethanesulfonyl-3-aza-bicyclo[3.1.0]hex-6-yl)-4,4-bis-pyridin-4-ylmethyl-imidazolidin-2-ylidene]-acetyl}-benzonitrile;

4-({5-Oxo-4,4-bis-pyridin-4-ylmethyl-1-[1α,5α,6α-3-(toluene-4-sulfonyl)-3-aza-bicyclo[3.1.0]hex-6-yl]-imidazolidin-2-ylidene}-acetyl)-benzonitrile;

4-({5-Oxo-4,4-bis-pyridin-4-ylmethyl-1-[1α,5α,6α-3-(toluene-2-sulfonyl)-3-aza-bicyclo[3.1.0]hex-6-yl]-imidazolidin-2-ylidene}-acetyl)-benzonitrile;

4-({5-Oxo-1-[1α,5α,6α-3-(piperidine-1-sulfonyl)-3-aza-bicyclo[3.1.0]hex-6-yl]-4,4-bis-pyridin-4-ylmethyl-imidazolidin-2-ylidene}-acetyl)-benzonitrile;

4-({5-Oxo-4,4-bis-pyridin-4-ylmethyl-1-[1α,5α,6α-3-(thiophene-2-sulfonyl)-3-aza-bicyclo[3.1.0]hex-6-yl]-imidazolidin-2-ylidene}-acetyl)-benzonitrile;

4-({1-[1α,5α,6α-3-(5-Bromo-thiophene-2-sulfonyl3-aza-bicyclo[3.1.0]hex-6-yl]-5-oxo-4,4-bis-pyridin-4-ylmethyl-imidazolidin-2-ylidene}-acetyl)-benzonitrile;

4-({1-[1α,5α,6α-3-(4-Ethyl-piperazine-1-sulfonyl)-3-aza-bicyclo[3.1.0]hex-6-yl]-5-oxo-4,4-bis-pyridin-4-ylmethyl-imidazolidin-2-ylidene}-acetyl)-benzonitrile;

4-({5-Oxo-1-[1α,5α,6α-3-(propane-1-sulfonyl)-3-aza-bicyclo[3.1.0]hex-6-yl]-4,4-bis-pyridin-4-ylmethyl-imidazolidin-2-ylidene}acetyl)-benzonitrile;

1-(1α,5α,6α-6-{2-[2-(4-Cyano-phenyl)-2-oxo-ethylidene]-5-oxo-4,4-bis-pyridin-4-ylmethyl-imidazolidin-1-yl}-3-aza-bicyclo[3.1.0]hexane-3-sulfonyl)-piperidine-4-carboxylic acid ethyl ester;

4-({5-Oxo-1-[1α,5α,6α-3-(4-propyl-piperidine-1-sulfonyl3-aza-bicyclo[3.1.0]hex-6-yl]-4,4-bis-pyridin-4-ylmethyl-imidazolidin-2-ylidene}-acetyl)-benzonitrile;

4-({1-[1α,5α,6α-3-(4-Isopropyl-piperazine- -sulfonyl)-3-aza-bicyclo[3.1.0]hex-6-yl]-5-oxo-4,4-bis-pyridin-4-yl-methyl-imidazolidin-2-ylidene}-acetyl)-benzonitrile;

4-{[1α,5α,6β-1-(3-Benzenesulfonyl-3-aza-bicyclo[3.1.0]hex-6-ylmethyl)-5-oxo-4,4-bis-pyridin-4-ylmethyl-imidazolidin-2-ylidene]-acetyl}-benzonitrile;

1α,5α,6α-6-{4-Allyl-2-[2-(4-cyano-phenyl)-2-oxo-ethylidene]-5-oxo-4-pyridin-4-ylmethyl-imidazolidin-1-yl}-3-aza-bicyclo[3.1.0]hexane-3-carboxylic acid tert-butyl ester;

4-{[4-Allyl-1-(1α,5α,6α-3-benzenesulfonyl-3-aza-bicyclo[3.1.0]hex-6-yl)-5-oxo-4-pyridin-4-ylmethyl-imidazolidin-2-ylidene]-acetyl}-benzonitrile;

5-{[5-Oxo-4-allyl-4-pyridin-4-ylmethyl-1-(1α,5α,6α-3-(thiophene-2-acetyl)-3-aza-bicyclo[3.1.0]hex-6-yl)-imidazolidin-2-ylidene]-acetyl}-benzonitrile;

4-({4-Allyl-5-oxo-4-pyridin-4-ylmethyl-1-11 a,5a,6a-3-(thiophen-2-yl-sulfonyl)-3-aza-bicyclo[3.1.0]hex-6-yl]-imidazolidin-2-ylidene}-acetyl)-benzonitrile;

1α,5α,6α-6-[2-[2-(4-Cyano-phenyl)-2-oxo-ethylidene]-4-(3-methyl-but-2-enyl-5-oxo-4-pyridin-4-ylmethyl-imidazolidin-1-yl]-3-aza-bicyclo[3.1.0]hexane-3-carboxylic acid tert-butyl ester;

4-{[1-[1α,5α,6α-3-(5-Bromo-thiophene-2-sulfonyl)-3-aza-bicyclo[3.1.0]hex-6-yl]-4-(3-methyl-but-2-enyl)-5-oxo-4-pyridin-4-ylmethyl-imidazolidin-2-ylidene]-acetyl}-benzonitrile;

1α,5α,6α-6-{2-[2-(4-Cyano-phenyl)-3-2-oxo-ethylidene]-5-oxo-4-pyridin-4-ylmethyl-4-thiophen-3-ylmethyl-imidazolidin-1-yl}-3-aza-bicyclo[3.1.0]hexane-3-carboxylic acid tert-butyl ester;

4-{[1-(1α,5α,6α-3-Benzenesulfonyl-3-aza-bicyclo[3.1.0]hex-6-yl)-5-oxo-4-pyridin-4-ylmethyl-4-thiophen-3-ylmethyl-imidazolidin-2-ylidene]-acetyl}-benzonitrile;

1α,5α,6α-6-(4-(3-Chloro-but-2-enyl)-2-[2-(4-cyano-phenyl-2-oxo-ethylidene]-5-oxo-4-pyridin-4-ylmethyl-imidazolidin-1-yl}-3-aza-bicyclo[3.1.0]hexane-3-carboxylic acid tert-butyl ester;

4-{[1-[1α,5α,6α-3-(5-Bromo-thiophene-2-sulfonyl)-3-aza-bicyclo[3.1.0]hex-6-yl]-4-(3-chloro-but-2-enyl)-5-oxo-4-pyridin-4-ylmethyl-imidazolidin-2-ylidene]-acetyl}-benzonitrile;

4-{[1α,6α,7α-1-(3-Benzenesulfonyl-3-aza-bicyclo[4.1.0]hept-7-ylmethyl)-5-oxo-4,4-bis-pyridin-4-ylmethyl-imidazolidin-2-ylidene]-acetyl}-benzonitrile;

4-{[1α,6α,7α-1-(3-Benzenesulfonyl-3-aza-bicyclo[4.1.0]hept-7-yl5-oxo-4,4-bis-pyridin-4-ylmethyl-imidazolidin-2-ylidene]-acetyl}-benzonitrile;

4-{[1-(8-Methanesulfonyl-8α-aza-bicyclo[3.2.1]oct-3-ylmethy15-oxo-4,4-bis-pyridin-4-ylmethyl-imidazolidin-2-ylidene]-acetyl}-benzonitrile;

4-{[1-(8-Benzenesulfonyl-8α-aza-bicyclo[3.2.1]oct-3-ylmethyl)-5-oxo-4,4-bis-pyridin-4-ylmethyl-imidazolidin-2-ylidene]-acetyl}-benzonitrile;

3-(2-[2-(4-Cyano-phenyl-2-oxo-ethylidene]-5-oxo-4,4-bis-pyridin-4-ylmethyl-imidazolidin-1-ylmethyl)-8α-aza-bicyclo[3.2.1]octane-8-sulfonic acid dimethylamide;

4-{[1-(8-Ethanesulfonyl-8α-aza-bicyclo[3.2.1]oct-3-ylmethyl)-5-oxo-4,4-bis-pyridin-4-ylmethyl-imidazolidin-2-ylidene]-acetyl}-benzonitrile;

4-({5-Oxo-1-[8-(propane-1-sulfonyl)-8α-aza-bicyclo[3.2.1]oct-3-ylmethyl]-4,4-bis-pyridin-4-ylmethyl-imidazolidin-2-ylidene}-acetyl)-benzonitrile;

3-{2-[2-(4-Cyano-phenyl)-2-oxo-ethylidene]--oxo-4,4-bis-pyridin-4-ylmethyl-imidazolidin-1-ylmethyl}8α-aza-bicyclo[3.2.1]octane-8-sulfonic acid dimethylamide; and 4-({1-[8-(1-Methyl-1H-imidazole-4-sulfonyl)-8p-aza-bicyclo3.2.1]oct-3-ylmethyl]-5 oxo--4,4-bis-pyridin-4-ylmethyl-imidazolidin-2-ylidene}-acetylybenzonitrile.

5. A method of inhibiting unregulated cell growth caused by farnesyl protein transferase activity in a mammal, comprising administering to said mammal an amount of a compound according to claim 1 that is effective in inhibiting farnesyl protein transferase.

6. A pharmaceutical composition for inhibiting unregulated cell growth caused by farnesyl protein transferase activity in a mammal, comprising an amount of a compound according to claim 1 that is effective in inhibiting farnesyl protein transferase and a pharmaceutically acceptable carrier.

7. A method of inhibiting abnormal cell growth in a mammal, comprising administering to said mammal an amount of a compound according to claim 1 that is effective in inhibiting abnormal cell growth.

8. A pharmaceutical composition for inhibiting abnormal cell growth in a mammal, comprising an amount of a compound according to claim 1 that is effective in inhibiting abnormal cell growth and a pharmaceutically acceptable carrier.

9. A method for inhibiting abnormal cell growth in a mammal which comprises administering to said mammal an amount of a compound according to claim 1 and an amount of an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, and anti-hormones, wherein the amount of said anti-tumor agent is, in combination with the amount of the compound of claim 1, effective to inhibit abnormal cell growth in the mammal.

10. A pharmaceutical composition for inhibiting abnormal cell growth in a mammal which comprises an amount of a compound according to claim 1; an amount of an antitumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, and anti-hormones; and a pharmaceutically acceptable carrier; wherein the amount of said anti-tumor agent is, in combination with the amount of the compound of claim 1, effective to inhibit abnormal cell growth in a mammal.

* * * * *